(12) United States Patent
Cool et al.

(10) Patent No.: US 10,471,091 B2
(45) Date of Patent: Nov. 12, 2019

(54) HEPARAN SULPHATES FOR USE IN REPAIR AND/OR REGENERATION OF SKIN

(71) Applicant: Agency for Science, Technology and Research, Singapore (SG)

(72) Inventors: Simon Cool, Singapore (SG); Victor Nurcombe, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 15/527,972

(22) PCT Filed: Nov. 19, 2015

(86) PCT No.: PCT/SG2015/050464
§ 371 (c)(1),
(2) Date: May 18, 2017

(87) PCT Pub. No.: WO2016/080916
PCT Pub. Date: May 26, 2016

(65) Prior Publication Data
US 2017/0319615 A1    Nov. 9, 2017

(30) Foreign Application Priority Data

Nov. 19, 2014    (SG) .......................... 10201408007P

(51) Int. Cl.
| | | |
|---|---|---|
| *A61K 31/727* | (2006.01) | |
| *A61K 35/28* | (2015.01) | |
| *A61P 17/02* | (2006.01) | |
| *C08B 37/00* | (2006.01) | |
| *A61K 38/18* | (2006.01) | |
| *A61K 9/00* | (2006.01) | |
| *A61L 15/28* | (2006.01) | |
| *A61L 26/00* | (2006.01) | |

(52) U.S. Cl.
CPC .......... *A61K 31/727* (2013.01); *A61K 9/0014* (2013.01); *A61K 35/28* (2013.01); *A61K 38/1825* (2013.01); *A61L 15/28* (2013.01); *A61L 26/0023* (2013.01); *A61P 17/02* (2018.01); *C08B 37/0075* (2013.01)

(58) Field of Classification Search
CPC ... A61K 31/727; A61K 38/1825; A61P 17/02; C08B 37/0075
See application file for complete search history.

(56) References Cited

U.S. PATENT DOCUMENTS

| | | |
|---|---|---|
| 10,266,612 B2 | 4/2019 | Nurcombe et al. |
| 2006/0183712 A1 | 8/2006 | McKeehan et al. |
| 2010/0168055 A1 | 7/2010 | Laboureau et al. |
| 2011/0288047 A1 | 11/2011 | De Ambrosi |
| 2013/0071443 A1 | 3/2013 | Cool et al. |
| 2016/0115251 A1 | 4/2016 | Nurcombe et al. |
| 2017/0326059 A1 | 11/2017 | Cool et al. |

FOREIGN PATENT DOCUMENTS

| | | |
|---|---|---|
| EP | 0509517 A2 | 10/1992 |
| JP | H0240399 A | 2/1990 |
| WO | WO-92/02539 A1 | 2/1992 |
| WO | WO-93/19096 A1 | 9/1993 |
| WO | WO-1996/023003 A1 | 8/1996 |
| WO | WO-2010/011185 A1 | 1/2010 |
| WO | WO-2010/029278 A2 | 3/2010 |
| WO | WO-2010/030241 A1 | 3/2010 |
| WO | WO-2010/030244 A1 | 3/2010 |
| WO | WO-2010/057710 A2 | 5/2010 |
| WO | WO-2014/185858 A1 | 11/2014 |

OTHER PUBLICATIONS

Jackson, W. et al "Concise review: clinical translation of wound healing . . . " Stem Cells Translat. Med., vol. 1, pp. 44-50. (Year: 2012).*
Wijesinghe, S. et al "Affinity selection of FGF2-binding heparan sulfates . . . " J. Cell. Physiol., vol. 232, pp. 566-575. (Year: 2017).*
Ackermann, et al., Priming with proangiogenic growth factors and endothelial progenitor cells improves revascularization in linear diabetic wounds et al., Int. J. Mol. Med., 33: 833-839 (2014).
Baird, A. et al., Receptor- and heparin-binding domains of basic fibroblast growth factor, Proc. Natl. Acad. Sci. USA, 85:2324-2328 (1988).
Bramono, D.S. et al., The Effect of Human Bone Marrow Stroma-Derived Heparan Sulfate on the Ex Vivo Expansion of Human Cord Blood Hematopoietic Stem Cells, Pharm Res., 28:1385-1194 (2011).
Brickman, Y.G. et al., Heparan sulfates mediate the binding of basic fibroblast growth factor to a specific receptor on neural precursor cells, Journal of Biological Chemistry, 270(42): 24941-24948 (1995).
Correa, et al., A graph-structural method for prediction of polymer properties, Brazilian Journal of Chemical Engineering, 21(4): 621-628 (2004).
Desgranges, P. et al., Beneficial use of fibroblast growth factor 2 and RGTA, a new family of heparan mimics, for endothelialization of PET prostheses, Journal of Biomedical Materials Research, 58(1): 1-9 (2000).
Dombrowski, C. et al., Heparan sulfate mediates the proliferation and differentiation of rat mesenchymal stem cells, Stem Cells and Development, 18(4): 661-670 (2009).
Dominici, M. et al., Minimal criteria for defining multipotent mesenchymal stromal cells. The International Society for Cellular Therapy position statement, Cytotherapy, 8(4): 315-317 (2006).

(Continued)

*Primary Examiner* — Leigh C Maier
(74) *Attorney, Agent, or Firm* — Choate, Hall & Stewart LLP; Charles E. Lyon; Kristen C. Buteau

(57) ABSTRACT

Affinity purification of fibroblast growth factor 2-binding heparan sulphate from porcine mucosa (HS8) is disclosed. Also disclosed is the use of HS8 in repair and regeneration of the skin for treating wounds, burns, ulcers and other skin injuries.

20 Claims, 56 Drawing Sheets
Specification includes a Sequence Listing.

(56) References Cited

OTHER PUBLICATIONS

Gallo, R.L. et al., The Potential Role of Topically Applied Heparan Sulfate in the Treatment of Photodamage, J. Drugs Dermatol., 14(7): 669-674 (2015).
Gandhi, et al., The structure of glycosaminoglycans and their interactions with proteins, Chem. Biol. Drug Des., 72: 455-482 (2008).
Gang, E.J. et al., SSEA-4 identifies mesenchymal stem cells from bone marrow, Blood, 109(4): 1743-1751 (2007).
Garcia-Filipe et al., RGTA OTR4120, a heparan sulfate mimetic, is a possible long-term active agent to heal burned skin, J. Biomed. Mater. Res. A, 80(1): 75-84 (2007).
Gronthos, S. et al., Differential Cell Surface Expression of the STRO-1 and Alkaline Phosphatase Antigens on 3Discrete Developmental Stages in Primary Cultures of Human Bone Cells, Journal of Bone and Mineral Research, 14(1): 47-56 (1999).
Helledie, T. et al., Heparan sulfate enhances the self-renewal and therapeutic potential of mesenchymal stem cells from human adult bone marrow, Stem Cells Dev., 21(11):1897-1910 (2012).
International Search Report for PCT/SG2013/000201, 4 pages (dated Aug. 23, 2013).
International Search Report for PCT/SG2015/050462, 6 pages (dated Jan. 27, 2016).
International Search Report for PCT/SG2015/050464, 6 pages (dated Jan. 27, 2016).
Jackson, R.A. et al., Coordinated fibroblast growth factor and heparan sulfate regulation of osteogenesis, Gene, 379: 79-91 (2006).
Jackson, R.A. et al., The use of heparan sulfate to augment fracture repair in a rat fracture model, J Orthop Res., 24(4):636-644 (2006).
Jackson, R.L. et al., Glycosaminoglycans: Molecular Properties, Protein Interactions, and Role in Physiological Processes, Physiol. Rev., 71(2): 481-539 (1991).
Maccarana, M. et al., Minimal Sequence in Heparin/Heparan Sulfate Required for Binding of Basic Fibroblast Growth Factor, The Journal of Biological Chemistry, 268(32): 23898-23905 (1993).
Manton, K.J. et al., Disruption of heparan and chondroitin sulfate signaling enhances mesenchymal stem cell-derived osteogenic differentiation via bone morphogenetic protein signaling Pathways, Stem Cells, 25(11): 2845-2854 (2007).
Murali, S. et al., Comparative assessment of the effects of gender-specific heparan sulfates on mesenchymal stem cells, The Journal of Biological Chemistry, 286(20): 17755-17765 (2011).
Murali, S. et al., Purification and characterization of heparan sulfate from human primary osteoblasts, Journal of Cellular Biochemistry, 108(5): 1132-1142 (2009).
Nakamizo, S. et al., Topical Treatment with Basic Fibroblast Growth Factor Promotes Wound Healing and Barrier Recovery Induced by Skin Abrasion, Skin Pharmacol. Physiol., 26(1): 22-29 (2012).
Ori, A. et al., Identification of Heparin-binding Sites in Proteins by Selective Labeling, Mol. Cell Proteomics, 8(10): 2256-2265 (2009).
Rider, D.A. et al., Selection using the alpha-1 integrin (CDF94a) enhances the multipotentiality of the mesenchymal stem cell population from heterogeneous bone marrow stromal cells, J. Mol. Hist., 38: 449-458 (2007).
Saksela, O. et al., Endothelial Cell-derived heparan sulfate binds basic fibroblast growth factor and protects it from proteolytic degradation, The Journal of Cell Biology, 107: 743-751 (1988).
Schmidt, A. et al., Basic Fibroblast Growth Factor Controls Migration in Human Mesenchymal Stem Cells, Stem Cells, 24(7): 1750-1758 (2006).
Schultz, G.S. et al., Interactions between extracellular matrix and growth factors in wound healing, Wound Repair and Regeneration, 17(2): 153-162 (2009).
Sogabe, Y. et al., Basic fibroblast growth factor stimulates human keratinocyte motility by Rac activation, Wound Rep. Regen., 14(4): 457-462 (2006).
Tong, M. et al., Diabetes-Impaired Wound Healing Is Improved by Matrix Therapy with Heparan Sulfate Glycosaminoglycan Mimetic OTR4120 in Rats, Diabetes, 61(10): 2633-2641 (2012).
Wijesinghe, S.J. et al., Affinity Selection of FGF2-Binding Heparan Sulfates for Ex Vivo Expansion of Human Mesenchymal Stem Cells, J Cell Physiol., 232(3): 566-575 (2017).
Written Opinion for PCT/SG2013/000201, 6 pages (dated Aug. 23, 2013).
Written Opinion for PCT/SG2015/050462, 7 pages (dated Jan. 27, 2016).
Written Opinion for PCT/SG2015/050464, 7 pages (dated Jan. 27, 2016).
Zakine, G. et al., Matrix Therapy with RGTA OTR4120 Improves Healing Time and Quality in Hairless Rats with Deep Second-Degree Burns, Plast. Reconstr. Surg., 127(2): 541-550 (2011).
Belting, M. Heparan sulfate proteoglycan as a plasma membrane carrier, Trends in Biochemical Sciences, 28(3): 145-151 (2003).
Fromm, J.R. et al., Pattern and Spacing of Basic Amino Acids in Heparin Bing Sites, Archives of Biochemistry and Biophysics, 343(1): 92-100 (1997).
Kundrotas, G., Surface markers distinguishing mesenchymal stem cells from fibroblasts, Acta Medica Lituanica, 19(2): 75-79 (2012).
Shriver, Z., Heparin and Heparan Sulfate: Analyzing Structure and Microheterogeneity, Handb Exp Pharmacol., (207): 159-176. (2012).

\* cited by examiner

|   | Residue/ Size | Sequence | Reference |
|---|---|---|---|
| 1 | 248-254/ 7aa | $^{248}$YKRSRYT$^{254}$ -paper<br>Have to be $^{248}$YRSRKYT$^{254}$ | Lee et al, 2007 |
| 2 | 261-277/17aa | $^{261}$KRTGQYKLGSKTGPGQK$^{277}$ | |
| 3 | 260-277aa/18aa | $^{260}$LKRTGQYKLGSKTGPGQK$^{277}$ | Hileman et al, 1998 |
| 5 | 235-262/ 28aa | $^{235}$FFFERLESNNYNTYRSRKYTSWYVALKR$^{262}$ | Baird et al, 1998 |
| 6 | 157-172/ 16aa | $^{157}$GHFKDPKRLYCKNGGF$^{172}$ | Gandhi et al, 2008 |
| 8 | 185-194/ 10aa | $^{185}$VREKSDPHIK$^{194}$ | Kinsella, et al, 1998 |
| 9 | 250-259/ 10aa | $^{250}$SRKYTSWYVA$^{259}$ | |
| 10 | 260-273/14aa | $^{260}$LKRTGQYKLGSKTG$^{273}$ | |
| 11 | 260-280/21aa | $^{260}$LKRTGQYKLGSKTGPGQKAIL$^{280}$ | Ashikari-Hada et al,2004 |
| 13 | 168-169,223,261-277-20aa | $^{168}$KN$^{169}$ $^{223}$R $^{261}$KRTGQYKLGSKTGPGQK$^{277}$ | Ori et al, 2009, Faham et al, 1996, Thomson et al, 1985 and Baird et al, 1998 |
| 14 | 235-262/28aa | $^{235}$FFFERLESNNYNTYRSRKYTSWYVALKR$^{262}$ | |
| 15 | 216-225/10aa | $^{216}$LAMKEDGRLL$^{225}$ | |

Figure 5

| Cell surface marker | P4 Control | P7 Control | P7 * HS8(+) | P7 ** HS8(+) | P7* HS8(-) | P7 * CHS | P7* Heparin | P7 # FGF-2 |
|---|---|---|---|---|---|---|---|---|
| CD 14 | 0.784 | 0.74 | 0.502 | 0.82 | 4.19 | 0.813 | 0.503 | 0.961 |
| CD 19 | 0.9725 | 0.718 | 1.05 | 0.825 | 1.36 | 1.43 | 0.937 | 0.815 |
| CD 34 | 1.0225 | 0.625 | 0.899 | 0.554 | 1.04 | 0.859 | 0.867 | 1.05 |
| CD 45 | 0.9235 | 0.745 | 0.797 | 0.817 | 1.15 | 0.914 | 0.728 | 1.1 |
| HLA-DR | 1.045 | 0.981 | 1.16 | 1.27 | 0.924 | 1.13 | 0.971 | 1.3 |
| CD 73 | 99.95 | 99.9 | 99.9 | 99.9 | 100 | 100 | 99.8 | 99.8 |
| CD 90 | 99.6 | 99.9 | 100 | 100 | 100 | 100 | 99.5 | 90.8 |
| CD 105 | 99.95 | 99.9 | 99.9 | 99.9 | 100 | 99.9 | 99.4 | 99.9 |
| CD49a | 34 | 51.1 | 50.7 | 61.4 | 67.5 | 84.1 | 52.5 | 28 |
| SSEA-4 | 33.65 | 57.5 | 66.1 | 71 | 12.9 | 63.2 | 73.4 | 83.7 |
| STRO-1 | 24.1 | 33.7 | 25.3 | 34.9 | 28 | 26.2 | 34.5 | 3.58 |

P= Passage, * with a dose of 1.25µg/ml, ** with a dose of 2.5µg/ml and # with a dose of 2.5ng/ml

Figure 22

MVGVGGGDVE DVTPRPGGCQ ISGRGARGCN GIPGAAAWEA ALPRRRPRRH PSVNPRSRAA
GSPRTRGRRT EERPSGSRLG DRGRGRALPG GRLGGRGRGR APERVGGRGR GRGTAAPRAA
PAARGSRPGP AGTMAAGSIT TLPALPEDGG SGAFPP<u>GHFK DPKRLYCKNG G</u>FFLRIHPDG
RVDGVREKSD PHIKLQLQAE ERGVVSIKGV CANRYLAMKE DGRLLASKCV TDECFFFERL
ESNNYNTYRS RKYTSWYVAL KRTGQYKLGS KTGPGQKAIL FLPMSAKS

Figure 28

| | %E10 GAG |
|---|---|
| DISACCHARIDE | |
| IdoA/GlcA-AMann$_R$ | 12.9 |
| IdoA(2S)-AMann$_R$ | 53.4 |
| GlcA-AMann$_R$(6S) | 10.25 |
| IdoA-AMann$_R$(6S) | 3.4 |
| IdoA(2S)-AMann$_R$(6S) | 18.7 |
| GlcA(2S)-AMann$_R$ | 1.0 |
| GlcA-AMann$_R$(3S) | 0.30 |
| GlcA- AMann$_R$(3,6S) | 0.15 |
| UNKNOWN | 0.0 |

Figure 29

| PEAK NUMBER | DISACCHARIDE | % in E10 GAG |
|---|---|---|
| 1 | ΔHexUA-GlcNAc | 44.8 |
| 3 | ΔHexUA-GlcNSO$_3$ | 21.5 |
| 2 | ΔHexUA-GlcNAc(6S) | 8.0 |
| 7 | ΔHexUA(2S)-GlcNAc | 2.4 |
| 4 | ΔHexUA-GlcNSO$_3$(6S) | 4.0 |
| 5 | ΔHexUA(2S)-GlcNSO$_3$ | 12.4 |
| 8 | ΔHexUA(2S)-GlcNAc(6S) | 0.2 |
| 6 | ΔHexUA(2S)-GlcNSO$_3$(6S) | 4.1 |
| 9 | unknown | 2.4 |

Figure 30

| Disaccharide | Celsus HS | HS3 (848/HS3/001) | HS8 |
|---|---|---|---|
| ΔHexUA,2S-GlcNS,6S | 8.3 | 14.8 | 12.7 |
| ΔHexUA,2S-GlcNS | 5.1 | 4.9 | 7.2 |
| ΔHexUA-GlcNS,6S | 9.1 | 11.1 | 15.5 |
| ΔHexUA,2S-GlcNAc,6S | 3.3 | 4.8 | 6.5 |
| ΔHexUA-GlcNS | 26.9 | 22.2 | 15.7 |
| ΔHexUA,2S-GlcNAc | 1.6 | 1.1 | 1.0 |
| ΔHexUA-GlcNAc,6S | 10.8 | 10.1 | 8.9 |
| ΔHexUA-GlcNAc | 34.9 | 31.0 | 32.5 |
| Total | 100.0 | 100.0 | 100.0 |

Mean average of duplicate analyses of duplicate hydrolysates
Normalised weight percentage disaccharide Day 0

Wound at Day 7

CMC

Wound at Day 7

HS8

SEQUENCE LISTING

```
<160> NUMBER OF SEQ ID NOS: 15

<210> SEQ ID NO 1
<211> LENGTH: 16
<212> TYPE: PRT
<213> ORGANISM: Homo sapiens

<400> SEQUENCE: 1

Gly His Phe Lys Asp Pro Lys Arg Leu Tyr Cys Lys Asn Gly Gly Phe
1               5                   10                  15

<210> SEQ ID NO 2
<211> LENGTH: 7
<212> TYPE: PRT
<213> ORGANISM: Homo sapiens

<400> SEQUENCE: 2

Tyr Cys Lys Asn Gly Gly Phe
1               5

<210> SEQ ID NO 3
<211> LENGTH: 288
<212> TYPE: PRT
<213> ORGANISM: Homo sapiens

<400> SEQUENCE: 3

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Arg Gly Ser Arg Pro
            115                 120                 125

Gly Pro Ala Gly Thr Met Ala Ala Gly Ser Ile Thr Thr Leu Pro Ala
            130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190
```

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
        275                 280                 285

<210> SEQ ID NO 4
<211> LENGTH: 7
<212> TYPE: PRT
<213> ORGANISM: Homo sapiens

<400> SEQUENCE: 4

Tyr Lys Arg Ser Arg Tyr Thr
1               5

<210> SEQ ID NO 5
<211> LENGTH: 7
<212> TYPE: PRT
<213> ORGANISM: Homo sapiens

<400> SEQUENCE: 5

Tyr Arg Ser Arg Lys Tyr Thr
1               5

<210> SEQ ID NO 6
<211> LENGTH: 17
<212> TYPE: PRT
<213> ORGANISM: Homo sapiens

<400> SEQUENCE: 6

Lys Arg Thr Gly Gln Tyr Lys Leu Gly Ser Lys Thr Gly Pro Gly Gln
1               5                   10                  15

Lys

<210> SEQ ID NO 7
<211> LENGTH: 18
<212> TYPE: PRT
<213> ORGANISM: Homo sapiens

<400> SEQUENCE: 7

Leu Lys Arg Thr Gly Gln Tyr Lys Leu Gly Ser Lys Thr Gly Pro Gly
1               5                   10                  15

Gln Lys

<210> SEQ ID NO 8
<211> LENGTH: 28
<212> TYPE: PRT
<213> ORGANISM: Homo sapiens

<400> SEQUENCE: 8

Phe Phe Phe Glu Arg Leu Glu Ser Asn Asn Tyr Asn Thr Tyr Arg Ser
1               5                   10                  15

Arg Lys Tyr Thr Ser Trp Tyr Val Ala Leu Lys Arg
            20                  25

<210> SEQ ID NO 9
<211> LENGTH: 10
<212> TYPE: PRT
<213> ORGANISM: Homo sapiens

<400> SEQUENCE: 9

Val Arg Glu Lys Ser Asp Pro His Ile Lys
1               5                   10

<210> SEQ ID NO 10
<211> LENGTH: 10
<212> TYPE: PRT
<213> ORGANISM: Homo sapiens

<400> SEQUENCE: 10

Ser Arg Lys Tyr Thr Ser Trp Tyr Val Ala
1               5                   10

<210> SEQ ID NO 11
<211> LENGTH: 14
<212> TYPE: PRT
<213> ORGANISM: Homo sapiens

<400> SEQUENCE: 11

Leu Lys Arg Thr Gly Gln Tyr Lys Leu Gly Ser Lys Thr Gly
1               5                   10

<210> SEQ ID NO 12
<211> LENGTH: 21
<212> TYPE: PRT
<213> ORGANISM: Homo sapiens

<400> SEQUENCE: 12

Leu Lys Arg Thr Gly Gln Tyr Lys Leu Gly Ser Lys Thr Gly Pro Gly
1               5                   10                  15

Gln Lys Ala Ile Leu
            20

<210> SEQ ID NO 13
<211> LENGTH: 17
<212> TYPE: PRT
<213> ORGANISM: Homo sapiens

<400> SEQUENCE: 13

Lys Arg Thr Gly Gln Tyr Lys Leu Gly Ser Lys Thr Gly Pro Gly Gln
1               5                   10                  15

Lys

<210> SEQ ID NO 14
<211> LENGTH: 10
<212> TYPE: PRT
<213> ORGANISM: Homo sapiens

<400> SEQUENCE: 14

Leu Ala Met Lys Glu Asp Gly Arg Leu Leu
1               5                   10

<210> SEQ ID NO 15
<211> LENGTH: 18
<212> TYPE: PRT
<213> ORGANISM: Artificial sequence
<220> FEATURE:
<223> OTHER INFORMATION: Synthetic peptide

```
<220> FEATURE:
<221> NAME/KEY: SITE
<222> LOCATION: (17)..(17)
<223> OTHER INFORMATION: Xaa is Ahx
<220> FEATURE:
<221> NAME/KEY: SITE
<222> LOCATION: (18)..(18)
<223> OTHER INFORMATION: Lys is (K)Biotin

<400> SEQUENCE: 15

Gly His Phe Lys Asp Pro Lys Arg Leu Tyr Cys Lys Asn Gly Gly Phe
1               5                   10                  15

Xaa Lys
```

HEPARAN SULPHATES FOR USE IN REPAIR AND/OR REGENERATION OF SKIN

FIELD OF THE INVENTION

The present invention relates to heparan sulphates including heparan sulphates that bind FGF2, and particularly, although not exclusively, to their therapeutic use in the repair and/or regeneration of skin.

BACKGROUND TO THE INVENTION

Skin constitutes the largest organ of the human body, serving as a protective barrier against physical injury, radiation and temperature. Skin consists of an underlying mesenchymal (dermal) layer and an outer epithelial (epidermal) layer.

Skin wound healing is regulated by various mechanisms including cell-cell interactions, extracellular matrix production and a number of cytokines and growth factors (see Paul Martin. Wound Healing—Aiming for Perfect Skin Regeneration. Science 276 (75) 1997). Important aims of wound treatment include rapid wound closure and a functionally and aesthetically satisfactory scar.

Wound healing in skin proceeds via an overlapping pattern of events including coagulation, inflammation, tissue formation (epithelialization, formation of granulation tissue, matrix) and tissue remodeling. The process of repair is mediated in large part by interacting molecular signals, primarily cytokines. Initial injury triggers coagulation and an acute local inflammatory response followed by mesenchymal stem cell recruitment, proliferation and matrix synthesis. Failure to resolve the inflammation can lead to chronic non healing wounds, whereas uncontrolled matrix accumulation, can lead to excess scarring.

One of the major growth factors known to be crucial for skin wound healing is fibroblast growth factor-2 (FGF-2), which belongs to a family of similar heparin-binding proteins made by many types of cell, including fibroblasts, melanocytes, endothelial cells and especially stem cells. FGF-2 plays a role in a multitude of developmental and biological processes, including limb development, tissue repair, mesoderm induction, lung development and maintenance of neuron survival; in particular, FGF-2 regulates cell proliferation, migration, and differentiation, including the dermis and epidermis. An FGF-2 variant has been approved by the Food and Drug Administration (FDA) for several Phase-III clinical trials, including peripheral angiogenesis. FGF-2 has both a proliferative and motile effect on keratinocytes, and augments the activities of skin-derived mesenchymal stem cells. FGF-2 is also proto-oncogenic, which makes its use at high concentrations problematic, and alternative therapies are therefore needed.

FGF-2 has a proliferative and motile effect on keratinocytes during wound healing and augments skin-derived mesenchymal stem cells. FGF-2 treatment is effective for the repair of radiation-exposed skin. It's use as a topical treatment for second degree burn wounds has also been evaluated, where significantly faster wound healing as well as larger maximal scar extension, scar retraction to maximal scar extension ratio and elasticity were confirmed. It also supports scarless wound healing by induction of myofibroblast apoptosis but sparing the same effect on fibroblasts.

Re-epithelialization is a critical event in human skin wound healing, in which epidermal keratinocytes laterally migrate to close a wound. In chronic wounds, keratinocyte migration is blocked and the wounds remain open, causing patient morbidity and even fatality. During human skin wound healing, an important step is the initiation of the epidermal and dermal cells at the wound edge to migrate into the wound bed. Human keratinocytes (HKCs) laterally migrate across the wound bed from the cut edge to eventually close the wound (re-epithelialization). The dermal cells, including dermal fibroblasts (DFs) and dermal microvascular endothelial cells (HDMECs), move into the wound following the HKC migration, where these cells deposit matrix proteins, contract and remodel the newly closed wound and build new blood vessels.

Brickman et al. (Glycobiology Vo. 8 No. 5 pp. 463-471, 1998) describe an heparan sulphate called HS2 reported to be capable of interacting with FGF2. HS2 is obtainable from heparan proteoglycans of murine cells at embryonic day 10 as described by Brickman (supra). HS2 has been described as having a molecular weight of approximately 25 kDa and thus, assuming an average molecular mass of 400 Da per disaccharide, consists of about 60 disaccharides. The disaccharide composition of HS2 is set forth in Brickman et al. (Glycobiology Vo. 8 No. 5 pp. 463-471, 1998), WO2010/011185, which is herein incorporated by reference in its entirety. The nitrous acid and heparan lyase digestion profiles of HS2 are shown in FIGS. 29 and 30.

Maccarana et al (Minimal Sequence in Heparin/Heparan Sulfate Required for Binding of Basic Fibroblast Growth Factor. The Journal of Biological Chemistry. Vol. 268, No. 32, Issue 15, pp 23898-23905, 1993) describes experiments investigating the binding of FGF-2 by several small oligosaccharides generated from heparin or HS from human aorta. One octasaccharide fraction (B2) was used to ascribe a structure to the octasaccharide, which the authors called HS-8. It should be noted that this is not the HS-8 of the present invention and the nomenclature is entirely coincidental.

Heparin from pig intestinal mucosa, two samples of selectively O-desulfated heparin, one sample generated by preferential 6-O-desulfation together with N-desulfation of the starting material followed by re-N-sulfation, another sample obtained by selective 2-O-desulfation under alkaline conditions, a low sulphated HS isolated from human aorta, and HS from bovine kidney were used to generate low chain length oligosaccharides of even or odd number.

Even number oligosaccharides were generated from heparin by depolymerisation through partial deaminative cleavage with nitrous acid and the resulting 2,4-anhydro-D-mannose residues were reduced with $NAB^3H_4$. Labeled oligosaccharides were separated to generate even numbered species from 4-14 saccharides and a fraction containing 20-24 saccharides. The selectively 6-O-desulfated heparin was similarly treated to yield 4- to 12-saccharides. The isolated and desalted oligosaccharides were subjected to mild acid treatment. Odd numbered heparin oligosaccharides were obtained by further treatment of the 20-24-meric saccharides with heparinase I.

4-14-meric oligosaccharides were generated from human aorta HS by a different strategy involving cleavage at sites occupied by N-acetylated GlcN units. Samples were N-deacetylated and then deaminated with nitrous acid. This treatment leads to deamination of unsubstituted GlcN units and cleavage of glucosaminidic linkages whereas N-sulfated GlcN units remain intact. The products include GlcA-[1-$^3$H] aMan$_R$ disaccharides (derived from (-GlcNAc)-(GlcA-Glc-Nac)$_n$- sequences) and GlcA-GlcNSO$_3$-HexA)$_n$-[1-$^3$H] aMan$_R$ oligosaccharides (derived from (-GlcNac)-GlcA-(GlcNSO$_3$-HexA)$_n$-GlcNac- sequences).

The oligosaccharides generated by these treatments were both short and chemically modified by the process of their preparation, which distinguishes them from the HS of the present invention.

SUMMARY OF THE INVENTION

The present invention concerns a heparan sulphate preparation, heparan sulphate HS8. HS8 has been found to bind FGF2 and enhance the proliferation of stem cells whilst maintaining their pluripotency/multipotency. HS8 refers to a novel class of structurally and functionally related isolated heparan sulphate. The inventors have identified several closely related members of the HS8 class that have the common property of binding to heparin binding domains derived from FGF2 that share a short consensus sequence (YCKNGGF). Members of the HS8 class are able to stimulate the proliferation of stem cells and enrich for colonly forming units.

In one aspect of the present invention an heparan sulphate HS8 is provided. HS8 may be provided in isolated form or in substantially purified form. This may comprise providing a composition in which the heparan sulphate component is at least 80% HS8, more preferably one of at least 85%, 90%, 95%, 96%, 97%, 98%, 99% or 100%.

In preferred embodiments, HS8 is capable of binding a peptide or polypeptide having the amino acid sequence of YCKNGGF (SEQ ID NO: 2). The peptide may have one or more additional amino acids at one or both ends of this sequence. For example, the peptide may have any of 1, 2, 3, 4, 5, 6, 7, 8, 9, 10, 11, 12, 13, 14, 15, 16, 17, 18, 19, 20 or more amino acids at one or both end of this sequence.

In some embodiments, HS8 is capable of binding a peptide or polypeptide having, or consisting of, the amino acid sequence of any one of:

YCKNGGF, (SEQ ID NO: 2)

or

GHFKDPKRLYCKNGGF. (SEQ ID NO: 1)

In other embodiments the polypeptide is an FGF2 protein. In some embodiments HS8 binds to a peptide having or consisting of the amino acid sequence of any of SEQ ID NOs:1, 2 or FGF2 protein with a $K_D$ of less than 100 μM, more preferably less than one of 50 μM, 40 μM, 30 μM, 20 μM, or 10 μM.

HS8 may be obtained, identified, isolated or enriched according to the inventors' methodology described herein, which may comprise the following steps:
 (i) providing a solid support having polypeptide molecules adhered to the support, wherein the polypeptide comprises a heparin-binding domain having the amino acid sequence of YCKNGGF;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans.

In some embodiments the polypeptide adhered to the support may comprise or consist of an amino acid sequence selected from

YCKNGGF, (SEQ ID NO: 2)

or

GHFKDPKRLYCKNGGF. (SEQ ID NO: 1)

In the inventors' methodology the mixture may comprise glycosaminoglycans obtained from commercially available sources. One suitable source is a heparan sulphate fraction, e.g. a commercially available heparan sulphate. One suitable heparan sulphate fraction can be obtained during isolation of heparin from porcine intestinal mucosa (e.g. Celsus Laboratories Inc.—sometimes called "Celsus HS").

Other suitable sources of heparan sulphate include heparan sulphate from any mammal (human or non-human), particularly from the kidney, lung or intestinal mucosa. In some embodiments the heparan sulphate is from pig (porcine) or cow (bovine) intestinal mucosa, kidney or lung.

In another aspect of the present invention a composition comprising HS8 according to any one of the aspects above and FGF2 protein is provided.

In one aspect of the present invention a pharmaceutical composition or medicament is provided comprising HS8 in accordance with the aspects described above. The pharmaceutical composition or medicament may further comprise a pharmaceutically acceptable carrier, adjuvant or diluent.

In some embodiments the pharmaceutical composition is for use in a method of treatment, the method comprising the repair and/or regeneration of tissue, e.g. a broken bone. In some embodiments the pharmaceutical composition or medicament may further comprise FGF2 protein. In some embodiments the pharmaceutical composition or medicament may further comprise mesenchymal stem cells.

In another aspect of the present invention HS8 is provided for use in a method of medical treatment. The method of medical treatment may comprise a method of wound healing in vivo, the repair and/or regeneration of tissue, the repair and/or regeneration of connective tissue, the repair and/or regeneration of bone and/or the repair and/or regeneration of bone in a mammal or a human.

In a related aspect of the present invention the use of HS8 in the manufacture of a medicament for use in a method of medical treatment is provided. In some embodiments the method of medical treatment comprises the repair and/or regeneration of a broken bone in a mammal or a human.

In a further aspect of the present invention a biocompatible implant or prosthesis comprising a biomaterial and HS8 is provided. In some embodiments the implant or prosthesis is coated with HS8. In some embodiments the implant or prosthesis is impregnated with HS8. The implant or prosthesis may be further coated or impregnated with FGF2 protein and/or with mesenchymal stem cells.

In another aspect of the present invention a method of forming a biocompatible implant or prosthesis is provided, the method comprising the step of coating or impregnating a biomaterial with HS8. In some embodiments the method further comprises coating or impregnating the biomaterial with one or both of FGF2 protein and mesenchymal stem cells.

In another aspect of the present invention a method of treating a bone fracture in a patient is provided, the method comprising administration of a therapeutically effective amount of HS8 to the patient. In some embodiments the method comprises administering HS8 to the tissue surrounding the fracture. In some embodiments the method comprises injection of HS8 to the tissue surrounding the fracture.

In such methods the HS8 may be formulated as a pharmaceutical composition or medicament comprising HS8 and a pharmaceutically acceptable carrier, adjuvant or diluent.

In some embodiments the method may further comprise administering FGF2 protein to the patient. In such methods the HS8 and FGF2 protein may be formulated as a pharmaceutical composition comprising HS8 and FGF2 protein and a pharmaceutically acceptable carrier, adjuvant or diluent.

In some embodiments the method may further comprise administering mesenchymal stem cells to the patient. In such methods at least two of HS8, FGF2 protein and mesenchymal stem cells may be formulated in a pharmaceutical composition comprising at least two of the HS8, FGF2 protein and mesenchymal stem cells and a pharmaceutically acceptable carrier, adjuvant or diluent.

Preferably, the HS8, FGF2 protein and mesenchymal stem cells are respectively provided in therapeutically effective amounts. In some embodiments the method of treating bone fracture further comprises the step of formulating therapeutically effective amounts of HS8, and/or FGF2 protein and/or mesenchymal stem cells as a pharmaceutical composition comprising the HS8, and/or FGF2 protein and/or mesenchymal stem cells and a pharmaceutically acceptable carrier, adjuvant or diluent, wherein the pharmaceutical composition is administered to the patient.

In another aspect of the present invention a method of treating a bone fracture in a patient is provided, the method comprising surgically implanting a biocompatible implant or prosthesis, which implant or prosthesis comprises a biomaterial and HS8, into tissue of the patient at or surrounding the site of fracture.

In some embodiments the implant or prosthesis is coated with HS8. In some embodiments the implant or prosthesis is impregnated with HS8. In some embodiments the implant or prosthesis is further impregnated with one or both of FGF2 protein and mesenchymal stem cells.

In yet a further aspect of the present invention a method for the repair, replacement or regeneration of tissue in a human or animal patient in need of such treatment is provided, the method comprising:
(i) culturing mesenchymal stem cells in vitro in contact with HS8 for a period of time sufficient for said cells to form tissue;
(ii) collecting said tissue;
(iii) implanting said tissue into the body of the patient at a site of injury or disease to repair, replace or regenerate tissue in the patient.

The tissue may be connective tissue, e.g. bone, cartilage, tendon, or fat.

In some embodiments the method further comprises contacting the mesenchymal stem cells in culture with exogenous FGF2 protein.

In another aspect of the present invention tissue obtained by in vitro culture of mesenchymal stem cells in the presence of HS8 is provided. In some embodiments the tissue is obtained by in vitro culture of mesenchymal stem cells in the presence of HS8 and FGF2 protein.

In yet a further aspect of the present invention a kit of parts is provided, the kit comprising a predetermined amount of HS8 and a predetermined amount of FGF2. The kit may comprise a first container containing the predetermined amount of HS8 and a second container containing the predetermined amount of FGF2. The kit may further comprise a predetermined amount of mesenchymal stem cells. The kit may be provided for use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The kit may be provided together with instructions for the administration of the HS8, FGF2 protein and/or mesenchymal stem cells separately, sequentially or simultaneously in order to provide the medical treatment.

In a further aspect of the present invention products are provided, the products containing therapeutically effective amounts of:
(i) HS8; and one or both of
(ii) FGF2 protein;
(iii) Mesenchymal stem cells,
for simultaneous, separate or sequential use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The products may optionally be formulated as a combined preparation for coadministration.

In one aspect of the present invention Heparan sulphate HS8 is provided for use in a therapeutic method of repair and/or regeneration of skin. In another aspect of the present invention the use of Heparan sulphate HS8 in the manufacture of a medicament for use in a therapeutic method of repair and/or regeneration of skin is provided. In another aspect of the present invention a therapeutic method of repair and/or regeneration of skin is provided, the method comprising administering heparan sulphate HS8 to a subject in need of treatment thereof.

In some embodiments the therapeutic method may involve treatment of a skin wound or scar, optionally selected from skin burns, ulcers, excisional wounds, cut, stab or puncture wounds. In some embodiments the therapeutic method may involve skin graft healing, skin reconstruction, or skin plastic surgery.

In another aspect of the present invention a method of healing a skin wound is provided, the method comprising contacting the skin wound with an effective amount of a pharmaceutical composition comprising HS8. In another aspect of the present invention heparan sulphate HS8 is provided for use in a method of healing a skin wound, the method comprising contacting the skin wound with an effective amount of a pharmaceutical composition comprising HS8. In another aspect of the present invention the use of heparan sulphate HS8 in the manufacture of a medicament for use in a method of healing a skin wound, the method comprising contacting the skin wound with an effective amount of a pharmaceutical composition comprising HS8 is provided.

In another aspect of the present invention a method of treating a subject having a skin wound is provided, the method comprising administration of a therapeutically effective amount of heparan sulphate HS8 to the subject leading to repair and/or regeneration of skin at the wound. In another aspect of the present invention heparan sulphate HS8 is provided for use in a method of treating a subject having a skin wound, the method comprising administration of a therapeutically effective amount of heparan sulphate HS8 to the subject leading to repair and/or regeneration of skin at the wound. In another aspect of the present invention the use of heparan sulphate HS8 in the manufacture of a medicament for use in a method of treating a subject having a skin wound, the method comprising administration of a therapeutically effective amount of heparan sulphate HS8 to the subject leading to repair and/or regeneration of skin at the wound, is provided.

In some embodiments the skin wound is a skin burn, ulcer, excisional wound, cut, stab or puncture wound In another aspect of the present invention a method of skin grafting, skin reconstruction, or skin plastic surgery is provided, the method comprising contacting the skin at or adjacent the region of grafting, reconstruction or plastic surgery with an effective amount of a pharmaceutical composition comprising HS8. In another aspect of the present invention heparan sulphate HS8 is provided for use in a method of skin grafting, skin reconstruction, or skin plastic surgery, the method comprising contacting the skin at or adjacent the region of grafting, reconstruction or plastic surgery with an effective amount of a pharmaceutical composition comprising HS8. In another aspect of the present invention the use of heparan sulphate HS8 in the manufacture of a medicament for use in a method of skin grafting, skin reconstruction, or skin plastic surgery, the method comprising contacting the skin at or adjacent the region of grafting, reconstruction or plastic surgery with an effective amount of a pharmaceutical composition comprising HS8.

In another aspect of the present invention HS8 is provided for use in a method of scarless wound healing in skin. In another aspect of the present invention the use of HS8 in the manufacture of a medicament for use in a method of scarless wound healing in skin is provided. In another aspect of the present invention a method of scarless wound healing in skin is provided, the method comprising administering heparan sulphate HS8 to a subject in need of treatment thereof.

In another aspect of the present invention a method for treating a dermal or epidermal wound in a subject is provided, the method comprising administering to the subject a pharmaceutical composition comprising HS8. In another aspect of the present invention heparan sulphate HS8 is provided for use in a method for treating a dermal or epidermal wound in a subject. In another aspect of the present invention, the use of heparan sulphate HS8 in the manufacture of a medicament for use in a method for treating a dermal or epidermal wound in a subject is provided.

In some embodiments HS8, or medicaments or pharmaceutical compositions containing HS8 may be formulated for topical or transdermal administration. In some embodiments HS8, or medicaments or pharmaceutical compositions containing may be formulated as a gel, spray, paste, ointment, cream, lotion, salve, oil, aqueous solution, suspension, dispersion, patch, adhesive plaster, bandage, dressing, depot, or reservoir.

In some embodiments, the method/treatment may further comprise administration of a growth factor, preferably FGF2, and/or mesenchymal stem cells. In some embodiments the HS8, or medicament or pharmaceutical composition is formulated as a combined preparation together with a growth factor, preferably FGF2, and/or with mesenchymal stem cells.

Further aspects of the present invention are set out below.

In one aspect of the present invention a GAG is provided having high binding affinity for FGF2. More preferably the GAG is a heparan sulphate (HS). In one embodiments the HS was isolated from a GAG mixture obtained from porcine intestinal mucosa (available from Celsus Laboratories Inc, Cincinnatti, USA, e.g. INW-08-045, Heparan Sulphate I, Celsus Lab Inc, HO-03102, HO-10595, 10×100 mg) by following the methodology described herein in which a polypeptide comprising the heparin-binding domain of FGF2 containing the amino acid sequence of YCKNGGF was attached to a solid support and GAG-polypeptide complexes were allowed to form. Dissociation of the GAG component from the GAG-polypeptide complexes led to isolation of a unique HS herein called "HS8". In one embodiment, HS8 is the HS isolated by attaching the polypeptide GHFKDPKRLYCKNGGF (SEQ ID NO: 1) to a solid support, allowing GAG-polypeptide complexes to form, and dissociating the GAG component from the GAG-polypeptide complexes.

It is the inventors belief that HS8 can be obtained from HS fractions obtained from a plurality of sources, including mammalian (human and non-human) tissue and/or extracellular matrix.

Accordingly, in one aspect of the present invention HS8 is provided. HS8 may be provided in isolated or purified form. In another aspect culture media comprising HS8 is provided.

In yet another aspect of the present invention a pharmaceutical composition or medicament comprising HS8 is provided, optionally in combination with a pharmaceutically acceptable carrier, adjuvant or diluent. In some embodiments pharmaceutical compositions or medicaments may further comprise FGF2 protein. Pharmaceutical compositions or medicaments comprising HS8 are provided for use in the prevention or treatment of injury or disease. The use of HS8 in the manufacture of a medicament for the prevention or treatment of injury or disease is also provided.

In a further aspect of the present invention, a method of preventing or treating injury or disease in a patient in need of treatment thereof is provided, the method comprising administering an effective amount of HS8 to the patient. The administered HS8 may be formulated in a suitable pharmaceutical composition or medicament and may further comprise a pharmaceutically acceptable carrier, adjuvant or diluent. Optionally, the pharmaceutical composition or medicament may also comprise FGF2 protein.

In another aspect of the present invention a method of promoting or inhibiting osteogenesis (the formation of bone cells and/or bone tissue) is provided comprising administering HS8 to bone precursor cells or bone stem cells.

In another aspect of the present invention a method of promoting or inhibiting the formation of cartilage tissue (chondrogenesis) is provided, comprising administering HS8 to cartilage precursor cells or cartilage stem cells.

The methods of stimulating or inhibiting osteogenesis or formation of cartilage tissue may be conducted in vitro by contacting bone or cartilage precursor or stem cells with HS8, optionally in the presence of exogenously added FGF2 protein. The precursor cells or stem cells may be mesenchymal stem cells. Where tissue formation is promoted, the tissue formed may be collected and used for implantation into a human or animal patient.

Accordingly, in one aspect of the present invention, connective tissue is provided wherein the connective tissue is obtained by in vitro culture of mesenchymal stem cells in the presence of HS8 (i.e. exogenous HS8), and optionally in the presence of FGF2 (i.e. exogenous FGF2). The connective tissue may be bone, cartilage, muscle, fat, ligament or tendon.

The prevention or treatment of disease using HS8 may involve the repair, regeneration or replacement of tissue, particularly connective tissue such as bone, cartilage, muscle, fat, ligament or tendon.

In patients having a deterioration of one of these tissues, administration of HS8 to the site of deterioration may be used to stimulate the growth, proliferation and/or differentiation of tissue at that site. For example, stimulation of mesenchymal stem cells present at, or near to, the site of administration may lead, preferably when FGF2 is also present at the site, to the proliferation and differentiation of the mesenchymal stem cells into the appropriate connective tissue, thereby providing for replacement/regeneration of the damaged tissue and treatment of the injury.

Alternatively, connective tissue obtained from in vitro culture of mesenchymal stem cells in contact with HS8 may be collected and implanted at the site of injury or disease to replace damaged or deteriorated tissue. The damaged or deteriorated tissue may optionally first be excised from the site of injury or disease.

In another aspect, a pharmaceutical composition may be provided containing stem cells, preferably mesenchymal stem cells, and HS8. Administration, e.g. injection, of the composition at the site of injury, disease or deterioration provides for the regeneration of tissue at the site.

Accordingly, HS8 is useful in wound healing in vivo, including tissue repair, regeneration and/or replacement (e.g. healing of scar tissue or a broken bone) effected by direct application of HS8, optionally in combination with FGF2 and/or stem cells, to the patient requiring treatment. HS8 is also useful in the in vitro generation of tissue suitable for implantation into a patient in need of tissue repair, regeneration and/or replacement.

As shown herein, HS8 has the property of stabilising FGF2, and thereby prolonging its action. HS8 prevents FGF2 from degradation in culture medium (FIG. 46). This can be usefully applied to the storage of FGF2 preparations and the preparation of FGF2 containing culture media.

As such, in one aspect of the present invention a composition comprising a growth factor and isolated HS8 is provided. The growth factor may be a protein growth factor, and is preferably FGF2. The composition may comprise isolated FGF2 and isolated HS8. In some embodiments the composition may be a culture media. In other embodiments the composition may be a pharmaceutical composition or medicament containing FGF2.

The composition may be an FGF2 preparation comprising FGF2 and isolated HS8 in a container. A suitable container may be a bottle, vial, tube or syringe.

A method of increasing the stability of a growth factor is also provided, the method comprising contacting a growth factor with isolated HS8.

The stability of the growth factor may be measured in terms of its half-life, i.e. the amount of time taken for half of the growth factor in a given composition to be degraded and/or lose its activity. The growth factor is preferably a protein growth factor, more preferably FGF2. HS8 acts to maintain and prolong FGF2 half-life. The method may involve contacting isolated HS8 with the growth factor (e.g. FGF2) in vitro, e.g. as part of preparation of a growth factor (e.g. FGF2) composition, its storage or transport. Alternatively, the method may involve contacting isolated HS8 with the growth factor (e.g. FGF2) in vivo, e.g. by administering isolated HS8 to tissue in which the growth factor (e.g. FGF2) [naturally occurring in the tissue or exogenously added to the tissue] is present.

The method may also comprise the step of adding exogenous growth factor (e.g. FGF2) to the tissue.

The stability of FGF2 in a given composition or tissue that contains isolated HS8 (or to which isolated HS8 has been added) may be compared against a comparable composition not containing HS8 (or to which isolated HS8 has not been added.

In the composition and method described above the HS8 may be purified, as described herein. The FGF2 may be isolated and/or purified, non-isolated or partially isolated, e.g. part of an extracellular matrix material, or present in a composition of cells. Isolated or purified FGF2 may be recombinant FGF2. Recombinant FGF2 is commercially available from a number of manufacturers such as Peprotech; Merck Millipore, MA; Life Technologies Corporation; Gibco; and Invitrogen.

Optionally, aspects and embodiments of the present do not include HS1 or HS2 (as described by Brickman et al (Glycobiology Vo. 8 No. 5 pp. 463-471, 1998 and in WO2010/011185). In some embodiments heparan sulphates according to the present invention do not include HS2, and/or a heparan sulphate having a nitrous acid disaccharide digestion profile according to FIG. 29 and/or a heparan sulphate having a nitrous acid disaccharide digestion profile according to FIG. 30.

The following numbered paragraphs contain statements of broad combinations of the inventive technical features herein disclosed:

1. Heparan sulphate HS8.

2. Heparan sulphate HS8 in isolated or substantially purified form.

3. Heparan sulphate HS8 according to paragraph 1 or 2 wherein the HS8 is capable of binding a peptide or polypeptide having, or consisting of, the amino acid sequence YCKNGGF (SEQ ID NO:2).

4. Heparan sulphate HS8 according to paragraph 3 wherein the peptide or polypeptide has, or consists of, the amino acid sequence GHFKDPKRLYCKNGGF (SEQ ID NO:1).

5. Isolated or substantially purified heparan sulphate HS8 according to any one of paragraphs 1 to 4, wherein following digestion with heparin lyases I, II and III and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0 |

6. Isolated or substantially purified heparan sulphate HS8 according to any one of paragraphs 1 to 4, wherein following digestion with heparin lyases I, II and III and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 1.0 |
| ΔUA,2S-GlcNS | 7.2 ± 0.4 |
| ΔUA-GlcNS,6S | 15.5 ± 1.0 |
| ΔUA,2S-GlcNAc,6S | 6.5 ± 0.6 |
| ΔUA-GlcNS | 15.7 ± 3.0 |

-continued

| Disaccharide | Normalised weight percentage |
|---|---|
| ΔUA,2S-GlcNAc | 1.0 ± 0.4 |
| ΔUA-GlcNAc,6S | 8.9 ± 1.0 |
| ΔUA-GlcNAc | 32.5 ± 1.6 |

7. Heparan sulphate HS8, or heparan sulphate HS8 in isolated or substantially purified form, according to any one of paragraphs 1 to 6 obtained by a method comprising:
(i) providing a solid support having polypeptide molecules adhered to the support, wherein the polypeptide comprises a heparin-binding domain having the amino acid sequence YCKNGGF;
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

8. The method of paragraph 7 wherein the polypeptide has, or consists of, the amino acid sequence selected from GHFKDPKRLYCKNGGF (SEQ ID NO:1).

9. The method of paragraph 7 or 8 wherein the mixture comprising glycosaminoglycans is a heparan sulphate preparation obtained from porcine intestinal mucosa.

10. A composition comprising heparan sulphate HS8 according to any one of paragraphs 1 to 9.

11. The composition of paragraph 10, further comprising a growth factor, preferably FGF2.

12. A pharmaceutical composition or medicament comprising heparan sulphate HS8 according to any one of paragraphs 1 to 9.

13. The pharmaceutical composition or medicament of paragraph 12 wherein the pharmaceutical composition or medicament further comprises FGF2 protein and/or mesenchymal stem cells.

14. The pharmaceutical composition or medicament of paragraph 12 or 13 for use in a method of medical treatment.

15. Heparan sulphate HS8 according to any one of paragraphs 1 to 9 for use in a method of medical treatment.

16. Heparan sulphate HS8 according to paragraph 15 wherein the method of medical treatment comprises a method of wound healing in vivo.

17. Heparan sulphate HS8 according to paragraph 15 wherein the method of medical treatment comprises the repair and/or regeneration of tissue, preferably bone tissue.

18. Use of Heparan sulphate HS8 according to any one of paragraphs 1 to 9 in the manufacture of a medicament for the treatment of a disease, condition or injury to tissue, wherein the method involves the repair and/or regeneration of tissue, preferably bone tissue.

19. A method of treating a disease, condition or injury to tissue in a patient, the method comprising administration of a therapeutically effective amount of heparan sulphate HS8 to the patient leading to repair and/or regeneration of the tissue, preferably bone tissue.

20. The method of paragraph 19 wherein the method comprises administering heparan sulphate HS8 to tissue at or surrounding a wound or location on the patient's body at which regeneration or repair of tissue is required.

21. The method of paragraph 19 or 20 wherein the method further comprises administering FGF2 protein to the patient.

22. A method of treating a disease, condition or injury to tissue in a patient, the method comprising surgically implanting a biocompatible implant or prosthesis, which implant or prosthesis comprises a biomaterial and heparan sulphate HS8 according to any one of paragraphs 1 to 9, into tissue of the patient at or surrounding the site of the disease, condition or injury leading to repair and/or regeneration of the tissue.

23. A biocompatible implant or prosthesis comprising a biomaterial and heparan sulphate HS8 according to any one of paragraphs 1 to 9.

24. A method of forming a biocompatible implant or prosthesis, the method comprising the step of coating or impregnating a biomaterial with heparan sulphate HS8 according to any one of paragraphs 1 to 9.

25. A method of treating a bone fracture in a patient, the method comprising administration of a therapeutically effective amount of heparan sulphate HS8 according to any one of paragraphs 1 to 9 to the patient.

26. The method of paragraph 25 wherein the method comprises administering said heparan sulphate HS8 to the tissue surrounding the fracture.

27. The method of paragraph 25 wherein administration of said heparan sulphate HS8 comprises injection of the heparan sulphate to the tissue surrounding the fracture.

28. The method of any one of paragraphs 25 to 27 wherein said heparan sulphate is formulated as a pharmaceutical composition or medicament comprising the heparan sulphate and a pharmaceutically acceptable carrier, adjuvant or diluent.

29. A method of treating a bone fracture in a patient, the method comprising surgically implanting a biocompatible implant or prosthesis, which implant or prosthesis comprises a biomaterial and a therapeutically effective amount of heparan sulphate HS8 according to any one of paragraphs 1 to 9 into tissue of the patient at or surrounding the site of fracture.

36. A kit of parts, the kit comprising a predetermined amount of heparan sulphate HS8 according to any one of paragraphs 1 to 9 and a predetermined amount of FGF2.

37. Products containing therapeutically effective amounts of:
(i) Heparan sulphate HS8 according to any one of paragraphs 1 to 9; and one or both of
(ii) FGF2 protein;
(iii) Mesenchymal stem cells, for simultaneous, separate or sequential use in a method of medical treatment.

38. A method of increasing the stability of a growth factor, preferably FGF2, the method comprising contacting a growth factor, preferably FGF2, with heparan sulphate HS8 according to any one of paragraphs 1 to 9.

DESCRIPTION OF PREFERRED EMBODIMENTS

The inventors have identified a novel class of heparan sulphate molecules, called HS8. They have shown that HS8 has the following advantageous properties:
HS8 enriches for mesenchymal stem cells (MSCs) expressing STRO1 (FIG. 12, FIG. 14);
HS8 results in increased growth of STRO-1+ve affinity isolated MSCs and MSCs isolated by adherence to plastic (FIGS. 17, 18, 19, 20).
In contrast to heparan sulphate that lacks HS8 (HS8−ve fraction) HS8 enriches for a population of human MSCs that have a surface marker expression pattern that is consistent with the internationally recognised definition of human MSCs (FIG. 22);

Culture of hMSCs with HS8 provides a human MSC population that has a high level of expression of CD49a, SSEA-4 and STRO-1 (FIG. 22). In contrast the addition of FGF-2 as a culture supplement to hMSCs negatively influences the proportion of hMSCs that express STRO-1 and results in a loss of multipotentiality of hMSCs (FIGS. 22, 23 and 25).

HS8 increases CFU-F formation;
HS8 enhances FGF-2 mediated MSC growth (FIG. 26);
HS8 sustains FGF2 mediated signalling of the ERK pathway.
HS8 promotes proliferation of mesenchymal stem cells (FIGS. 42 and 43)

HS8

The present invention relates to a class of heparan sulphate molecule called HS8. HS8 molecules are obtainable by methods of enriching mixtures of compounds containing one or more GAGs that bind to a polypeptide corresponding to a heparin-binding domain of FGF2. In particular, HS8 molecules can be obtained by enriching for heparan sulphate that binds to a heparin binding domain of FGF2 which domain comprises, or consists of, the amino acid sequence YCKNGGF. The enrichment process may be used to isolate HS8.

The present invention also relates to mixtures of compounds enriched with HS8, and methods of using such mixtures.

In addition to being obtainable by the methodology described here, HS8 can also be defined functionally and structurally.

Functionally, an HS8 is capable of binding a peptide having, or consisting of, the amino acid sequence of YCKNGGF (SEQ ID NO:2). The peptide may contain one or more additional amino acids on one or both ends of the peptide. By way of example, the peptide may be GHFKDPKRLYCKNGGF (SEQ ID NO:1).

Preferably, HS8 binds the peptide with a $K_D$ of less than 100 µM, more preferably less than one of 50 µM, 40 µM, 30 µM, 20 µM, or 10 µM.

Preferably, HS8 also binds FGF2 protein with a $K_D$ of less than 100 µM, more preferably less than one of 50 µM, 40 µM, 30 µM, 20 µM, or 10 µM. Binding between HS8 and FGF2 protein may be determined by the following assay method.

FGF2 is dissolved in Blocking Solution (0.2% gelatin in SAB) at a concentration of 3 µg/ml and a dilution series from 0-3 µg/ml in Blocking Solution is established. Dispensing of 200 µl of each dilution of FGF2 into triplicate wells of Heparin/GAG Binding Plates pre-coated with heparin; incubated for 2 hrs at 37° C., washed carefully three times with SAB and 200 µl of 250 ng/ml biotinylated anti-FGF2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as FGF2 protein in the absence of added heparan sulphate, or FGF2 protein to which an heparan sulphate is added that does not bind FGF2 protein.

The binding of HS8 is preferably specific, in contrast to non-specific binding and in the context that the HS8 can be selected from other heparan sulphates and/or GAGs by a method involving selection of heparan sulphates exhibiting a high affinity binding interaction with the peptide comprising YCKNGGF such as SEQ ID NO:1, or with FGF2 protein.

HS8 according to the present invention preferably increases proliferation of stem cells whilst maintaining their pluripotency or multipotency.

The disaccharide composition of HS8 following digestion with heparin lyases I, II and III to completion and then subjecting the resulting disaccharide fragments to capillary electrophoresis analysis is shown in FIGS. 44 and 45.

HS8 according to the present invention includes heparan sulphate that has a disaccharide composition within ±10% (more preferably ±one of 9%, 8%, 7%, 6%, 5%, 4%, 3%, 2%, 1% or 0.5%) of the normalised percentage values shown for each disaccharide in FIG. 45 for the HS8 retained species or in FIG. 44 for the HS8 retained species, as determined by digestion with heparin lyases I, II and III to completion and then subjecting the resulting disaccharide fragments to capillary electrophoresis analysis.

The disaccharide composition of HS8 as determined by digestion with heparin lyases I, II and III to completion and then subjecting the resulting disaccharide fragments to capillary electrophoresis analysis may have a disaccharide composition according to any one of the following:

| Disaccharide | Normalised weight percentage |
|---|---|
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0 |
| ΔUA,2S-GlcNS,6S | 12.7 ± 2.0 |
| ΔUA,2S-GlcNS | 7.2 ± 2.0 |
| ΔUA-GlcNS,6S | 15.5 ± 2.0 |
| ΔUA,2S-GlcNAc,6S | 6.5 ± 2.0 |
| ΔUA-GlcNS | 15.7 ± 2.0 |
| ΔUA,2S-GlcNAc | 1.0 ± 0.5 |
| ΔUA-GlcNAc,6S | 8.9 ± 2.0 |
| ΔUA-GlcNAc | 32.5 ± 2.0 |
| ΔUA,2S-GlcNS,6S | 12.7 ± 2.0 |
| ΔUA,2S-GlcNS | 7.2 ± 1.0 |
| ΔUA-GlcNS,6S | 15.5 ± 2.0 |
| ΔUA,2S-GlcNAc,6S | 6.5 ± 1.0 |
| ΔUA-GlcNS | 15.7 ± 2.0 |
| ΔUA,2S-GlcNAc | 1.0 ± 0.5 |
| ΔUA-GlcNAc,6S | 8.9 ± 2.0 |
| ΔUA-GlcNAc | 32.5 ± 3.0 |
| ΔUA,2S-GlcNS,6S | 12.7 ± 1.0 |
| ΔUA,2S-GlcNS | 7.2 ± 0.4 |
| ΔUA-GlcNS,6S | 15.5 ± 1.0 |
| ΔUA,2S-GlcNAc,6S | 6.5 ± 0.6 |
| ΔUA-GlcNS | 15.7 ± 3.0 |
| ΔUA,2S-GlcNAc | 1.0 ± 0.4 |
| ΔUA-GlcNAc,6S | 8.9 ± 1.0 |
| ΔUA-GlcNAc | 32.5 ± 1.6 |
| ΔUA,2S-GlcNS,6S | 12.7 ± 0.75 |
| ΔUA,2S-GlcNS | 7.2 ± 0.3 |
| ΔUA-GlcNS,6S | 15.5 ± 0.75 |
| ΔUA,2S-GlcNAc,6S | 6.5 ± 0.45 |
| ΔUA-GlcNS | 15.7 ± 2.25 |
| ΔUA,2S-GlcNAc | 1.0 ± 0.3 |
| ΔUA-GlcNAc,6S | 8.9 ± 0.75 |
| ΔUA-GlcNAc | 32.5 ± 1.2 |
| ΔUA,2S-GlcNS,6S | 12.7 ± 0.5 |
| ΔUA,2S-GlcNS | 7.2 ± 0.2 |
| ΔUA-GlcNS,6S | 15.5 ± 0.5 |

-continued

| Disaccharide | Normalised weight percentage |
| --- | --- |
| ΔUA,2SGlcNAc,6S | 6.5 ± 0.3 |
| ΔUA-GlcNS | 15.7 ± 1.5 |
| ΔUA,2S-GlcNAc | 1.0 ± 0.2 |
| ΔUA-GlcNAc,6S | 8.9 ± 0.5 |
| ΔUA-GlcNAc | 32.5 ± 0.8 |

In preferred embodiments the total weight percentage of the 8 disaccharides listed is 100% (optionally ±3.0% or less, or ±2.0% or less, ±1.0% or less, ±0.5% or less).

Comparison of HS8 with an HS isolated as having high affinity for the growth factor BMP2, called HS3 (described in WO2010/030244) reveals that the structural dissimilarity of HS8 compared to HS3 is characterised by the amount of the following disaccharides: ΔUA-GlcNS,6S and ΔUA-GlcNS. In particular HS8 has a greater percentage composition of ΔUA-GlcNS,6S than HS3 and a lower percentage composition of ΔUA-GlcNS than HS3.

As such, HS8 may be characterised by having a percentage composition of ΔUA-GlcNS,6S of 15.5±4.0 or less, or ±3.5 or less, or ±3.0 or less, or ±2.5 or less, or ±2.0 or less, ±1.5 or less, or ±1.0 or less, or ±0.5 or less, or ±0.25 or less, or ±0.1 or less. HS8 may additionally or alternatively be characterised by having a percentage composition of ΔUA-GlcNS of 15.7±4.0 or less, or ±3.5 or less, or ±3.0 or less, or ±2.5 or less, or ±2.0 or less, or ±1.5 or less, or ±1.0 or less, or ±0.5 or less, or ±0.25 or less, or ±0.1 or less.

HS8 may also be characterised by having a percentage composition of ΔUA,2S-GlcNS,6S of 12.7±1.5 or less, ±1.0 or less, or ±0.5 or less, or ±0.25 or less, or ±0.1 or less.

HS8 may also be characterised by having a percentage composition of ΔUA,2S-GlcNS of 7.2 or ±2.0 or less, ±1.5 or less, ±1.0 or less, or ±0.5 or less, or ±0.25 or less, or ±0.1 or less.

HS8 may also be characterised by having a percentage composition of ΔUA,2S-GlcNAc,6S of 6.5±1.5 or less, ±1.0 or less, or ±0.5 or less, or ±0.25 or less, or ±0.1 or less.

HS8 may also be characterised by having a percentage composition of ΔUA-GlcNAc,6S of 8.9±0.5 or less, or ±0.25 or less, or ±0.1 or less.

In these embodiments the percentage composition of the remaining disaccharide components may be as listed above, or as shown in FIG. 44 or 45±one of 10%, 9%, 8%, 7%, 6%, 5%, 4%, 3%, 2%, 1% or 0.5%.

Digestion of HS8 with heparin lyases I, II and III and/or capillary electrophoresis analysis of disaccharides is preferably performed in accordance with Example 18.

Digestion of HS preparations with heparin lyase enzymes may be conducted as follows: HS preparations (1 mg) are each dissolved in 500 μL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 μL water and an aliquot (50 μL) is taken for analysis.

Capillary electrophoresis (CE) of disaccharides from digestion of HS preparations may be conducted as follows: capillary electrophoresis operating buffer is made by adding an aqueous solution of 20 mM $H_3PO_4$ to a solution of 20 mM $Na_2HPO_4.12H_2O$ to give pH 3.5; column wash is 100 mM NaOH (diluted from 50% w/w NaOH); operating buffer and column wash are both filtered using a filter unit fitted with 0.2 μm cellulose acetate membrane filters; stock solutions of disaccharide Is (e.g. 12) are prepared by dissolving the disaccharides in water (1 mg/mL); calibration curves for the standards are determined by preparing a mix containing all standards containing 10 μg/100 μL of each disaccharide and a dilution series containing 10, 5, 2.5, 1.25, 0.625, 0.3125 μg/100 μL is prepared; including 2.5 μg of internal standard (ΔUA,2S-GlcNCOEt,6S). The digests of HS are diluted (50 μL/mL) with water and the same internal standard is added (2.5 μg) to each sample. The solutions are freeze-dried and re-suspended in water (1 mL). The samples are filtered using PTFE hydrophilic disposable syringe filter units.

Analyses are performed using a capillary electrophoresis instrument on an uncoated fused silica capillary tube at 25° C. using 20 mM operating buffer with a capillary voltage of 30 kV. The samples are introduced to the capillary tube using hydrodynamic injection at the cathodic (reverse polarity) end. Before each run, the capillary is flushed with 100 mM NaOH (2 min), with water (2 min) and pre-conditioned with operating buffer (5 min). A buffer replenishment system replaces the buffer in the inlet and outlet tubes to ensure consistent volumes, pH and ionic strength are maintained. Water only blanks are run at both the beginning, middle and end of the sample sequence. Absorbance is monitored at 232 nm. All data is stored in a database and is subsequently retrieved and re-processed. Duplicate or triplicate digests/analyses may be performed and the normalized percentage of the disaccharides in the HS digest is calculated as the mean average of the results for the analyses.

In some embodiments HS8 has an average (mean) molecular weight in the range 18 to 27 kDa. In some embodiments this may be one of 20 to 25 kDa, 21 to 25 kDa, 21 to 24 kDa, 21 to 23 kDa, 20 to 24 kDa, 20 to 23 kDa, or 20 to 22 kDa.

In some embodiments an HS8 chain comprises at least 25 disaccharide units. In some embodiments this may be one of at least 26 disaccharides, at least 27 disaccharides, at least 28 disaccharides, at least 29 disaccharides, at least 30 disaccharides, at least 31 disaccharides, at least 32 disaccharides, at least 33 disaccharides, at least 34 disaccharides, at least 35 disaccharides, at least 36 disaccharides, at least 37 disaccharides, at least 38 disaccharides, at least 39 disaccharides, at least 40 disaccharides, at least 41 disaccharides, at least 42 disaccharides, at least 43 disaccharides, or at least 44 disaccharides.

To identify HS8 the inventors used a method that involves enriching for glycosaminoglycan molecules that exhibit binding to particular polypeptides having a heparin-binding domain. Isolated GAG mixtures and/or molecules can then be identified and tested for their ability to modulate the growth and differentiation of cells and tissue expressing a protein containing the heparin-binding domain. This enables the controlled analysis of the effect of particular GAG saccharide sequences on the growth and differentiation of cells and tissue, both in vitro and in vivo. This methodology is described in PCT/GB2009/000469 (WO2010/030244), incorporated herein by reference. The inventors applied this methodology to Fibroblast Growth Factor 2 (FGF2) in order to isolate and characterise GAGs having high binding to FGF2

Accordingly, to identify HS8 the inventors provided a method of isolating glycosaminoglycans capable of binding to proteins having heparin/heparan-binding domains, the method comprising:

(i) providing a solid support having polypeptide molecules adhered to the support, wherein the polypeptide comprises a heparin-binding domain;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes;

(v) collecting the dissociated glycosaminoglycans.

The inventors also provided isolated glycosaminoglycans identified by their ability to modulate the growth or differentiation of cells or tissues. To do this, they provided a method of identifying glycosaminoglycans capable of stimulating or inhibiting the growth and/or differentiation of cells and/or tissues, the method comprising:

(i) providing a solid support having polypeptide molecules adhered to the support, wherein the polypeptide comprises a heparin-binding domain;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes;

(v) collecting the dissociated glycosaminoglycans;

(vi) adding the collected glycosaminoglycans to cells or tissues in which a protein containing the amino acid sequence of the heparin-binding domain is present;

(vii) measuring one or more of: proliferation of the cells, differentiation of the cells, expression of one or more protein markers.

The inventors used these methods to identify a GAG capable of binding to FGF2 (which they called HS8), wherein the polypeptide used in the inventors' methodology comprised the heparin-binding domain of GHFKDPKRLY-CKNGGF (SEQ ID NO:1).

In the inventors' methodology, the mixture comprising GAGs may contain synthetic glycosaminoglycans. However, GAGs obtained from cells or tissues are preferred. For example, the mixture may contain extracellular matrix wherein the extracellular matrix material is obtained by scraping live tissue in situ (i.e. directly from the tissue in the body of the human or animal from which it is obtained) or by scraping tissue (live or dead) that has been extracted from the body of the human or animal. Alternatively, the extracellular matrix material may be obtained from cells grown in culture. The extracellular matrix material may be obtained from connective tissue or connective tissue cells, e.g. bone, cartilage, muscle, fat, ligament or tendon. In one embodiment commercially available heparan sulphate from Porcine Mucosa (Celsus HS) was used.

The GAG component may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulphation of the GAG can also be determined and used to determine GAG structure. For example, for heparan sulphate the pattern of sulphation at amino sugars and at the C2, C3 and C6 positions may be used to characterise the heparan sulphate.

Disaccharide analysis, tetrasaccharide analysis and analysis of sulphation can be used in conjunction with other analytical techniques such as HPLC, mass spectrometry and NMR which can each provide unique spectra for the GAG. In combination, these techniques may provide a definitive structural characterisation of the GAG.

For example, the 1H NMR spectra of HS8, in comparison with Celsus HS (from which HS8 was derived) and HS3 (a BMP2 binding HS) is shown in FIGS. 31 and 32. HS8 according to the present invention may have a $1^H$ NMR spectra corresponding to the HS8 spectra of FIG. 31 or 32. In some embodiments HS8 according to the present invention may have a 1H NMR spectra in which the spectra at 4.0-3.5 ppm corresponds to that of HS8 in FIG. 32 (top line between 3.8-3.7 ppm). In some embodiments HS8 according to the present invention may have a peak at about 3.8 ppm and/or a peak at about 3.7 ppm. In some embodiments HS8 can be distinguished from other HS8 by its unique methine and/or methylene $1^H$ NMR spectra, e.g. as shown in FIG. 32.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide complexes may be subjected to treatment with an agent that lyses glycosaminoglycan chains, e.g. a lyase. Lyase treatment may cleave portions of the bound GAG that are not taking part in the binding interaction with the polypeptide. Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulphation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased. GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

The GAGs identified preferably exhibit a functional effect when contacted with cells or tissue in which a protein containing the heparin-binding domain is expressed or contained. The functional effect may be a modulating or potentiating effect.

The functional effect may be to promote (stimulate) or inhibit the proliferation of the cells of a certain type or the differentiation of one cell type into another, or the expression of one or more protein markers. For example, the GAGs may promote cell proliferation, i.e. an increase in cell number, or promote differentiation of stem cells into specialised cell types (e.g. mesenchymal stem cells in connective tissue), promote or inhibit the expression of protein markers indicative of the multipotency or differentiation state of the cells (e.g. markers such as alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Coll2a) and SOX9).

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes the heparin-binding domain and optionally including one or more amino acids at one or each of the N- and C-terminals of the peptides. These additional amino acids may enable the addition of linker or attachment molecules to the polypeptide that are required to attach the polypeptide to the solid support.

In preferred embodiments of the inventors' methodology, in addition to the number of amino acids in the heparin-binding domain the polypeptide contains 1-20, more preferably 1-10, still more preferably 1-5 additional amino acids. In some embodiments the amino acid sequence of the heparin-binding domain accounts for at least 80% of the amino acids of the polypeptide, more preferably at least 90%, still more preferably at least 95%. In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is FGF2. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

In this specification the protein is FGF2. The amino acid sequences of the preferred heparin-binding domains is GHFKDPKRLYCKNGGF (SEQ ID NO:1) [which is found at amino acids 157-172 of human FGF2], or a sequence having the sequence YCKNGGF (SEQ ID NO:2).

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities. Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a specific manner to the polypeptide; those that bind in a non-specific manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected. GAGs may accordingly be obtained that have a high binding affinity for a protein of interest and/or the heparin-binding domain of the protein of interest. The binding affinity ($K_d$) may be chosen from one of: less than 10 µM, less than 1 µM, less than 100 nM, less than 10 nM, less than 1 nM, less than 100 µM.

GAGs obtained by the methods described may be useful in a range of applications, in vitro and/or in vivo. The GAGs may be provided for use in stimulation or inhibition of cell or tissue growth and/or proliferation and/or differentiation either in cell or tissue culture in vitro, or in cells or tissue in vivo.

The GAGs may be provided as a formulation for such purposes. For example, culture media may be provided comprising a GAG obtained by the method described, i.e. comprising HS8.

Cells or tissues obtained from in vitro cell or tissue culture in the presence of HS8 may be collected and implanted into a human or animal patient in need of treatment. A method of implantation of cells and/or tissues may therefore be provided, the method comprising the steps of:

(a) culturing cells and/or tissues in vitro in contact with HS8;
(b) collecting the cells and/or tissues;
(c) implanting the cells and/or tissues into a human or animal subject in need of treatment.

The cells may be cultured in part (a) in contact with HS8 for a period of time sufficient to allow growth, proliferation or differentiation of the cells or tissues. For example, the period of time may be chosen from: at least 5 days, at least 10 days, at least 20 days, at least 30 days or at least 40 days.

In another embodiment the HS8 may be formulated for use in a method of medical treatment, including the prevention or treatment of injury or disease. A pharmaceutical composition or medicament may be provided comprising HS8 and a pharmaceutically acceptable diluent, carrier or adjuvant. Such pharmaceutical compositions or medicaments may be provided for the prevention or treatment of injury or disease. The use of HS8 in the manufacture of a medicament for the prevention or treatment of injury or disease is also provided. Optionally, pharmaceutical compositions and medicaments according to the present invention may also contain the protein of interest (i.e. FGF2) having the heparin-binding domain to which the GAG binds. In further embodiments the pharmaceutical compositions and medicaments may further comprise stem cells, e.g. mesenchymal stem cells.

Treatment of injury or disease may comprise the repair, regeneration or replacement of cells or tissue, such as connective tissue (e.g. bone, cartilage, muscle, fat, tendon or ligament). For the repair of tissue, the pharmaceutical composition or medicament comprising HS8 may be administered directly to the site of injury or disease in order to stimulate the growth, proliferation and/or differentiation of new tissue to effect a repair of the injury or to cure or alleviate (e.g. provide relief to the symptoms of) the disease condition. The repair or regeneration of the tissue may be improved by combining stem cells in the pharmaceutical composition or medicament.

For the replacement of tissue, HS8 may be contacted with cells and/or tissue during in vitro culture of the cells and/or tissue in order to generate cells and/or tissue for implantation at the site of injury or disease in the patient. Implantation of cells or tissue can be used to effect a repair of the injured or diseased tissue in the patient by replacement of the injured or diseased tissue. This may involve excision of injured/diseased tissue and implantation of new tissue prepared by culture of cells and/or tissue in contact with HS8.

Pharmaceutical compositions and medicaments according to the present invention may therefore comprise one of:
(a) HS8;
(b) HS8 in combination with stem cells;
(c) HS8 in combination with a protein containing the heparin-binding domain bound by HS8 (e.g. SEQ ID NO:1);
(d) HS8 in combination with stem cells and a protein containing the heparin-binding domain bound by HS8 (e.g. SEQ ID NO:1);
(e) Tissues or cells obtained from culture of cells or tissues in contact with HS8.

HS8 may be used in the repair or regeneration of bodily tissue, especially bone regeneration, neural regeneration, skeletal tissue construction, the repair of cardio-vascular injuries and the expansion and self-renewal of embryonic and adult stem cells. Accordingly, HS8 may be used to prevent or treat a wide range of diseases and injuries, including osteoarthritis, cartilage replacement, broken bones of any kind (e.g. spinal disc fusion treatments, long bone breaks, cranial defects), critical or non-union bone defect regeneration.

The use of HS8 in the repair, regeneration or replacement of tissue may involve use in wound healing, e.g. acceleration of wound healing, healing of scar or bone tissue and tissue grafting.

In another aspect, the present invention provides a biological scaffold comprising HS8. In some embodiments, the biological scaffolds of the present invention may be used in orthopaedic, vascular, prosthetic, skin and corneal applications. The biological scaffolds provided by the present invention include extended-release drug delivery devices, tissue valves, tissue valve leaflets, drug-eluting stents, vascular grafts, wound healing or skin grafts and orthopaedic prostheses such as bone, ligament, tendon, cartilage and muscle. In a preferred embodiment of the present invention, the biological scaffold is a catheter wherein the inner (and/or outer) surface comprises one or more GAG compounds (including HS8) attached to the catheter.

In another aspect, the present invention provides one or more GAGs (including HS8) isolated by the method described for use as an adjuvant. The adjuvant may be an immune adjuvant.

In another aspect, the present invention provides pharmaceutically acceptable formulations comprising a mixture of compounds comprising one or more GAGs, said mixture being enriched with respect to HS8. In another aspect, the invention provides pharmaceutically acceptable formulations comprising:
(i) a mixture of compounds comprising one or more GAGs, said mixture being enriched with respect to HS8; and
(ii) FGF2,
for separate, simultaneous or sequential administration. In a preferred embodiment the formulation comprises the mixture of compounds comprising one or more GAGs, said mixture being enriched with respect to HS8 and FGF2 in intimate admixture, and is administered simultaneously to a patient in need of treatment.

In another aspect of the present invention a kit is provided for use in the repair, or regeneration of tissue, said kit comprising (i) a predetermined amount of HS8, and (ii) a predetermined amount of FGF2.

The compounds of the enriched mixtures of the present invention can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that the compounds of the enriched mixtures of the present invention which bear a carboxylic acid group may be delivered in the form of an administrable prodrug, wherein the acid moiety is esterified (to have the form —CO2R'). The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis. Medicaments and pharmaceutical compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the injury or disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Stem Cells

Cells contacted with HS8 include stem cells.

HS8 may be used in the proliferation and/or differentiation of stem cells, and/or the lineage-commitment of stem cells.

The stem cells cultured and described herein may be stem cells of any kind. They may be totipotent or multipotent (pluripotent). They may be embryonic or adult stem cells from any tissue and may be hematopoietic stem cells, neural stem cells or mesenchymal stem cells. Preferably they are adult stem cells.

In this specification, by stem cell is meant any cell type that has the ability to divide (i.e. self-renew) and remain totipotent or multipotent (pluripotent) and give rise to specialized cells.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Coll2a) and SOX9.

In some preferred embodiments the stem cells are mesenchymal stem cells (MSCs), e.g. capable of differentiation into connective tissue and/or bone cells such as chondrocytes, osteoblasts, myocytes and adipocytes.

Mesenchymal stem cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of the cells pluripotency.

Suitable mesenchymal stem cells may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES British Journal of Haematology 121(2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. Stem Cells Dev. 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

Mesenchymal stem cells are pluripotent (multipotent) progenitor cells with the ability to generate components of cartilage, bone, muscle, tendon, ligament, and fat. These primitive progenitors exist postnatally and exhibit stem cell characteristics, namely low incidence and extensive renewal potential. These properties in combination with their developmental plasticity have generated tremendous interest in their potential use to replace damaged tissues. In essence these stem cells could be cultured to expand their numbers then transplanted to the injured site or after seeding in/on scaffolds to generate appropriate tissue constructs.

Thus, an alternative approach for skeletal, muscular, tendon, ligament and blood repair/regeneration is the selection, expansion and modulation of the appropriate progenitor cells such as osteoprogenitor cells (e.g. mesenchymal stem cells, chondrocytes, osteoblasts, myoblasts, bone stem cells or bone precursor cells) in the case of bone in combination with a conductive or inductive scaffolds to support and guide regeneration together with judicious selection of specific tissue growth factors.

The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Preferably they are human. Optionally they are non-human. Optionally they are non-embryonic stem cells. Optionally they are not totipotent.

In yet a further aspect of the present invention, a pharmaceutical composition comprising stem cells or other cells generated by any of the methods of the present invention, or fragments or products thereof, is provided. The pharmaceutical composition may be useful in a method of medical treatment. Suitable pharmaceutical compositions may further comprise a pharmaceutically acceptable carrier, adjuvant or diluent.

In another aspect of the present invention, stem cells or other cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells and other cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Mesenchymal Stem Cells

Mesenchymal stem cells (MSCs) were originally isolated from the bone marrow and are present as only 1 in 104-105 total bone marrow mononuclear cells (BMMNC) (Friedenstein et al. 1966). These cells are capable of producing colonies derived from single cell precursors, dubbed the CFU-F (colony forming unit fibroblast) population. MSCs have now been identified in many other tissues including adipose tissue (Gimble and Guilak 2003; Zuk et al. 2001), umbilical cord blood (Bieback et al. 2004; Erices et al. 2000;

Goodwin et al. 2001; Kogler et al. 2004; Wagner et al. 2005) and muscle (Jiang et al. 2002).

The minimal criteria for multipotent human mesenchymal stromal cells (MSC) has been set out by the Internation Society for Cellular Therapy (Dominici et al Cytotherapy (2006) Vol. 8, No. 4, 315-317). They propose three criteria to define human MSC: adherence to plastic, specific surface antigen expression and multipotent differentiation potential. In particular they stated that "First, MSC must be plastic-adherent when maintained in standard culture conditions using tissue culture flasks. Second, ≥95% of the MSC population must express CD105, CD73 and CD90, as measured by flow cytometry. Additionally, these cells must lack expression (≤2% positive) of CD45, CD34, CD14 or CD11b, CD79a or CD19 and HLA class II (HLA-DR). Third, the cells must be able to differentiate to osteoblasts, adipocytes and chondroblasts under standard in vitro differentiating conditions."

Dominici et al also stated that the biologic property that most uniquely identifies MSC is their capacity for trilineage mesenchymal differentiation into osteoblasts, adipocytes and chondroblasts using standard in vitro tissue culture-differentiating conditions. They confirmed that differentiation to osteoblasts can be demonstrated by staining with Alizarin red or von Kossa staining, adipocyte differentiation can most readily be demonstrated by starining with Oil red O and chdroblast differentiation can be demonstrated by staining with Alcian bluse or immunohistochemical staining for collage type II. Dominici et al state that kits for such assays are commercially available and that demonstrating differentiation should be feasible for all investigators.

Dominici et al also recognise that novel surface markers may be identified in the future that could also be used to define human MSCs. Three such markers are now known: CD49a, SSEA-4 and STRO-1.

Rider et al reported that CD49a+ clones have enhanced expression of CD90 and CD105 compared to unsorted cells and demonstrated that CD49a+ clones readily underwent multilineage differentiation into fat, bone and cartilage compared to unsorted cells, supporting the use of alpha-1 integrin (CD49a) selection for the enrichment of mesenchymal stem cells and provided a strategy for selecting the most multipotential cells from a heterogenous pool of bone marrow mononuclear stem cells (Rider et al. J. Mol. Hist (2007) 38:449-458). Rider et al also report that CFU-F cells are associated with the expression of CD49a, that CD49a expressing CFU-F cells also co-express STRO-1, and CD49a can be used to isolate MSCs from rats and mice in addition to humans indicating that it may be conserved marker for enrichment.

Gang et al report that the stage specific embryonic antigen SSEA-4, commonly used as a marker for undifferentiated pluripotent human embryonic stem cells and cleavage to blastocyst stage embryos also identifies the adult human mesenchymal stem cell population and can be used to isolate MSCs (Gang et al., Blood 2007; 109:1743-1751). Gang et al also describe the use of a monoclonal antibody that binds the surface marker STRO-1 in the enrichment of clonogenic stromal cells (CFU-F)—so-called STRO-1$^{+bright}$.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate.

As used herein, the term 'GAG' also extends to encompass those molecules that are GAG conjugates. An example of a GAG conjugate is a proteoglycosaminoglycan (PGAG, proteoglycan) wherein a peptide component is covalently bound to an oligosaccharide component.

Heparan Sulphate (HS)

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

Use of HS8 in the Repair and/or Regeneration of Skin

We have developed a purified HS preparation, HS8 described herein, that is more specifically targeted at FGF-2. We have shown it possesses an increased affinity for FGF-2, increases the growth rates of human dermal fibroblasts, and triggers the scratch wound assay response of both keratinocytes and dermal fibroblasts. HS8 will be trialed as an adjuvant that induces the repair of skin after trauma, burns, ulceration or disease. HS8 will be trialed as an adjuvant that both stabilizes and reduces the amounts of growth factor required to treat chronic wounds of the skin, including full thickness, excisional wounds. HS8 thus provides a useful therapeutic tool for the treatment of non-healing skin wounds such as diabetic ulcers which are a major and growing drain on the health system, and an urgent and major unmet clinical need.

Accordingly, aspects of the invention concern the therapeutic use of HS8 in the repair and/or regeneration of skin. Repair or regeneration of skin may be required in response to injury or formation of a wound in the skin. The therapeutic use may involve treatment of skin wounds or skin scars of any kind. Wounds may be acute or chronic. Wounds may be slow-healing or non-healing.

The injury may be any injury that disrupts the skin barrier. In some embodiments the injury may be a physical or mechanical injury. It may be an excisional wound or excisional skin trauma. In some embodiments the wound may be a cut, stab or puncture wound. In some embodiments it may be a surgical cut. In other embodiments the injury may be a result of a burn, which may be a heat or chemical burn. Burns which may be treated may be first degree, second degree or third degree. The action of HS8 may be to facilitate or accelerate the wound healing process in response to such injuries.

In some embodiments HS8 may be used to facilitate or accelerate wound healing in skin or skin graft healing, e.g. following skin grafting, skin reconstruction or skin plastic surgery. In some embodiments HS may be used to reduce or minimise scar formation during skin wound healing. In some embodiments HS8 is used to achieve scarless wound healing in skin.

Therapeutic applications of HS8 in skin wound healing include wound healing after plastic surgery, colorectal anastomotic surgery, closing up stitches, treatment of burns, vascular/arterial/pressure ulcer treatment, skin incisional/trauma wound repair, the encouraging of blood vessels back into the epidermal compartment and stimulation of epidermal stem cell function.

In some embodiments HS8 may be used to treat a skin ulcer, for example a diabetic skin ulcer. Skin ulcers may be non-healing ulcers, e.g. non-healing lower extremity ulcers.

In some optional embodiments, HS8 is not used for the treatment of graft versus host disease of the skin.

Skin Grafting, Reconstruction and Plastic Surgery

Skin grafting involves the transplantation of skin and is often used to treat traumatic wounds in which large areas of skin are damaged, e.g. in burns, skin cancer or following infections such as necrotizing fasciitis The process typically involves surgical removal of the damaged skin followed by grafting of transplanted skin. Skin grafts may be obtained by removing either a thin layer of skin or a full thickness section of skin from a healthy part of the body. Grafts are typically obtained from the subject requiring treatment (autologous) or from another individual of the same species (allogeneic)

Skin grafting, reconstruction and plastic surgery techniques are known to those of skill in the art, for example as described in Snyder et al (Applying split-thickness skin grafts: a step-by-step clinical guide and nursing implications. Ostomy Wound Manage. 2001 November; 47(11):20-6.); Jeffrey E. Janis (Essentials of Plastic Surgery CRC Press, 22 Jul. 2007) Ziegler, Dietz and Schmidt (Skin Grafts. *Surgery in Wounds.* 2004, pp 179-186); Weerda, Hilko (2001). Reconstructive Facial Plastic Surgery: A Problem-Solving Manual. Barret-Nerin, Juan; Herndon, David N. (2004). Principles and Practice of Burn Surgery. New York: Marcel Dekker.

In aspects and embodiments of the present invention HS8 is provided for use in methods of skin grafting, reconstruction and plastic surgery to assist the skin healing process and/or acceptance of the graft. HS8 may be applied or administered to the skin at or adjacent the site of grafting, reconstruction or surgery. Such application may form part of the surgical method or may be separate to the surgical method, e.g. being applied post-surgery to an area of skin that has undergone grafting, reconstruction or plastic surgery.

Formulations

While it is possible for the active compound, HS8, to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with HS8 and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for topical or transdermal administration may be preferred and may include gels, sprays, pastes, ointments, creams, lotions, salves, oils, aqueous solutions, suspensions, and dispersions as well as patches, adhesive plasters, bandages, dressings, depots, and reservoirs.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

Topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired pharmaceutical properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

HS8 could be applied to a number of therapeutic applications in skin care that include wound healing and coating technology for wound dressings. As such, formulations may suitably be provided as a patch, adhesive plaster, bandage, dressing, tissue scaffold (e.g. see Zhong et al., Tissue scaffolds for skin wound healing and dermal reconstruction. Science 1997 Apr. 4; 276(5309):75-81), a biomaterial or the like which is impregnated with, or coated with, HS8 and optionally one or more other pharmaceutically acceptable ingredients, including, for example, penetration, permeation, and absorption enhancers.

Pharmaceutical compositions, medicaments, and other formulations comprising HS8 may also comprise FGF2. Owing to the ability of HS8 to bind FGF2, the HS8 may act as a carrier of FGF2 assisting in delivery of FGF2 to the wound site.

Administration is preferably in a "therapeutically effective amount", this being sufficient to repair and/or regenerate the skin. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS8 doses may be administered in accordance with the guidance of the prescribing medical practitioner. Purely by way of example, HS8 may be delivered in dosages of at least 1 ng/ml, more preferably at least 5 ng/ml and optionally 10 ng/ml or more. Individual HS8 dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS8 may be used to repair and/or regenerate skin alongside other treatments, such as administration of pain relieving or anti-inflammatory medicaments.

Bone Fracture

In some aspects the present invention is concerned with the therapeutic use (human and/or veterinary) of HS8 to treat bone fracture.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS8 include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using HS8 include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using HS8 also include those of the head (skull) and neck, including those of the face such as the jaw, nose and cheek. HS8 may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of HS8 may be on cells within, adjacent to, or caused to migrate into the wound site and may be on the mesenchymal stem cells, bone stem cells, the preosteoblasts or the osteoblasts, or on any of the ancillary or vasculogenic cells found or caused to migrate into or within the wound bed.

HS8 and pharmaceutical compositions and medicaments comprising HS8 are provided for use in a method of treatment of bone fracture in a mammalian subject. Treatment may comprise wound healing in bone. The treatment may involve repair, regeneration and growth of bone. HS8 facilitates fracture repair by facilitating new bone growth. HS8 acts to improve the speed of fracture repair enabling bone healing to occur faster leading to improved recovery time from injury. Treatment may lead to improved bone strength.

Treatment may also include treatment of osteoporosis or osteoarthritis.

Administration of HS8 is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably HS8 is formulated in fluid or liquid form for injection.

In some embodiments the HS8 is formulated as a controlled release formulation, e.g. in a drug capsule for implantation at the wound site. The HS8 may be attached to, impregnated on or soaked into a carrier material (e.g. a biomaterial) such as nanofibres or biodegradable paper or textile.

Pharmaceutical compositions, medicaments, implants and prostheses comprising HS8 may also comprise FGF2. Owing to the ability of HS8 to bind FGF2, the HS8 may act as a carrier of FGF2 assisting in delivery of FGF2 to the wound site.

Administration is preferably in a "therapeutically effective amount", this being sufficient to improve healing of the bone fracture compared to a corresponding untreated fracture.

The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS8 doses may be administered in accordance with the guidance of the prescribing medical practitioner. Purely by way of example, HS8 may be delivered in dosages of at least 1 ng/ml, more preferably at least 5 ng/ml and optionally 10 ng/ml or more. Individual HS8 dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS8 may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS8 may be administered directly to (e.g. applied to) the fracture during the surgical procedure.

Biomaterials

Pharmaceutical compositions and medicaments of the invention may take the form of a biomaterial that is coated and/or impregnated with HS8. An implant or prosthesis may be formed from the biomaterial. Such implants or prostheses may be surgically implanted to assist in transplantion of cells, bone growth, tissue regeneration, tissue restructuring and/or tissue re-modelling.

HS8 may be applied to implants or prostheses to accelerate new tissue formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS8. Impregnation may comprise forming the biomaterial by mixing HS8 with the constitutive components of the biomaterial, e.g. during polymerisation, or absorbing HS8 into the biomaterial. Coating may comprise adsorbing the HS8 onto the surface of the biomaterial.

The biomaterial should allow the coated or impregnated HS8 to be released from the biomaterial when administered to or implanted in the subject. Biomaterial release kinetics may be altered by altering the structure, e.g. porosity, of the biomaterial.

In addition to coating or impregnating a biomaterial with HS8, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with HS8. Examples of useful bisphosphonates may include at least one chosen from the group consisting of: etidronate; clodronate; alendronate; pamidronate; risedronate; zoledronate.

Biomaterials coated or impregnated with HS8 may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a crosslinked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices*. 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications*. 2000; 14(3); 229-242; DeBlois Cote M F. Doillon C J. Heparin-fibroblast growth factor fibrin complex: in vitro and in vivo applications to collagen based materials. *Biomaterials*. 1994; 15(9): 665-672.).

Luong-Van et al (In vitro biocompatibility and bioactivity of microencapsulated heparan sulphate Biomaterials 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

One example of a biomaterial suitable for use in combination with HS8 is the JAX™ bone void filler (Smith & Nephew). Jax granules are composed of high purity calcium sulfate and retain their shape to provide a scaffold with controlled, inter-granular porosity and granule migration stability. Jax granules dissolve safely and completely in the body.

Other suitable biomaterials include ceramic or metal (e.g. titanium), hydroxyapatite, tricalcium phosphate, demineralised bone matrix (DBM), autografts (i.e. grafts derived from the patient's tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

The biomaterial can be supplemented with additional cells. For example, one can "seed" the biomaterial (or co-synthesise it) with undifferentiated bone precursor cells, e.g. stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Dosages of Heparan Sulphate

In both in vitro and in vivo uses, HS8 may be used in concentrations or dosages of about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or about between 0.3-5 µg/ml, 0.3-4, 0.3-3, 0.3-2.5, 0.3-2, 0.3-1.5, 0.3-1.0, 0.3-0.9, 0.3-0.8, 0.3-0.7, 0.3-0.6, 0.3-0.5, 0.3-0.4, 1-2, 1-1.75, 1-1.5, 1-1.25, 1.25-2, 1.5-2, or 1.75-2 µg/ml.

FGF2

In this specification FGF2 refers to fibroblast growth factor 2 (also known as basic fibroblast growth factor (bFGF) or FGF-β) which is a member of the fibroblast growth factor family.

FGF2 is present in the basement membranes of many tissues and is thought to stay membrane bound in the absence of a signal stimulus. FGF2 has been implicated in wound healing, tumor development and angiogenesis.

Binding of FGF2 to Its tyrosine kinase receptor stimulates a signal cascade involving activation of mitogen activated protein kinase (MEK) and phosphorylation of extracellular signal-related kinases (ERKs) (e.g. see Ok-Jin Park et al., The Journal of Biological Chemistry, 285, (2010) 3568-3574).

The amino acid sequence of FGF2 from *Homo sapiens* is shown in FIG. 28 (the heparin binding domain SEQ ID NO:1 is underlined). This sequence is available in Genbank under Accession no. NP_001997.5 (GI:153285461).

In this specification "FGF2" includes proteins or polypeptides having at least 70%, more preferably one of 75%, 80%, 85%, 90%, 95%, 96%, 97%, 98%, 99% or 100% sequence identity with the amino acid sequence of FGF2 illustrated in FIG. 28.

The FGF2 protein or polypeptide preferably also includes a heparin binding domain having the amino acid sequence of SEQ ID NO:1, or an amino acid sequence having one of 75%, 80%, 85%, 90%, 95%, 96%, 97%, 98%, or 99% sequence identity to SEQ ID NO:1.

An FGF2 protein or polypeptide may be a fragment or truncate of a full length FGF2 protein or polypeptide.

The FGF2 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

Dosages of FGF2

In both in vitro and in vivo uses, FGF2 may be used in combination with HS8. In some cell culture methods of the present invention exogenous HS2 is added to the culture. Suitable concentrations or dosages of FGF2 include about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or between about range 0.1-5 ng/ml, 0.1-0.2, 0.1-0.3, 0.1-0.4, 0.1-0.5, 0.1-0.6, 0.1-0.7, 0.1-0.8, 0.1-0.9, 0.1-1.0, 0.1-1.5, 0.1-2.0, 0.1-2.5, 0.1-3.0, 0.1-3.5, 0.1-4.0, 0.1-4.5, 0.1-5.0 ng/ml.

In some embodiments, in vitro and in vivo uses of HS8 exclude the addition of exogenous FGF2. For example, in some cell culture methods of the present invention exogenous FGF2 is not added to the culture.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 5. Table showing FGF2 Heparin binding domain peptides.

FIG. 15. Graph showing binding capacity of different GAGs for FGF2 as assessed by GAG-binding plates (Iduron). The HS8 (HS8+) fraction binds FGF2 almost as well as heparin, and better than the raw starting Celsus HS and the HS8– flow through.

FIG. 21. Illustration of results of representative FACS immunophenotyping of hMSC (Lonza) stem cells, based on the following markers: (A) Negative markers: CD14, CD19, CD34, CD45, HLA-DR, and (B) Positive markers: CD73, CD90, CD105, STRO-1, SSEA-4, CD49a.

FIG. 22. Quantitation Table of FACS immunophenotyped hMSC stem cells grown for 7 passages in unsupplemented (control), HS8 (HS8+), HS8−, raw Celsus HS (CHS), or FGF2 alone. Table shows percentage of cells expressing the relevant cell surface marker: CD14, CD19, CD34, CD45, HLA-DR, CD73, CD90, CD105, CD49a, SSEA-4, STRO-1.

FIG. 28. Amino acid sequence of human FGF2. SEQ ID NO:1 shown in underline.

FIG. 29. Nitrous acid-derived disaccharide composition of heparan sulfate from E10 neuroepithelia (HS2). Radiolabelled HS was depolymerized by deaminitive cleavage with low pH $HNO_2$. Disaccharides were isolated after $HNO_2$ treatment of the GAGs and the samples then run on a 1×120 cm Bio-Gel P-2 column. The resulting disaccharides were fractionated by SAX-HPLC. Areas under the peaks were integrated to give the disaccharide composition and subsequently, the percentage composition in each sample.

FIG. 30. Disaccharide composition of heparan sulfate from E10 neuroepithelium (HS2) following heparin lyase treatment. Heparan sulfate was completely depolymerized with a mixture of heparin lyases. The resulting unsaturated disaccharides were isolated on a P-2 column and fractionated by strong anion exchange column chromatography. The area under each resultant curve was integrated to calculate the percentage of each disaccharide in each sample. Numbers represent the average of two runs (for the primary GAG samples) and three runs (for the 2.3D derived samples). Over 97% disaccharides were recovered from each sample.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Example 1

We investigated the purification of a new FGF2 binding HS from commercially available Porcine Celsus Heparan sulphate sources suitable for scale up of heparan sulphate (HS) preparations that can be readily used in the clinic.

The Heparin binding domain (HBD) peptide sequence GHFKDPKRLYCKNGGF [SEQ ID NO:1] from FGF2 was selected (The structure of glycosaminoglycans and their interactions with proteins; Gandhi N S and Mancera R L., *Chem Biol Drug Des.* 2008 December; 72(6):455-82) and used to purify specific HS species binding to FGF2.

Upon synthesizing the peptide, it was subjected to the $^3$H Heparin assay where specific binding of $^3$H Heparin to the peptide soaked to a nitrocellulose membrane in a dose dependent manner was compared to the total counts of the $^3$H Heparin. Once the specific binding of $^3$H Heparin to the FGF2-HBD peptide was shown the peptide was used to pull down a specific HS from Porcine Celsus HS which binds to FGF2 by affinity chromatography. This new HS species was named as HS8 (and was given the variant name HS8G).

HS8 was analysed for its specificity in binding with FGF2 with glycosaminoglycan (GAG) binding plates where the specific binding of HS8 to FGF2 was measured in comparison to Heparin, Porcine Celsus HS and HS8 negative fraction.

The GAGs were plated on GAG binding plate (5 μg/ml) overnight and later incubated with recombinant human FGF2 (0-100 ng/ml) and an ELISA method was used to check the specificity of binding of GAGs to FGF2.

Figure 1:
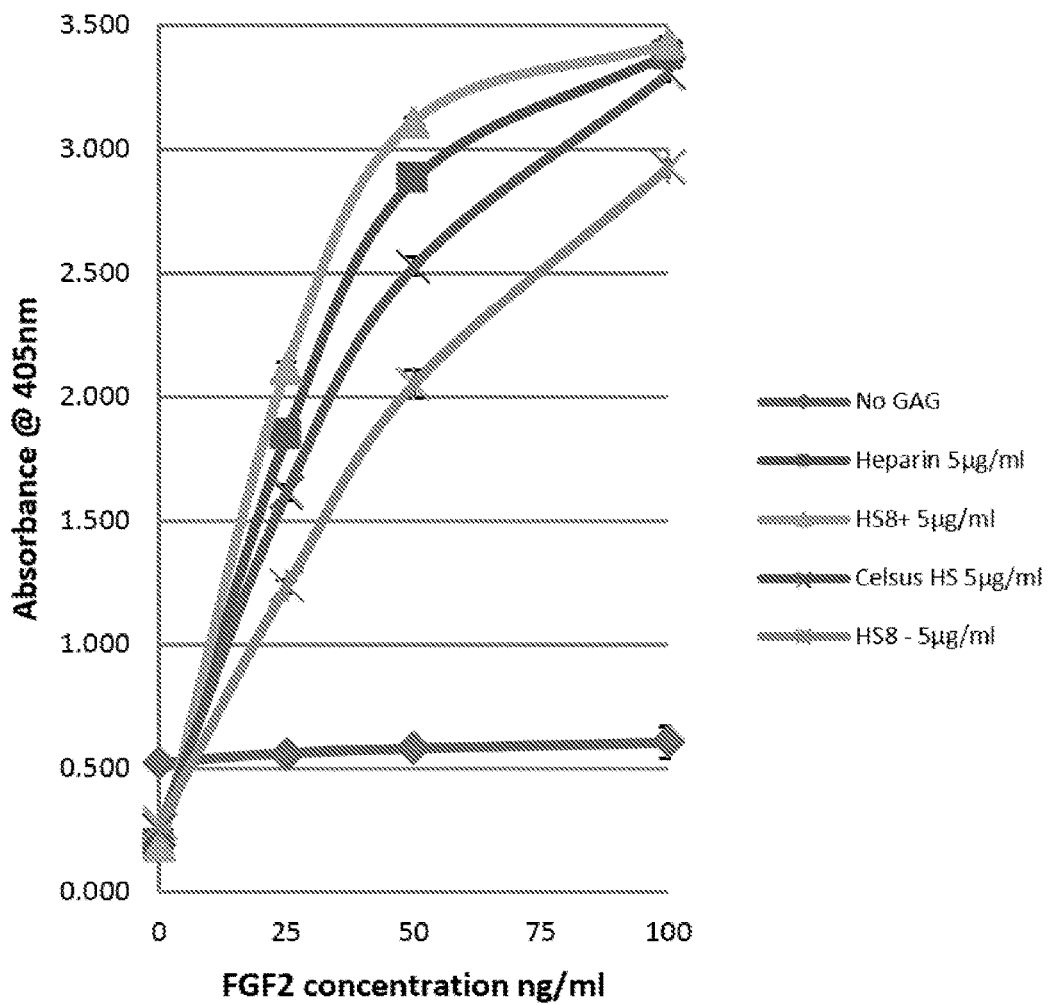
FIG. 1. Graph showing binding of different GAGs (5 µg/ml) to FGF2 (1-100 ng/ml). Preferential binding of HS8 to FGF2 was observed at concentrations of FGF2 of 0, 25, 50 and 100 ng/ml. Data lines from top of graph down: HS8+(5 µg/ml) (triangles), Heparin (5 µg/ml) (squares), Celsus HS (5 µg/ml), HS8– (5 µg/ml), No GAG (diamonds).
Figure 2:
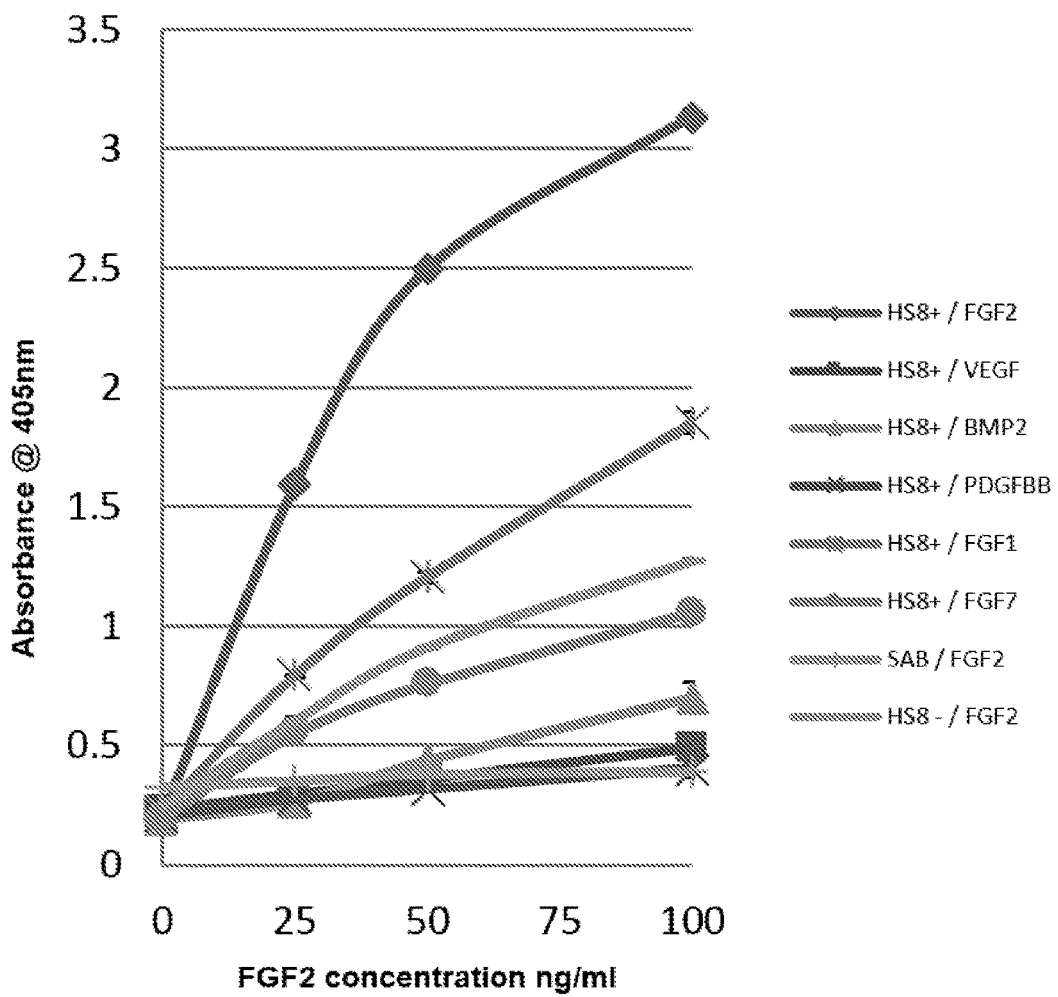
FIG. 2. Graph showing HS8+ binding (5 µg/ml) to different proteins (0-100 ng/ml), demonstrating specificity of HS8 (5 µg/ml) for FGF2. Data lines from top of graph down: HS8+/FGF2 (diamonds), HS8+/FGF1, HS8–/FGF2, HS8+/FGF7, HS8+/BMP2, HS8+/VEGF, SAB/FGF2, HS8+/PDGFBB.

The results clearly showed that HS8 has more binding to FGF2 compared to other GAG species (FIG. 1). The ability of HS8 to bind FGF2 was compared against other growth factors (VEGF, BMP2, PDGFBB, FGF1, and FGF7) which revealed that HS8 is specific to FGF2 (FIG. 2).

Figure 3:
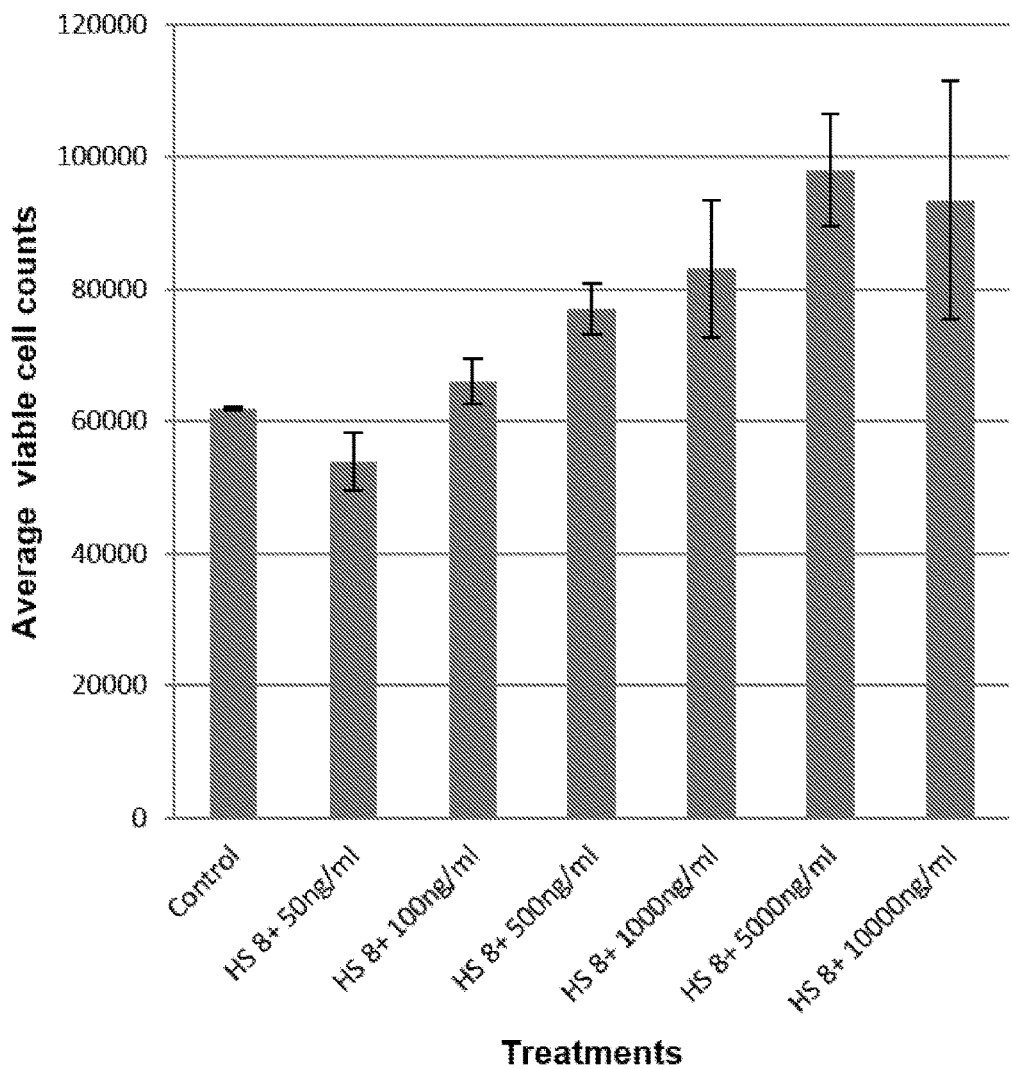
FIG. 3. Graph showing dose dependent increase in number of STRO1 human mesenchymal stem cells at day 6 in response to treatment with HS8. Bars from left to right represent: Control, HS8+ 50 ng/ml, HS8+ 100 ng/ml, HS8+ 500 ng/ml, HS8+ 1000 ng/ml, HS8+ 5000 ng/ml, HS8+ 10000 ng/ml.
Figure 4:
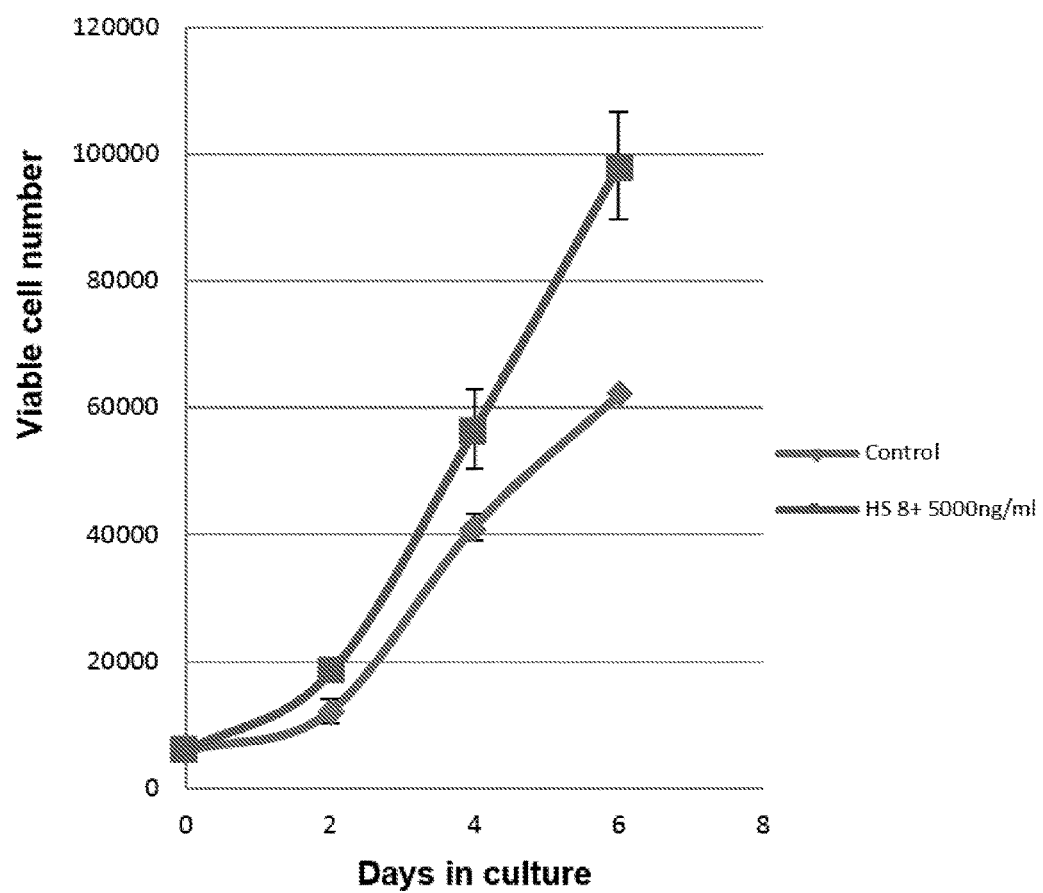
FIG. 4. Graph showing proliferation of STRO1 human mesenchymal stem cells over 6 days in response to HS8+ 5000 ng/ml (squares) and control (diamonds).

HS8 was also subjected to in vitro cell proliferation assay with STRO1 human mesenchymal stem cells (hMSCs) to determine the bioactivity of HS8. We used HS8 as a stand-alone media supplement with different doses (50 ng/ml, 100 ng/ml, 500 ng/ml, 1000 ng/ml, 5000 ng/ml and 10000 ng/ml) in short term growth of hMSCs compared to the controls. Without any addition of exogenous growth factors we observed a dose dependent growth of hMSCs with HS8 (FIGS. 3 and 4).

Example 2

Mesenchymal Stem Cells (MSCs)

MSCs are widely defined as plastic-adherent cells which can be directed to differentiate in vitro into osteogenic, chondrogenic, adipogenic, myogenic, and other lineages and recently, the name "multipotent mesenchymal stromal cells" was also coined to MSCs by the International Society for Cytotherapy (Zulma et al, 2011). MSCs are been found in bone marrow, adipose tissue, dermal tissue, intervertebral disc, amniotic fluid, various dental tissues, human placenta and cord blood (Si et al, 2011 and Zulma et al, 2011). The therapeutic potential of MSCs have been recognized and been used in many clinical applications such as bone tissue regeneration and non skeletal tissue regenerations. In recent years the immunosuppressive and anti-inflammatory effects of MSCs were described. This is due to MSCs weak immunogenicity by expressing low levels of major histocompatibility complex-I molecules (MHC-1) on their cell surface, ability to suppress the activation and proliferation of both T and B lymphocytes and modifying the microenvironment of injured tissues while protecting damaged tissues (Si et al, 2011 and Zulma et al, 2011). This MSC-mediated immunosuppression which can be affectively used to treat GVHD has a species variation in mechanism (Ren et al, 2009 and Shi et al, 2010). The cytokine-primed mouse MSCs is mediated by nitric oxide (NO) and cytokine-primed human MSCs is executed through indoleamine 2, 3-dioxygenase (IDO).

Heparin and Heparan Sulfate Glycosaminoglycans (HS-GAGs)

Heparin is produced and stored in mast cells and in comparison, HSGAGs are found in all animal tissues and they can occur as a proteoglycan where HS chains are bound to cell surface or ECM proteins. HS affects metabolism, transport, information transfer, cell adhesion, cell growth and differentiation, and support in all organ systems (Bishop et al, 2007 and Gandhi et al, 2008). Heparin and HS are linear polysaccharides consisting of repeating uronic acid-(1→4)-D-glucosamine disaccharide subunits. Uronic acid can either be D-glucuronic acid or L-iduronic acid. In addition, modifications at specific places give rise to different N-sulfated, 0-sulfated and N-acetylated complex sequences [Ori et al 2008]. The most abundant disaccharide in heparin is IdoA(2S)-(1→4)-GlcNS(6S) therefore giving rise to highly negative charge throughout the chain length, which makes heparin less or no selectivity in binding to proteins. On the other hand, HS has the unsulfated GlcA-(1→4)-GlcNA disaccharide as the most common form which giving rise to segregated blocks of unsulfated NA domains and blocks of highly sulfated, heparin-like IdoA-(1→4)-GlcNS disaccharides (NS domain). The NA and NS domain is separated by NA/NS transition domains. This diversity of HS structure is responsible for wide range of biological functions.

Fibroblast Growth Factor (FGF) Proteins and Heparin Binding Domains

Fibroblast growth factors (FGFs) are large family of polypeptide growth factors which comprise of 22 members in humans. They play a major role in development, differentiation, cell proliferation, angiogenesis and wound healing by binding and activating a subfamily of FGF cell surface receptor tyrosine kinases known as FGF receptors (FGFR) (Ornitz et al 1996). Furthermore, the FGFs are among the best-studied heparin-binding proteins, and HSGAGs regulate FGF signaling by direct molecular association with FGFRs (Pellegrini, 2001). In addition, FGF2 signaling through FGFR1 is important for MSC expansion (Gronthos et al, 1999).

Interactions of Heparin/HS with FGF2

Various studies have recognized common structural features in the heparin/HS binding sites of proteins (Gandhi et al, 2008; Hileman et al, 1998 and Ori et al, 2008). Cardin and Weintraub in 1989 made a first attempt to determine the heparin binding domain (HBD) after analyzing 21 heparin-binding proteins and proposed that typical heparin-binding sites may have the sequence XBBXBX or XBBBXXBX, where B is a positively charged amino acid (arginine, lysine and rarely histidine) and X is a hydropathic residue. The next consensus sequence TXXBXXTBXXXTBB, was introduced by Hileman et al in 1998 after Comparing X-ray and NMR of several proteins. In this sequence T defines a turn, B a basic amino acid (arginine or lysine) and X a hydropathic residue.

Strong ionic interactions are expected between GAGs and proteins with positively charged basic amino acids form ionic bonds with negatively charged sulphate or carboxylate groups on heparin chains. Their role is determinant for the interaction with heparin and, possibly, with the highly sulfated regions within HS like NS domains (Fromm et al, 1997 and Ori et al, 2008). In addition, there are other types of bonds namely van der Waals forces, hydrogen bonds and hydrophobic interactions. These bonds will come in to play for the interactions with the more heterogeneous HS, where neutral amino acids are also required (Fromm et al, 1997 and Ori et al, 2008). In considering FGF2, Glutamine and asparagine amino acids play an important role for the interaction with HS by forming hydrogen bonds with the hydroxyl groups of the sugar in addition to the ionic bonds (Thompson et al, 1994).

According to the numerous published studies so far, there are different peptide sequences as the heparin binding domain of FGF2 and those have been compiled in the table 1. Here we have adopted a numbering system where the amino acids are numbered according to the full FGF2 sequence (288aa).

Graft Versus Host Disease (GVHD)

Haemopoietic-cell transplantation (HCT) is an intensive therapy used to treat haematological malignant diseases where allogeneic HCT procedures are increasing annually (Ferrara et al, 2009). The major complication of HCT is GVHD, an immunological disorder that affects mainly gastrointestinal tract, liver, skin, and lungs. According to Billingham, 1966-67 three requirements should be fulfilled if GVHD to occur namely, 1) the graft must contain immunologically competent cells which are T lymphocytes, 2) the recipient must express tissue antigens that are not present in the transplant donor, and 3) the patient must be incapable of mounting an effective response to abolish the transplanted cells. GVHD pathophysiology starts when myeloablative conditioning regimes are used to remove the host defective bone marrow. The host's antigen presenting cells get activated because of the cytokines (TNFα, IL1, LPS) produced by the damaged tissues. Once the allogeneic HCT has been performed at this stage donor T cells get activated which thereby produce more cytokines leading to cellular and inflammatory reactions resulting in GVHD. Non-haemopoietic stem cells; MSCs, can reduce allogeneic T-cell responses due to their potent immunosuppressive and ameliorate GVHD (Le Blanc et al, 2008; Meuleman et al, 2009 and Toubai et al, 2009).

Need to Scale Up of hMSC for Therapeutic Purposes

A major drawback of hMSCs usage in cell based therapies is that the difficulty in achieving sufficient cell numbers, though they are already been used in the clinics. The low numbers of hMSCs, where it can be as low as 0.01% to 0.0001% of bone marrow mononuclear cells hinders the widespread usage of it. According to Caplan, 2009 where they obtained bone marrow from different aged donors, dispersed, placed on culture flasks, later counted the CFU-Fs and shown by decade of age versus the MSCs per nucleated marrow cells. A remarkable decrease in MSCs per nucleated marrow cells was observed, with a 10-fold decrease from birth to teens and another 10-fold decrease from teens to the elderly. Clearly, with age the number of MSCs in marrow decreased. In addition, Caplan pointed out that these decreases paralleled the observed fracture healing rates of young and adults. In comparison, the titres of haematopoietic stem cells in marrow which were around one per $10^4$ nucleated marrow cells, remained constant throughout the age of the individual.

Current Expansion Methods of hMSCs

Researchers have thought that, if they can mimic the bone marrow microenvironment in culturing hMSCs they can achieve therapeutic numbers of hMSCs for clinical use. Basically, mimicking can be achieved by two broad ways namely growing hMSCs with ECM and with exogenous growth factor supplementation. When ECM substrates were used, increased hMSC attachment and cumulative cell number were observed (Grünert et al, 2007 and Matsubara et al, 2004) but, the expanded cells were lacking stemness (Cool et al, 2005). In addition, FGF2 was commonly used as exogenous growth factor supplementation which also showed marked amplification of cell number (Ling et al, 2006 and Sotiropoulou et al, 2006) compared to the controls with standard culture media. In line with the cells grown with ECM substrates the cells grown with FGF2 also had increased amounts of differentiated progenitors compared to multipotant hMSCs in controls (Gronthos et al, 1999 and Walsh et al, 2000). Hence, identification of a molecule which prompts the proliferation of hMSCs where we can achieve therapeutic numbers of hMSCs without adversely affecting the stemness shows a great promise in clinical use of hMSCs for bone regeneration and bone marrow transplantations to alleviate GVHD.

HS GAGs Improve the Growth of hMSCs without Affecting the Stemness of Cells

Nurcombe et al in 1993 have shown that, activity of FGF on murine neural precursor cells regulated by HS GAGs and this interaction is a requirement for the binding of FGF2 to their receptors. In addition, there was a significant difference in binding of HSGAGs to FGFs where at day 9 HS GAGs produced by these cells preferentially bound to FGF2 and by day 11, HSGAGs binding shifted to FGF1. Furthermore, these unique heparan sulfates mediate the binding of FGF2 to specific receptors via interacting with cell-surface receptors on neural precursor cells (Brickman et al, 1995). In 1998, Brickman et a/further supported these findings by isolation and characterization of two separate HS pools from immortalized embryonic day 10 mouse neuroepithelial 2.3D cells. One pool was derived from cells in log growth phase, which increased the activity of FGF-2, and the other pool from cells undergoing contact-inhibition and differentiation, which had preference to FGF1. As described previously by our lab, an embryonic HS GAG preparation named HS2 increased the hMSCs growth without significant loss of multipotentiality and lead to increased bone formation in mice when transplanted in vivo. This evidence suggests that ECM component HS GAGs improve the growth of the hMSCs without adversely affecting the multipotentiality. Hence, there is a specific need for a HS variant that is having high binding affinity to FGF2 and potentiates its activity on cell growth which can be readily scalable to be used in clinical settings compared to HS2.

Results

Isolation of the Heparan Sulfate with Higher Binding Affinity to FGF-2 by Column Chromatography (HS8)

In line with the strategy of purifying the FGF2 binding HS2, we seek the possibility of purifying another FGF2 binding HS from commercially available Porcine Celsus heparan sulphate sources (Celsus Laboratories, USA) in order to scale up the HS preparation which could be readily used in the clinics. Out of these peptides sequences which are presented in the table 1 $^{157}$GHFKDPKRLYCKNGGF$^{172}$ (Gandhi et al, 2008) which was named FGF2-Gandhi-HBD was used.

[$^3$H] Heparin Assay

Upon synthesizing the peptides, they were subjected to $^3$H Heparin assay where the capability of the FGF2-HBD-peptides binding to heparin was tested. Known amounts of peptides or saturating amounts of peptides were dried onto identical nitrocellulose membranes which were first air dried and then further dried for 45 min in a vacuum oven at 80° C. Then membranes were washes with 1× phosphate buffered saline (PBS) and incubated in counting vials for 16 hr with 0.1 µCi of [$^3$H] heparin (Perkin Elmer, Boston, USA) in 4% (w/v) bovine serum albumin (BSA)/PBS. After that membranes were washed and the radioactivity was determined by Perkin Elmer Tri-Carb 2800 TCR Liquid Scintillation Analyzer.

Figure 6A:
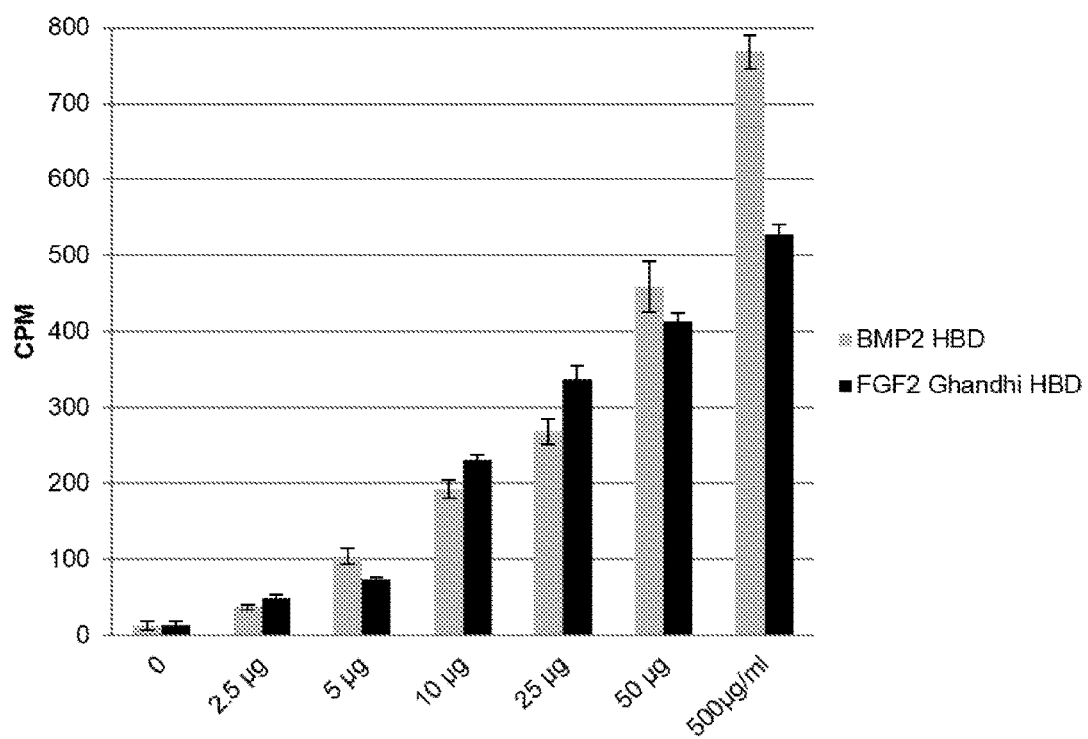
FIG. 6. Graphs showing results of a [$^3$H] assay. (A) Graph showing Radioactivity counts per minutes (CPM) for different amounts of peptide (B) Graph showing HS8 pull down by affinity chromatography FIG. 7. Diagram illustrating arrangement of GAG binding affinity assays.
Figure 6B:
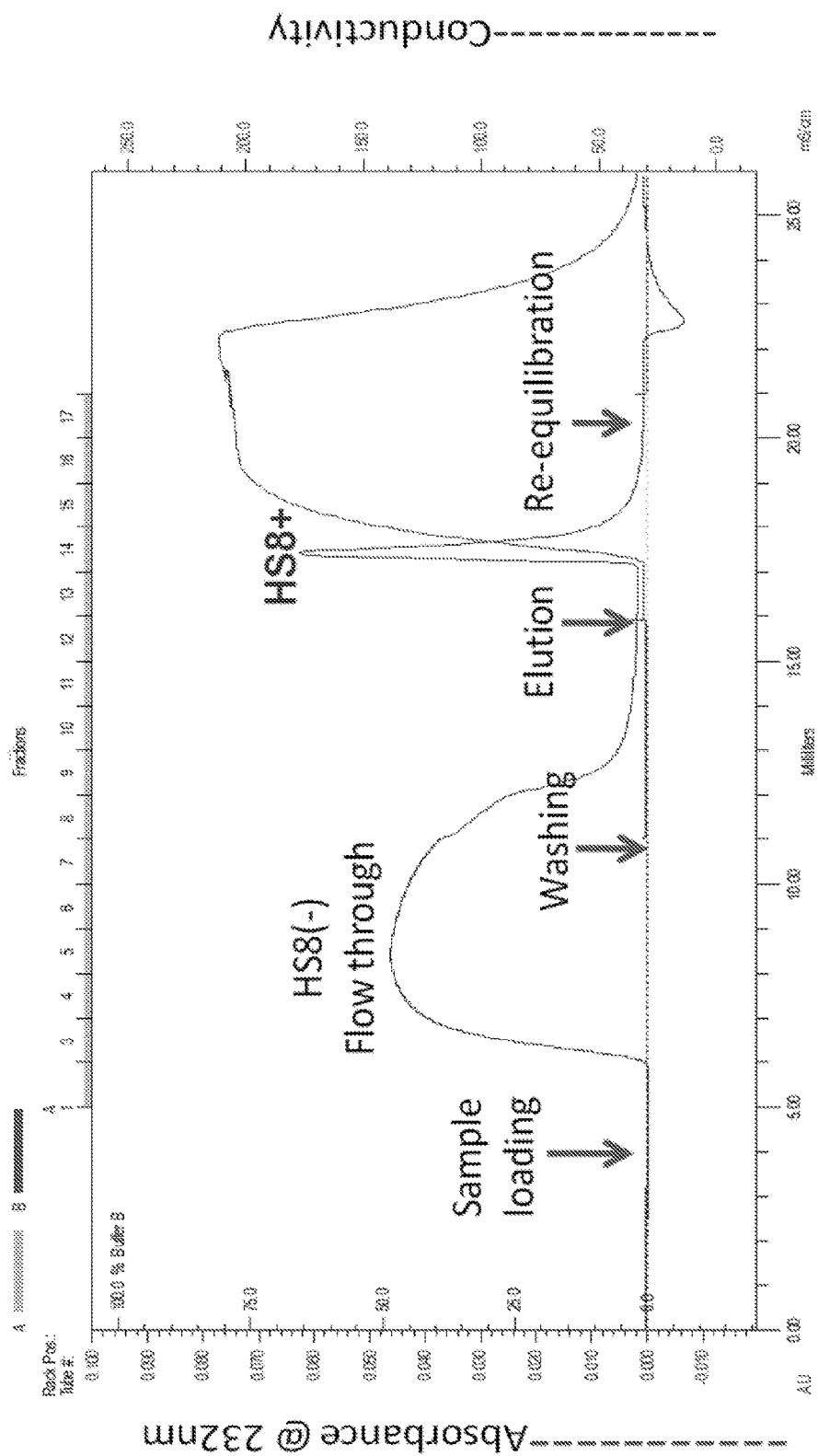
Figure 7:
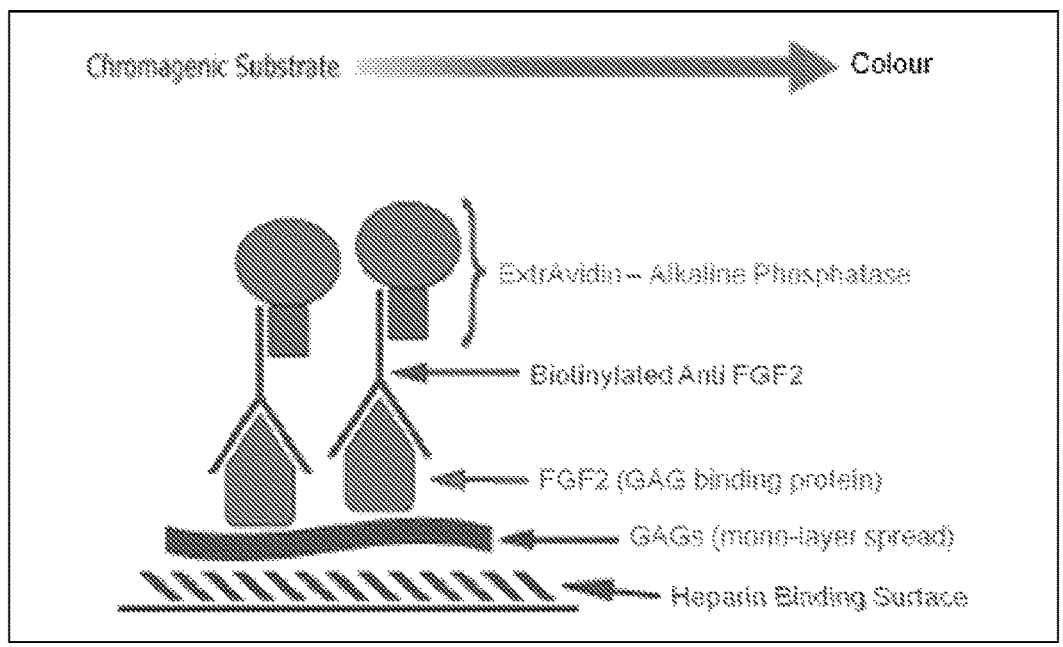
Figure 8A:
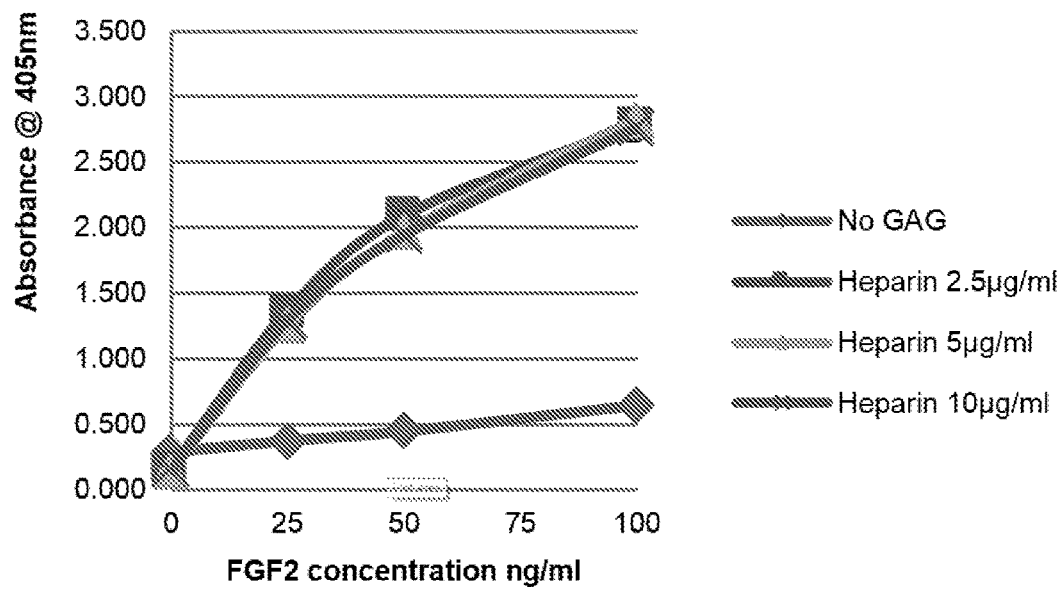
FIG. 8. Graphs showing optimization of different GAGs concentrations binding to FGF2. (A) Heparin (2.5, 5, 10 µg/ml) and FGF2 0, 25, 50, 100 ng/ml—SAB/0.2% Fish gelatin/ExtrAvidin AP 220 ng/ml. (B) HS8+(2.5, 5, 10 µg/ml) and FGF2 0, 25, 50, 100 ng/ml—SAB/0.2% Fish gelatin/ExtrAvidin AP 220 ng/ml. (C) Celsus HS (2.5, 5, 10 µg/ml) and FGF2 0, 25, 50, 100 ng/ml—SAB/0.2% Fish gelatin/ExtrAvidin AP 220 ng/ml. (D) HS8(–) (2.5, 5, 10 µg/ml) and FGF2 0, 25, 50, 100 ng/ml—SAB/0.2% Fish gelatin/ExtrAvidin AP 220 ng/ml.
Figure 8B:
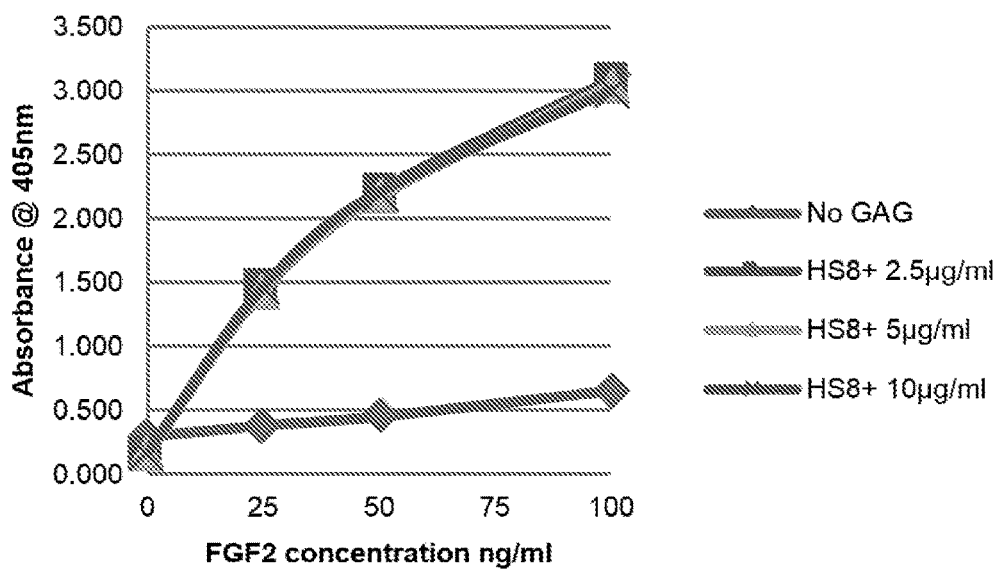
Figure 8C:
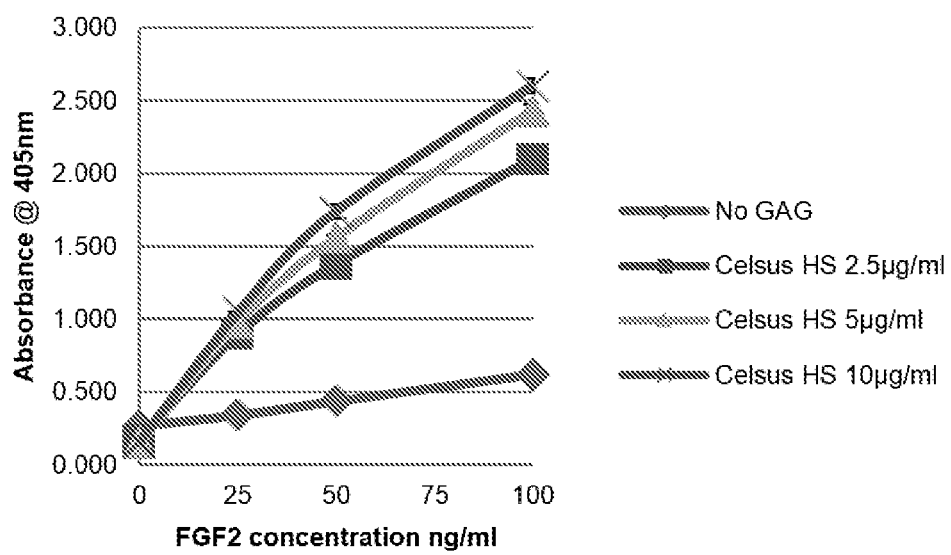
Figure 8D:
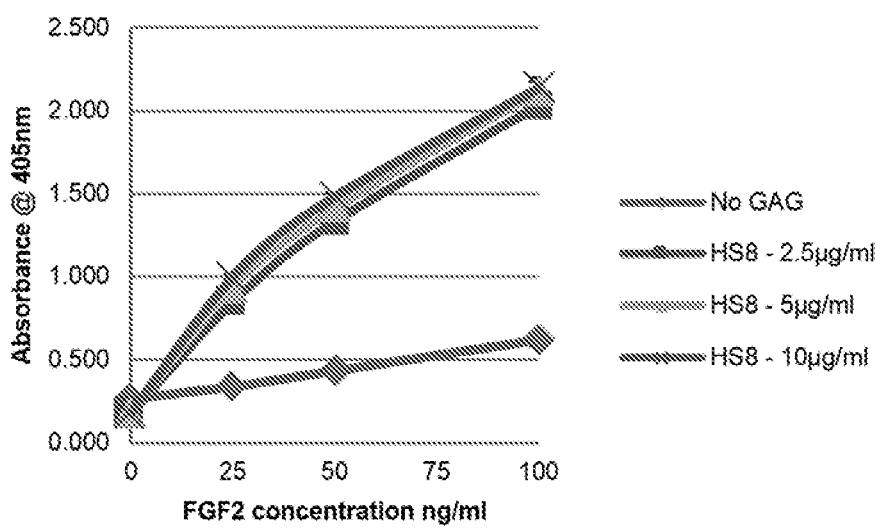

When known amounts of peptide (SEQ ID NO:1) was used they were showing increasing CPM dose dependently, where BMP2-HBD was used as a positive control [FIG. 6(A)]. But the highest counts were shown when the nitrocellulose membranes were saturated in 500 µg/ml peptide solution. The percentage CPM out of Neat [$^3$H] Heparin was calculated for each peptide at the 500 µg/ml solution level. BMP2-HBD (7.2%) had the highest followed by FGF2-Gandhi-HBD (4.97%). According to the results obtained from the [$^3$H] Heparin assay FGF2-Gandhi-HBD was used to pull down the higher affinity binding HS (HS8) to FGF2 from Porcine Celsus HS by affinity chromatography. The chromatogram is shown in the FIG. 6 (B).

Characterization of HS8

GAG Binding Affinity Assays

HS8 was subjected to its affinity in binding to FGF2 and other proteins (R&D Systems) with 96 well GAG binding plates (Iduron, UK) where the specific binding of HS8+ to FGF2 measured in comparison to heparin (Sigma), Porcine Celsus HS (Celsus Laboratories, USA) and HS8 negative fraction. The GAGS were plated on GAG binding plate (2.5-10 µg/ml) overnight and blocked with 0.2% Fish Gelatin (Sigma) in standard assay buffer (SAB) for 1 hour at 37° C.

Then incubated with 200 µl/well of 0-100 ng/ml of recombinant human FGF2 for 2 hrs at 37° C. and later incubated with 200 µl/well of 250 ng/ml primary biotinylated antibody (R&D Systems) for 1 hour in 37° C. In the next step plate was incubated with 200 µl/well of 220 ng/ml ExtrAvidin-AP (Sigma) for 30 min at 37° C. From overnight incubation up to this step plate was washed 3 times with SAB in between each step. Finally, incubated with 200 µl/well SigmaFAST p-Nitrophenyl phosphate (Sigma) for 40 min and absorbance was read at 405 nm by Victor$^3$ 1420 multi-label counter, Perkin Elmer.

Figure 9:
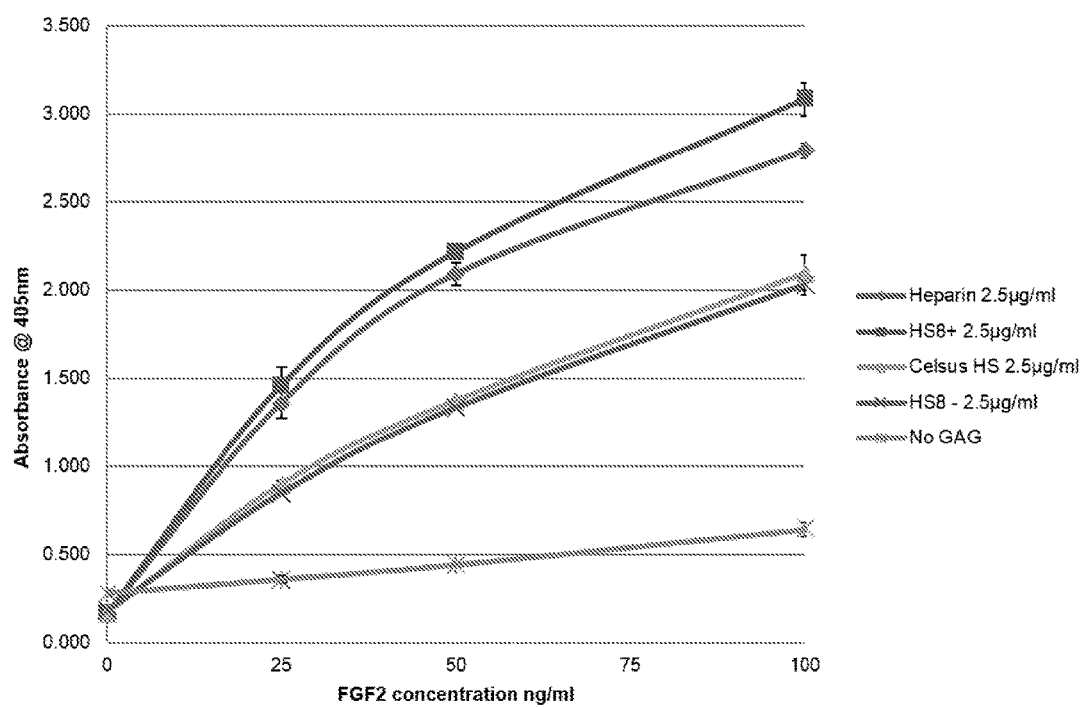
FIG. 9. Graph showing different GAGs (2.5 µg/ml) binding to FGF2 (0, 25, 50, 100 ng/ml)—SAB/0.2% Fish Gelatin/ExtrAvidin AP 220 ng/ml.

Binding of all the GAGs in all 3 concentrations tested (2.5, 5 and 10 µg/ml) to FGF2 increased similarly with increasing amounts of FGF2 and reached a saturation at 100 ng/ml FGF2 (FIG. 8). When different GAGs were tested on binding to FGF2, results clearly showed that HS8+ had the highest affinity of binding to FGF2 to other GAG species (FIG. 9). When compared the fold difference of Celsus HS: HS8+ at 100 ng/ml FGF2 point, the ratio was 1; 1.51.

Figure 10A:
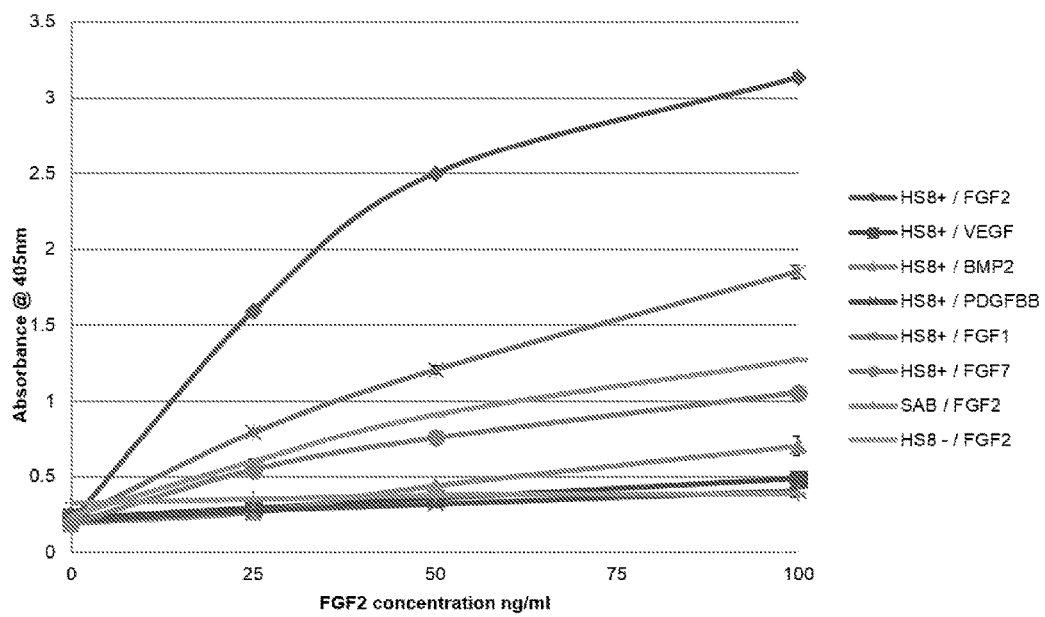
FIG. 10. Graphs showing (A) HS8 (HS8+) and (B) HS8 (–) binding to different proteins. (A) HS8+ 5 µg/ml with different proteins SAB/0.2% Fish Gelatin/22 ng/ml ExtrAvidin AP. (B) HS8(–) 5 µg/ml with different proteins SAB/0.2% Fish Gelatin/22 ng/ml ExtrAvidin AP.
Figure 10B:
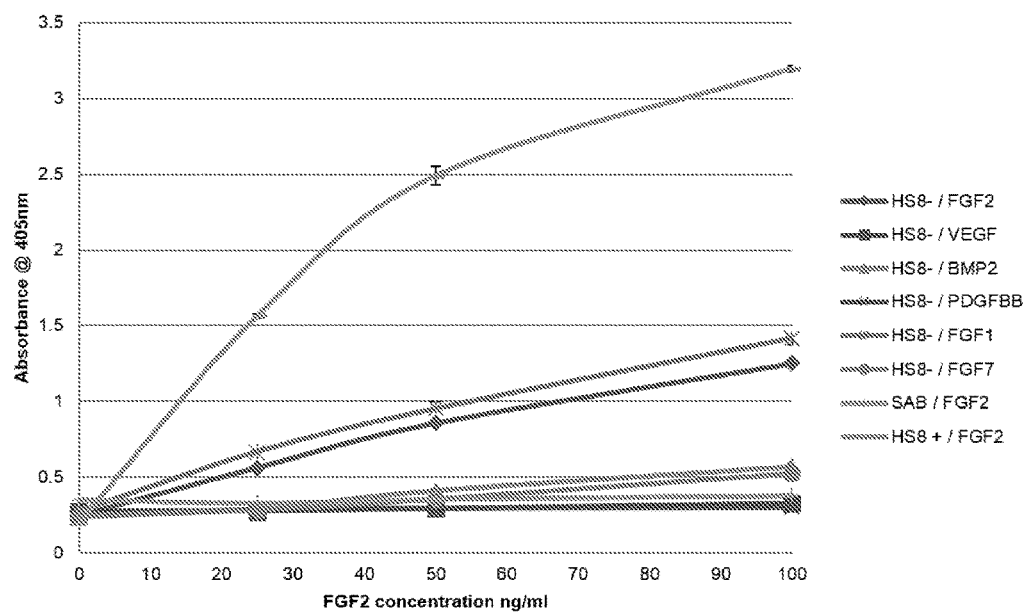

Then we tested the ability of HS8+ and HS8 (–) fractions binding to different proteins (FIG. 10). HS8+ has a higher affinity in binding to FGF2 compared to VEGF, BMP2, PDGFBB, FGF1, and FGF7 [FIG. 10(A)]. On the other hand, HS8 (–) fraction, has the most affinity in binding to FGF1 compared to the other proteins [FIG. 10(B)].

Ability of different GAGs competes with heparin with FGF2 tested in this assay, modified from Ono et al, 1999. A known concentration of FGF2 (R&D Systems) with differing concentrations of GAGs was mixed for 30 min at room temperature (RT) in a microtube.

To this 40 µl of beads solution [20 µl of heparin-agarose beads. (Type I, Sigma) and polyacrylamide gel (Bio-Gel P-30, Bio-Rad)] were added and mixed for 30 min at RT. The heparin beads were washed 3 times by centrifugation (2000 rpm for 1 minute) with BSA-PBS (1% BSA in PBS) and 3 times with PBST (PBS containing 0.02% Tween) and to each tube, 100 µl of 1:500 biotinylated anti-FGF2 (R&D Systems) added and incubated at RT for 1 hr. After washing as above, 100 µl of 1:10 TMB substrate (R&D Systems) was added and mixed for 30 min at RT. Stop solution (50 µl of 2N $H_2SO_4$) was added and 100 µl of the supernatant after centrifugation was transferred to a 96 well plate. The absorbance was read at 450 nm by Victor$^3$ 1420 multi label counter, Perkin Elmer.

Figure 11A:
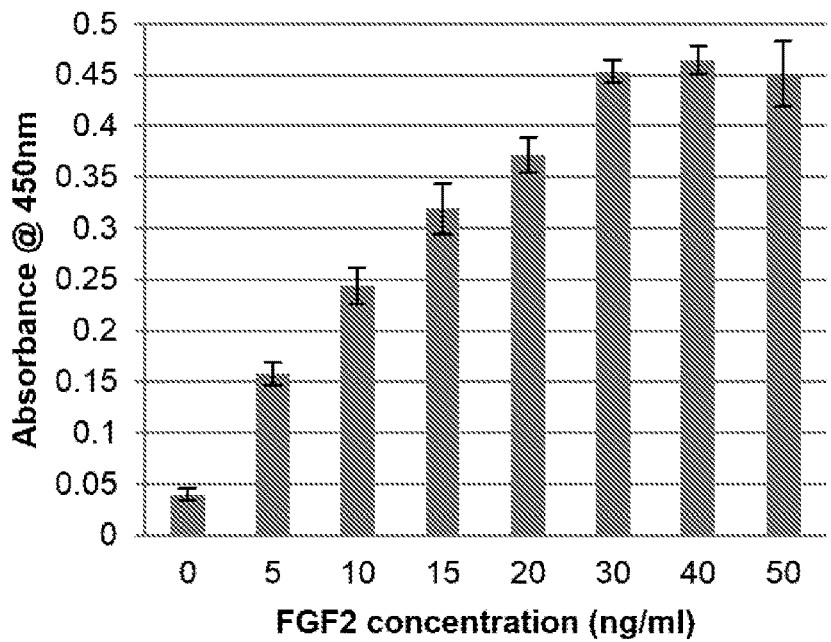
FIG. 11. Graphs showing results of heparin beads assay (A) FGF2 optimization. (B) Heparin beads competition with exogenous heparin. (C) Percentage of competition of heparin beads with different GAGs.

Firstly, the amount of FGF2 needed for binding with the amount of heparin beads added was measured by the FGF2 optimization and the FGF2 dose 20 ng/ml were chosen for the next set of experiments [FIG. 11(A)].

Figure 11B:
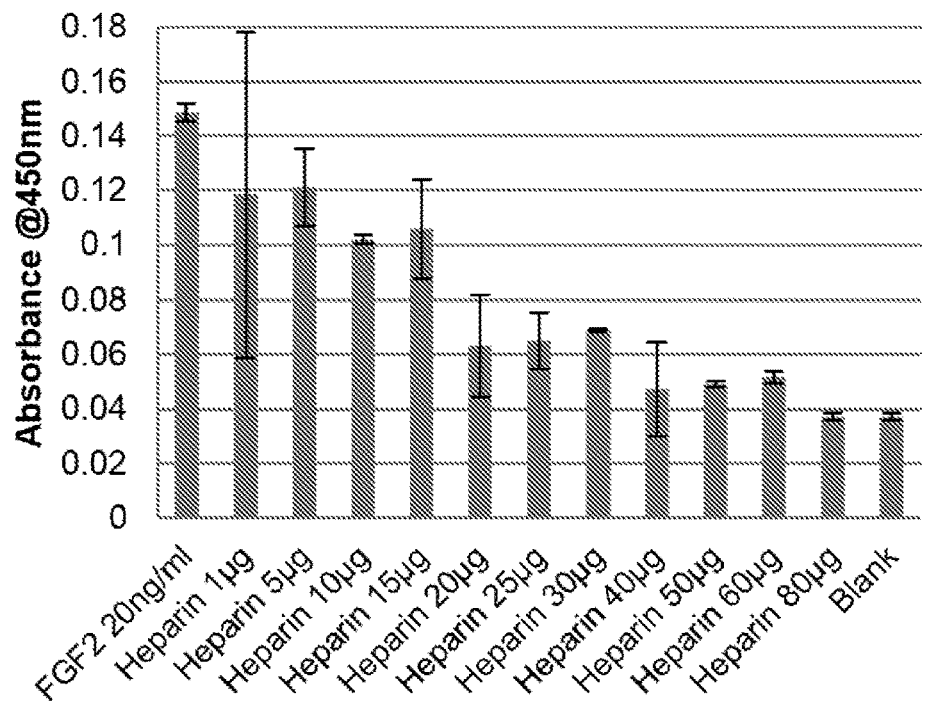
Figure 11C:
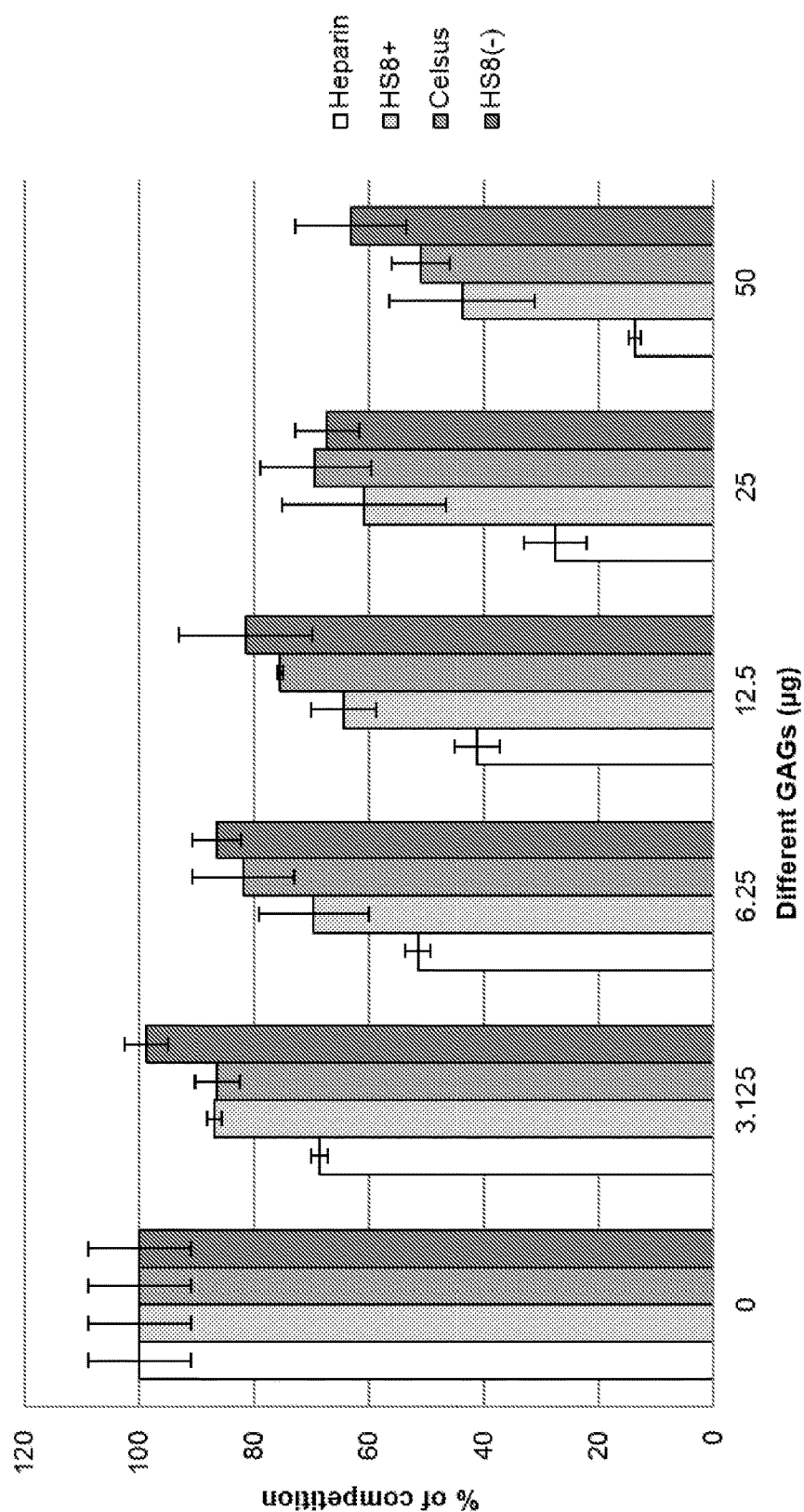

Then in order to get the range of GAGs to be used in the competition assay we initially used different amount of heparin. With the addition 50 µg of heparin was almost sufficient enough to compete with the internal heparin attached to the beads [FIG. 11(B)]. Hence, we used a range of 0-50 µg GAGS in the competition assay [FIG. 11(C)]. When considered the percentage of competition heparin was the most competitive where by adding 50 µg it reached around 13%, followed by HS8+ 43%, Celsus HS 50% and HS8(–) 63%.

Proliferation Assays

Two varieties of hMSCs were used in this assays from a 21 year old Hispanic male donor, where STRO1 positive cells isolated by magnetic activated cell sorting (passage 5-7) and HM21 cells isolated by conventional plastic adherence (passage 5). Cells were seeded 3000 cells/cm$^2$ seeding density and allowed to attach to the plate for 24 hrs. Then the different concentrations of HS 8+ used as stand-alone media supplement ranging from 50-10000 ng/ml and as a positive control 2.5 ng/ml human recombinant FGF2 (R&D Systems) was added to media. Media change was performed either at 2 or 3 days.

Figure 12A:
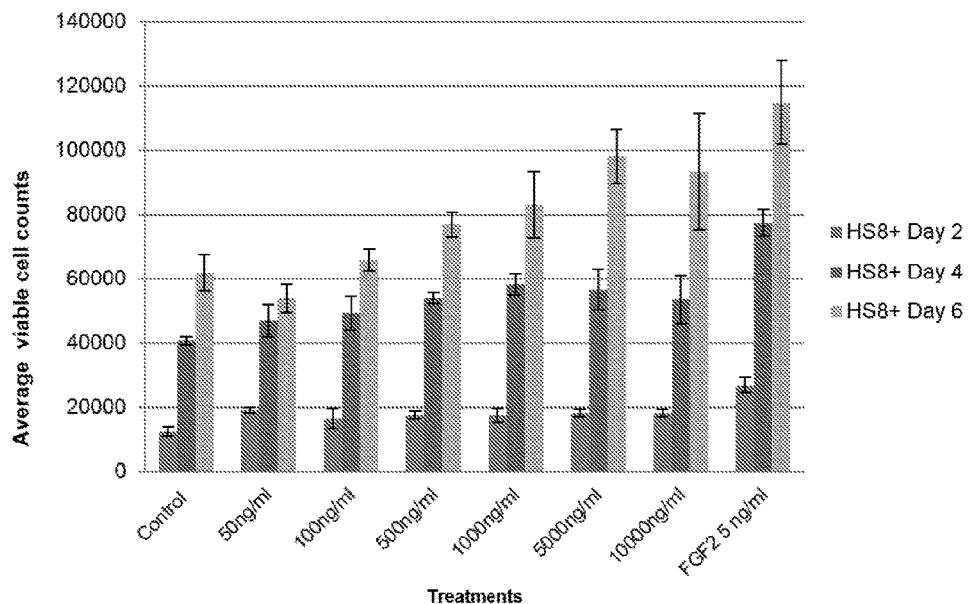
FIG. 12. Graphs showing results of STRO1 (p7) proliferation assay. (A) Viable cell counts on respective days. (B) Cumulative cell growth.
Figure 12B:
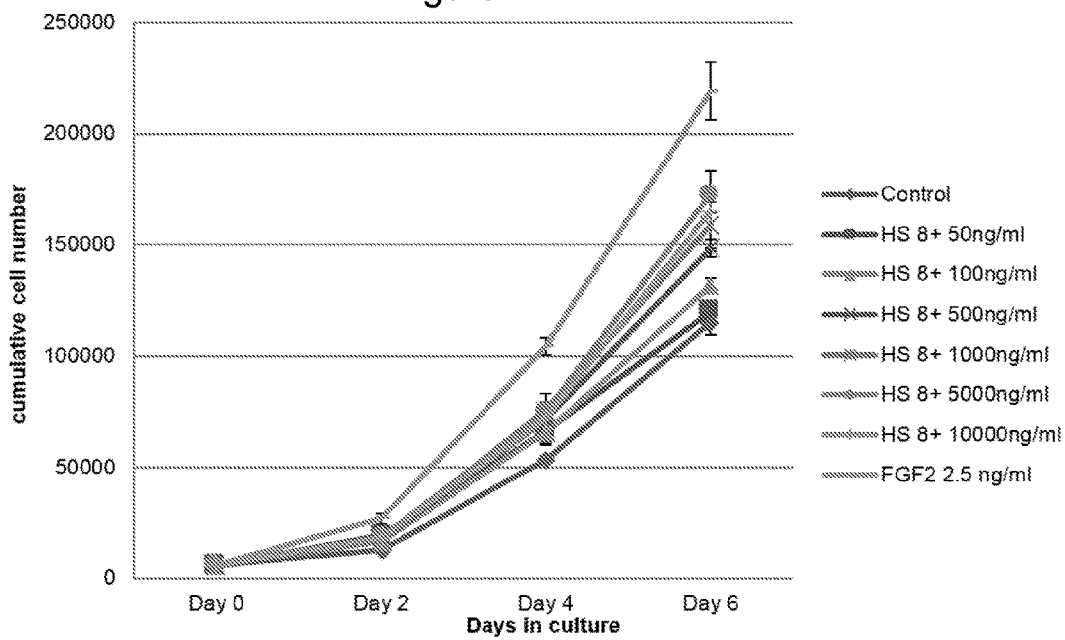
Figure 13A:
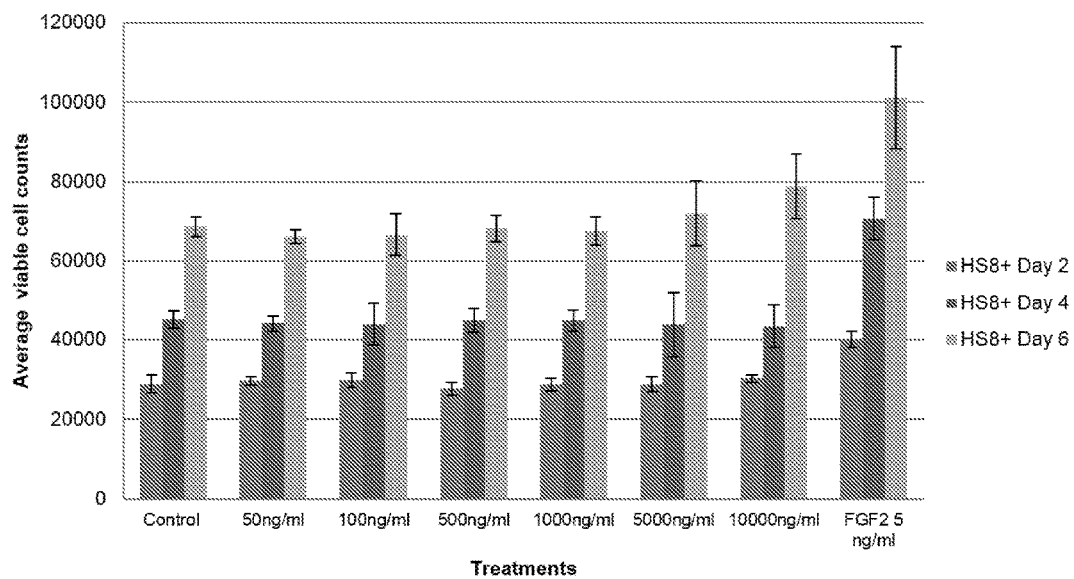
FIG. 13. Graphs showing results of HM21 (p5) proliferation assay. (A) Viable cell counts on respective days. (B) Cumulative cell growth.
Figure 13B:
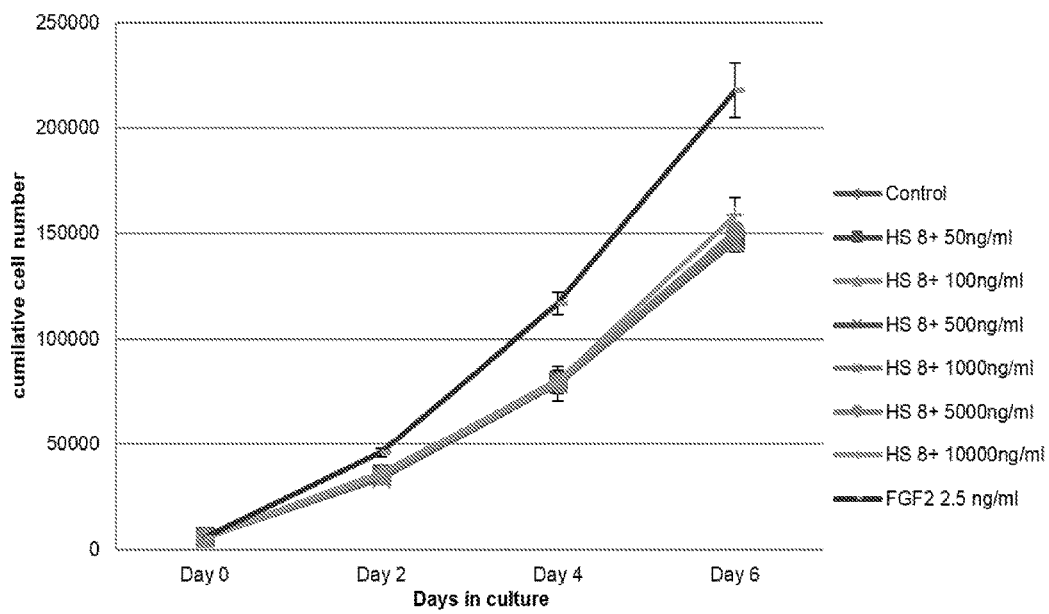

In STRO 1 cells, where the media change was done every 2 days, with HS8+ with increasing concentration increased the viable cell count and by day 6 compared to the controls, 5000 ng/ml was giving the highest counts (FIG. 12). In comparison HM21 cells where the media change was done in every 3 days showing slightly higher counts compared to the controls with 10000 ng/ml by day 6 (FIG. 13).

Figure 14A:
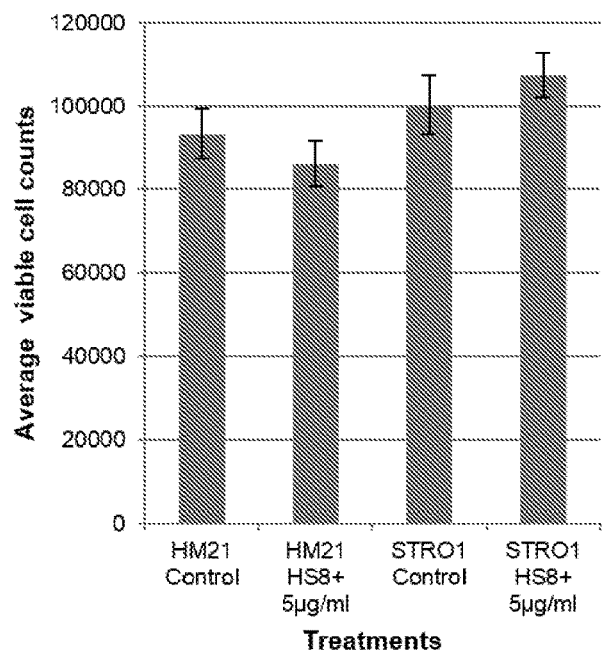
FIG. 14. Graphs showing results of STRO 1 (p5) and HM21 (p5) proliferation assays. (A) Viable cell counts on day 6 with HS8+. (B) STRO1 cell proliferation with different time intervals in media change.
Figure 14B:
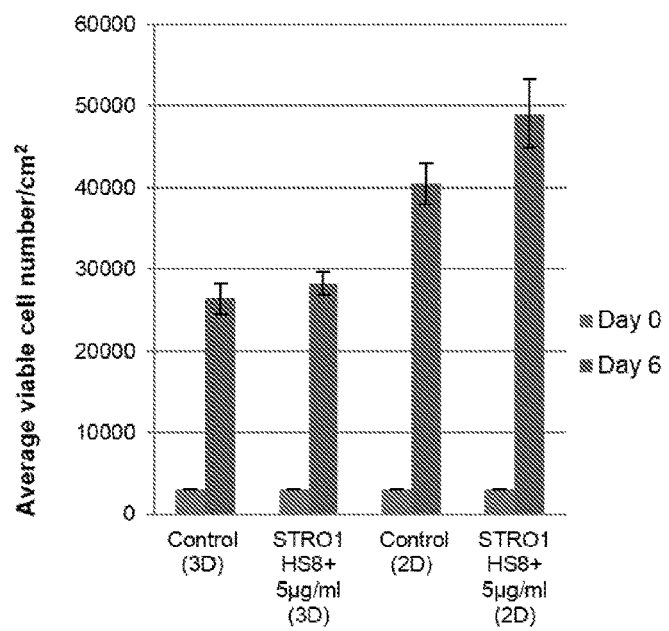

Because of the significant difference observed in the viable cell counts with the two cell types we conducted a proliferation assay with Passage 5 STRO1 and HM21 cells for 6 days and compared to the controls where media change was done in every 3 days. STRO 1 was showed slight higher proliferation counts compared to the HM21 cells but in both cell types, controls and the treated cells were giving almost the same cell counts [(FIG. 14(A)]. Then we calculated STRO1 cells, cell counts/cm$^2$ at day 6 with the data from previous experiment, based on the different time intervals in media change [FIG. 14(B)]. Interestingly, when media change was performed every 2 days compared to every 3 days, gave more cell counts in both controls and in treated cells. In addition, where media change was performed every 2 days the treated cell counts were higher than the untreated controls.

SUMMARY

We used the sequence $^{157}$GHFKDPKRLYCKNGGF$^{172}$ to prepare higher affinity binding HS (HS8) to FGF2 from Porcine Celsus HS by affinity chromatography.

In the glycosaminoglycan (GAG) binding assay results, which clearly showed that HS8+ had the highest affinity of binding to FGF2 compared to other GAG species. In addition the fold difference of Celsus HS: HS8+ at 100 ng/ml FGF2 point, the ratio was 1; 1.51. In heparin beads completion assays considering the percentage of competition, heparin was the most competitive where by adding 50 µg it reached around 13%, followed by HS8+ 43%, Celsus HS 50% and HS8(−) 63%. STRO1+hMSCs isolated by magnetic activated cell sorting and HM21 hMSCs isolated by conventional plastic adherence were used in cell proliferation assays, where higher cell counts were obtained when HS8+ used as a standalone media supplement at a concentration of 5 µg/ml and when the media change done in every 2 days. In conclusion, we now have successfully isolated higher binding affinity heparan sulfate (HS8) to FGF2 from a pool of commercially available heparan sulfate source which possess higher binding affinity to FGF2 and increase the ability to proliferate hMSCs.

In conclusion, we now have successfully isolated higher binding affinity heparan sulfate (HS8) to FGF2 from a pool of commercially available heparan sulfate source and shown that it has higher binding capacity compared with other GAGs including heparin. In addition, HS8+ when used as stand-alone media supplement increases the cell proliferation when media change done in every 2 days. Accordingly, we believe we have addressed the need for high quality ex vivo expanded MSCs by culturing these cells in a heparan sulphate (HS8) engineered to have high affinity for FGF2.

Additional Studies

Isolation of Specific HS (HS8) to FGF2

Although we have successfully achieved in isolating HS8, a higher binding affinity HS to FGF2 we would be further testing the other FGF2 HBD peptides sequences (table 1) in the means of [$^3$H] Heparin Assay, GAG binding assays and cell attachment assays according to Lee et al, 2007.

Binding Affinity Assays

The binding affinity of HS8 has already confirmed by GAG binding plates and will be further validated by dot blot assays and kinetic binding with BIAcore T100 (Cain et al, 2005).

Competition Assays

The results from ELISA method will be further confirmed by western blot method.

Proliferation Assays

Results of proliferation assays will be further validated by using more hMSC lines and also with lower passage of cells. In addition, short term proliferation assays will be carried out by using BRDU (Roche) and WST-1 (Roche) reagents.

Disaccharide Analysis

Disaccharide analysis of HS8 will be carried out using anion exchange chromatography according to Murali et al, 2009 and the composition of the HS8 can be revealed.

Stability of FGF2

Figures 45, 46:
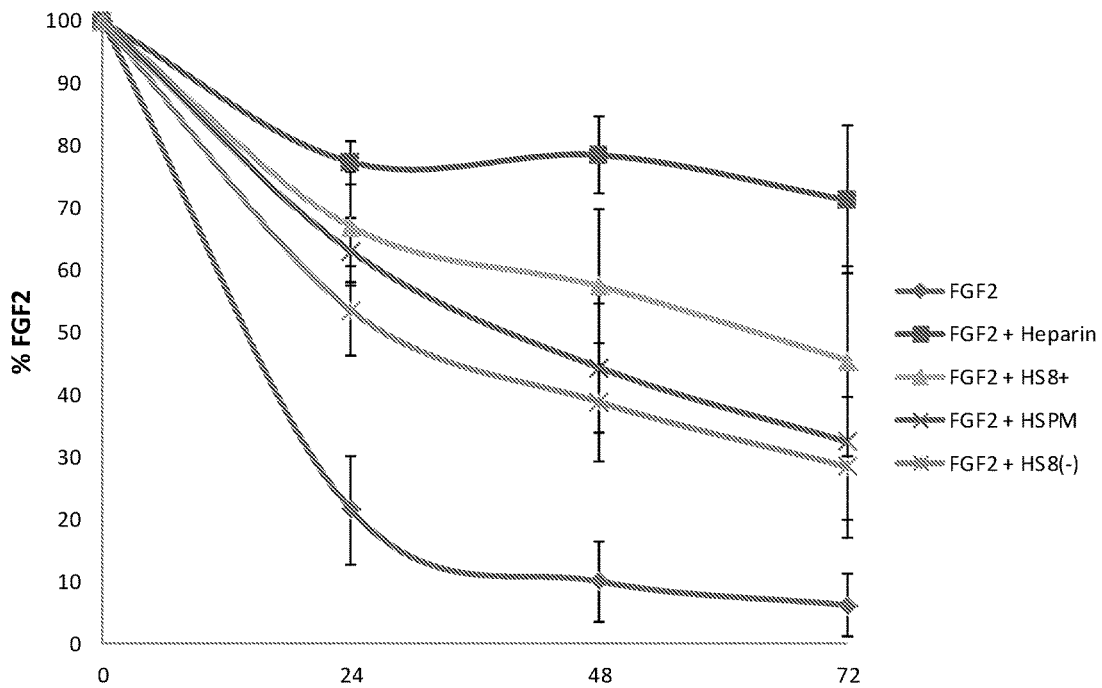
FIG. 45. Table showing percentage disaccharide composition of Celsus, HS, HS3 and HS8.
FIG. 46. Graph showing stability of FGF-2 in the presence of no HS, heparin, HS8, Celsus HS (HSPM) or HS8−. FGF-2 is stabilized in the presence of HS8.
Figure 47:
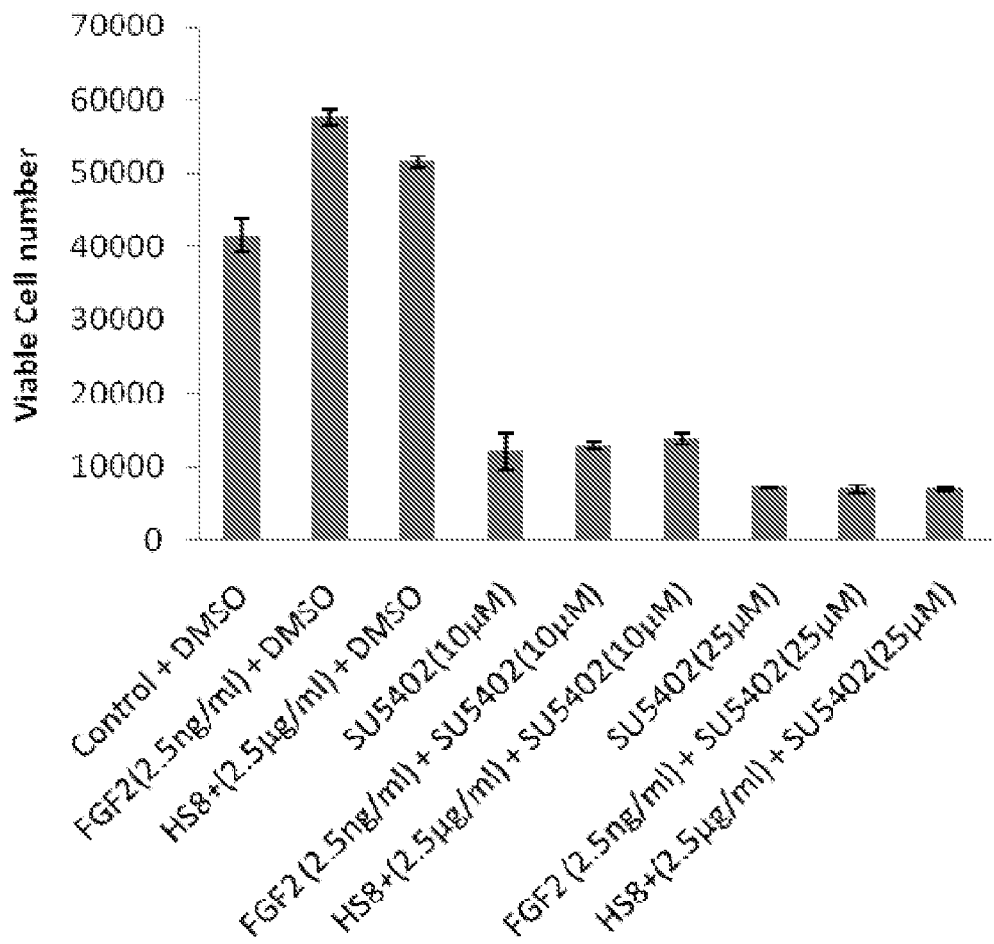
FIG. 47. Graph showing SU5402 (FGFR1 inhibitor) blocks HS8 stimulated proliferation of hMSCs.
Figure 48:
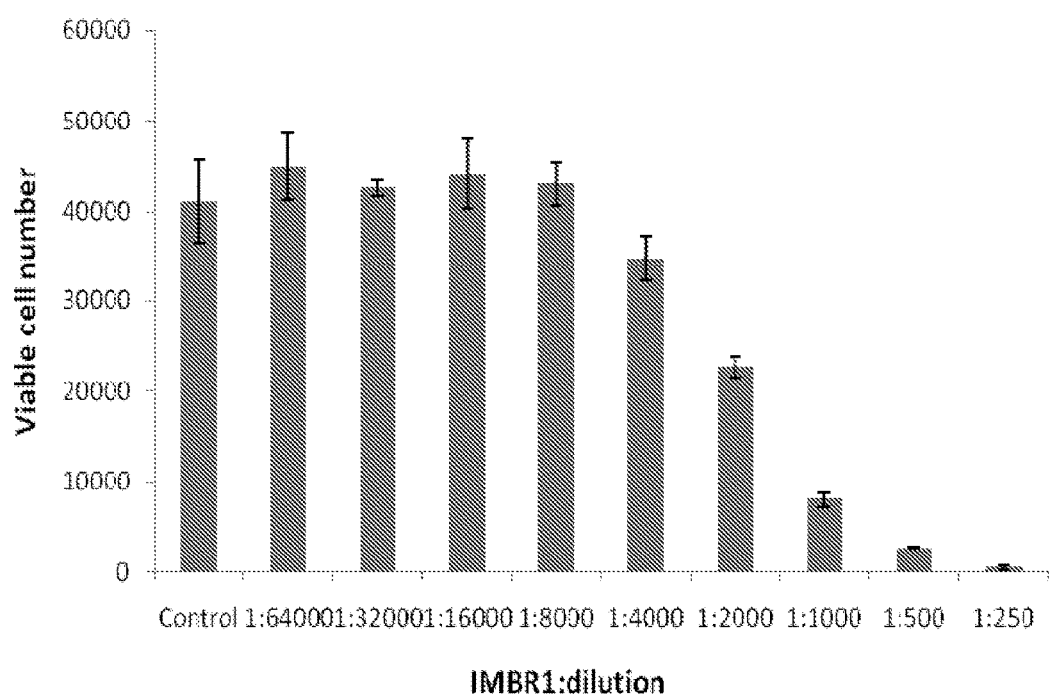
FIG. 48. Graph showing IMB-R1 (FGFR1 neutralizing antibody) inhibits HS8 stimulated proliferation of hMSCs.
Figure 49:
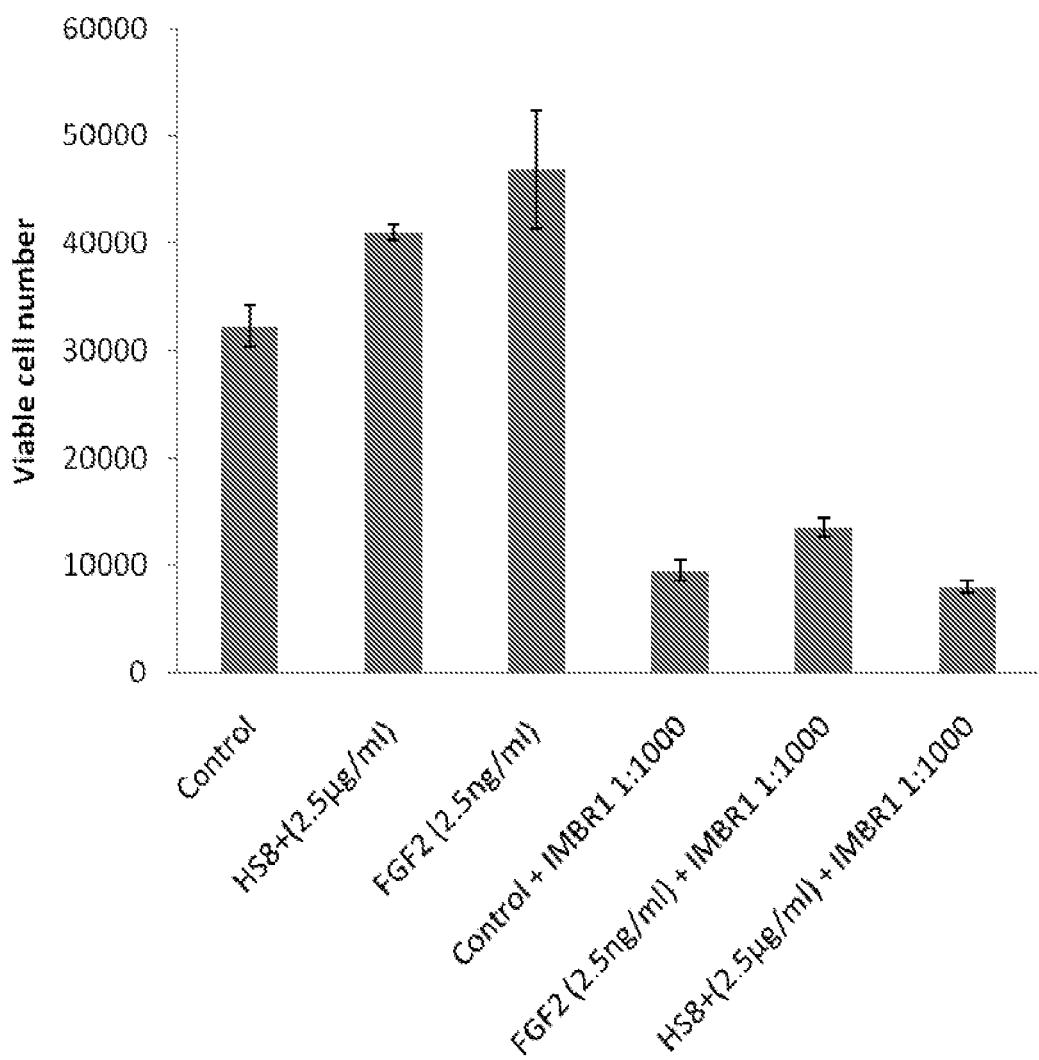
FIG. 49. Graph showing IMB-R1 (FGFR1 neutralizing antibody) inhibits HS8 stimulated proliferation of hMSCs.
Figure 50:
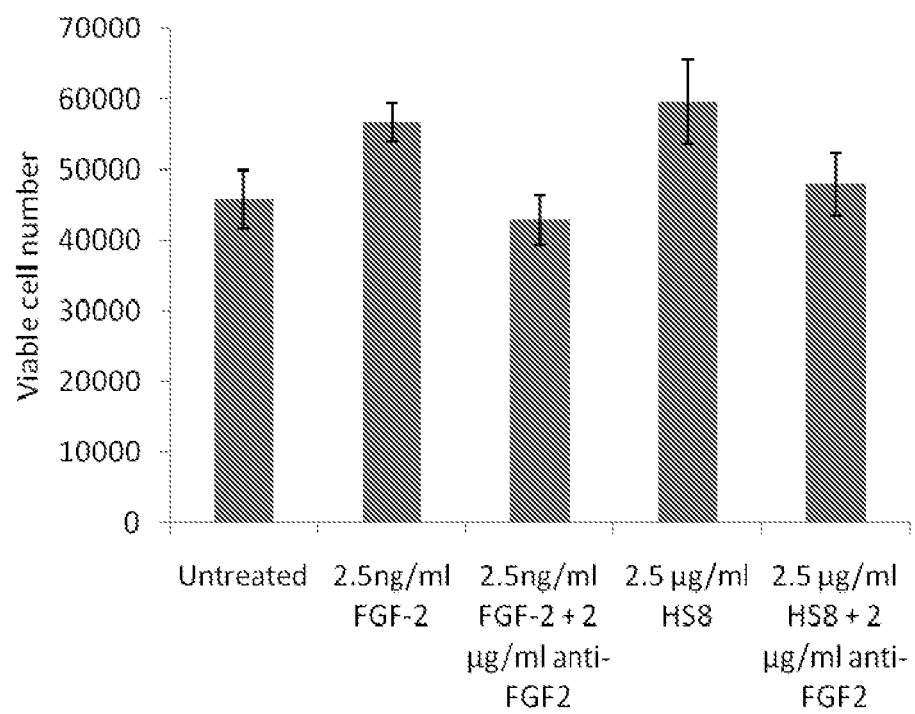
FIG. 50. Graph showing FGF2 neutralizing antibody inhibits HS8 stimulated proliferation of hMSCs.

Stability assays will be carried out as SYPRO assays and FGF2 quantikine assays. In the SYPRO assay, interactions of FGF2 protein with GAGs will be measured as denaturing temperatures of proteins by a specific Sypro Orange dye (Uniewicz et al, 2010). The FGF2 quantikine assays will be carried out as with manufacturer's recommendations (R&D Systems Quantikine® ELISA Cat No. DFB50) in order to measure FGF2 concentrations in cell cultures. Results are shown in FIG. 46.

Check the Biological Activity of hMSC Grown with HS8 In-Vitro

Multipotentiality will be checked for plastic adherence, differentiating to osteogenic, adipogenic and chrondogenic tissues and FACS for surface markers (Dominici et al 2006). The CFU-Fs assays will be performed from bone marrow aspirates and expanded hMSCs with or without HS8 (Cawthon, 2002 and Guillot et al, 2007). Immunomodulatory activity of hMSCs will be assessed by mixed T lymphocyte assays.

Check the Biological Activity of hMSC Grown with HS8 In-Vivo

The cells isolated and grown in the presence of HS8 will be used in mouse bone regeneration models (Zannettino et al, 2010) and also will be used in xenogenic human NOD-SCID mice model of GVHD (Tiasto et al, 2007 and Toubai et al, 2009)

Example 3

The binding capacity of different GAGs for FGF2 was assessed using GAG-binding plates (Iduron). The binding capacity of different GAGs for the heparin-binding growth factors (HBGFs) BMP-2, FGF1, FGF2, FGF7, PDGF-BB and VEGF was also assessed using GAG-binding plates (Iduron). The materials and methodology used are described below.

Figure 15:
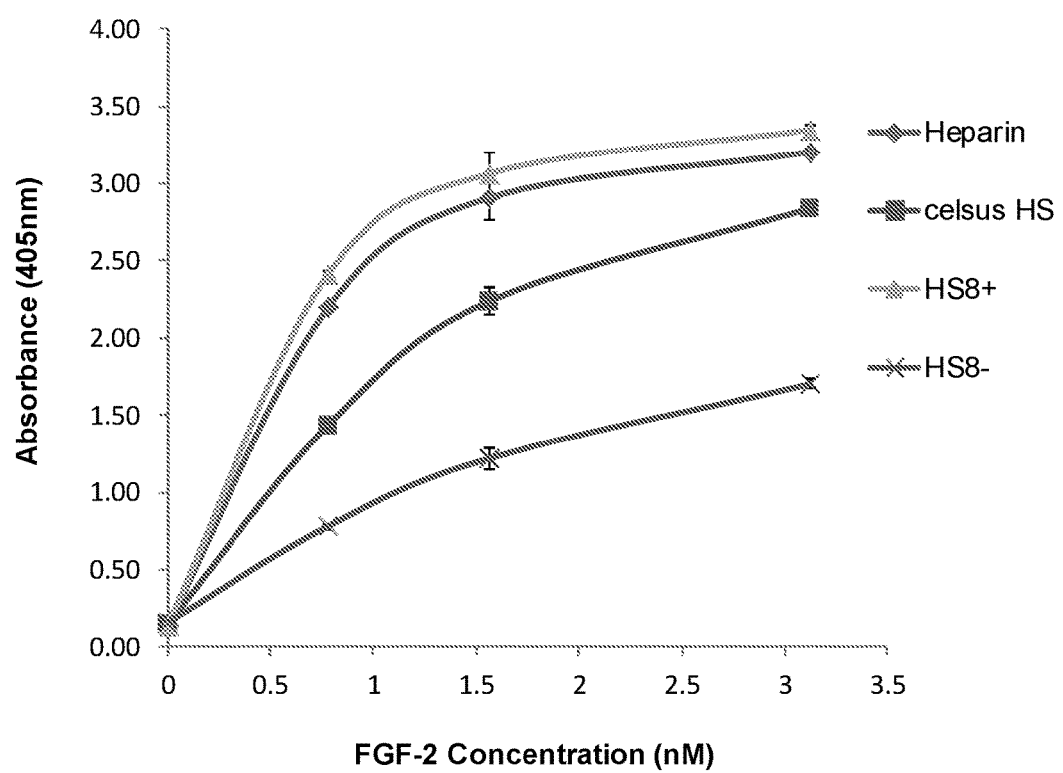
Figure 16A:
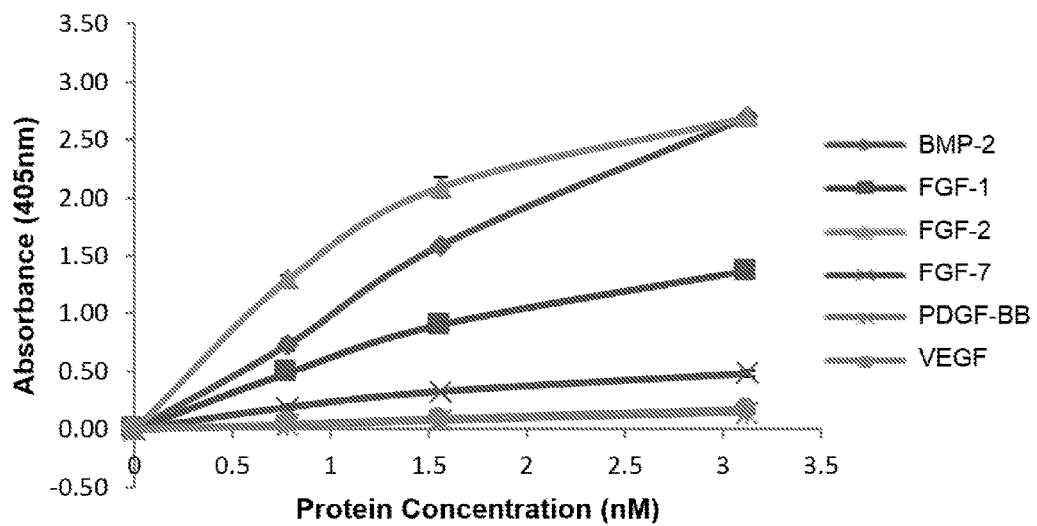
FIG. 16. Graphs showing binding capacity of different GAGs for heparin-binding growth factors (HBGFs) BMP-2, FGF1, FGF2, FGF7, PDGF-BB and VEGF, as assessed by GAG-binding plates (Iduron). (A) Celsus HS, (B) HS8, (C) HS8− fraction, (D) Heparin. The HS8 (HS8+) fraction preferentially binds FGF2 over all of the other HBGFs and even better heparin. HS8− and raw starting Celsus HS display little preference for any of the HBGFs.
Figure 16B:
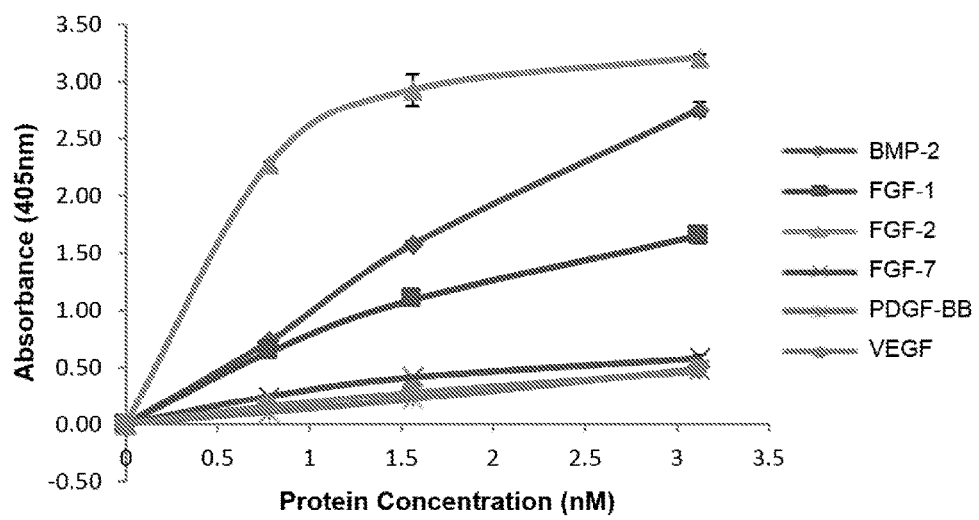
Figure 16C:
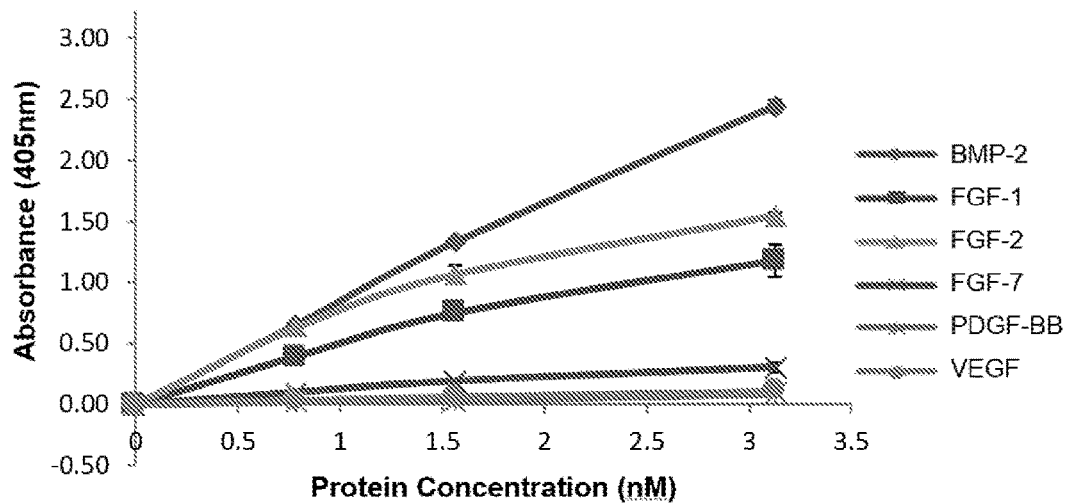
Figure 16D:
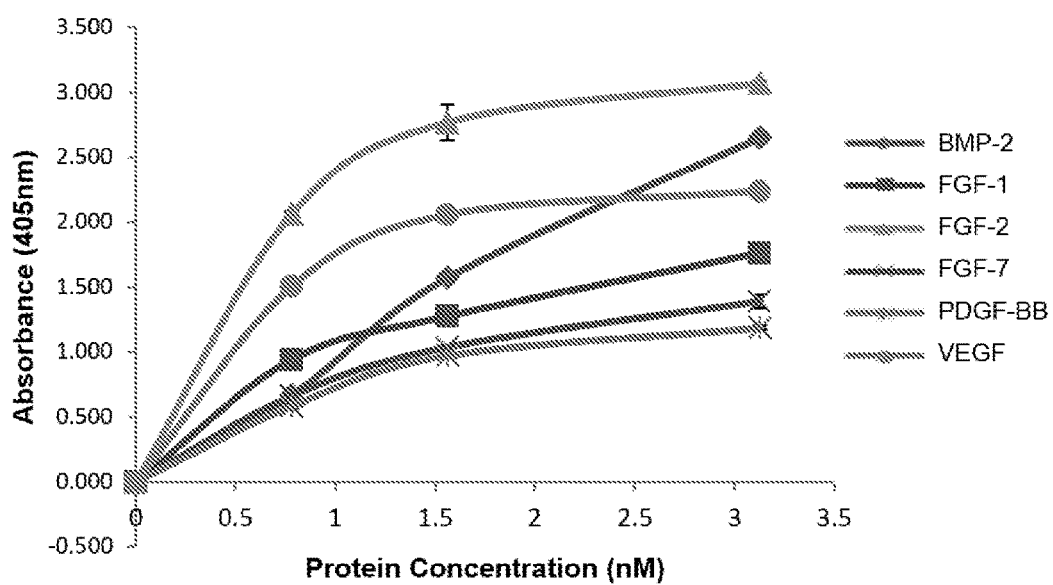

HS8 was found to bind FGF-2 almost as well as heparin, and certainly better than the raw starting Celsus HS and the HS8− flow through fraction (FIG. 15)

HS8 (HS8+) preferentially binds FGF2 over all the other HBGFs tested and has a higher binding capacity for FGF2 than heparin, i.e. HS8 exhibits specific binding to FGF2. HS8− and raw starting Celsus HS displayed little preference for any of the HBGFs tested (FIG. 16).

Materials
1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Proteins from R& D Systems: BMP2—Cat No. 355 BM, FGF 1—Cat No. 231 BC, FGF 2—233 FB, FGF7—Cat No, 251 KG, PDGF BB—Cat No. 220 BB, VEGF—Cat No. 293 VE
5. Antibodies from R & D Systems: BMP2—Cat No. BAM 3552, FGF 1—Cat No. BAF232, FGF 2—BAM233, FGF7—Cat No. BAF251, PDGF BB—Cat No. BAF220, VEGF—Cat No. BAF 293
6. ExtraAvidin-AP (Sigma Cat No. E2636)
7. Sigma FAST p-Nitrophenyl phosphate (Sigma, N2770)

Method
1. Dissolve GAG in SAB (5 µg/ml)
2. Add 200 µl of GAG solution/well into GAG binding plate and incubate overnight at RT protected from light
3. Wash plate carefully 3× with 250 µl/well with SAB
4. Incubate plate with 250 µl/well blocking buffer for 1 hour at 37° C. protected from light
5. Wash plate carefully 3× with 250 µl/well with SAB
6. Dissolve proteins with blocking buffer and perform serial dilution: 0, 0.781, 1.56, 3.125 nM
7. Dispense 200 µl/well of diluted protein to GAG coated plate and incubate for 2 hours at 37° C.
8. Wash plate carefully 3× with 250 µl/well with SAB
9. Add 200 µl/well of 250 ng/ml of biotinylated primary antibody in blocking solution and incubate for 1 hour at 37° C.
10. Wash plate carefully 3× with 250 µl/well with SAB
11. Add 200 µl/well of 220 ng/ml of ExtraAvidin-AP in blocking solution and incubate for 30 min at 37° C.
12. Wash plate carefully 3× with 250 µl/well with SAB
13. Add 200 µl/well of Development reagent: Sigma FAST p-Nitrophenyl phosphate in DI water and incubate for 40 min at RT
14. Read absorbance at 405 nm Example 4

A BrdU incorporation proliferation assay was conducted to establish the effect of HS8 on hMSC proliferation (protocol described below).

Figure 17:
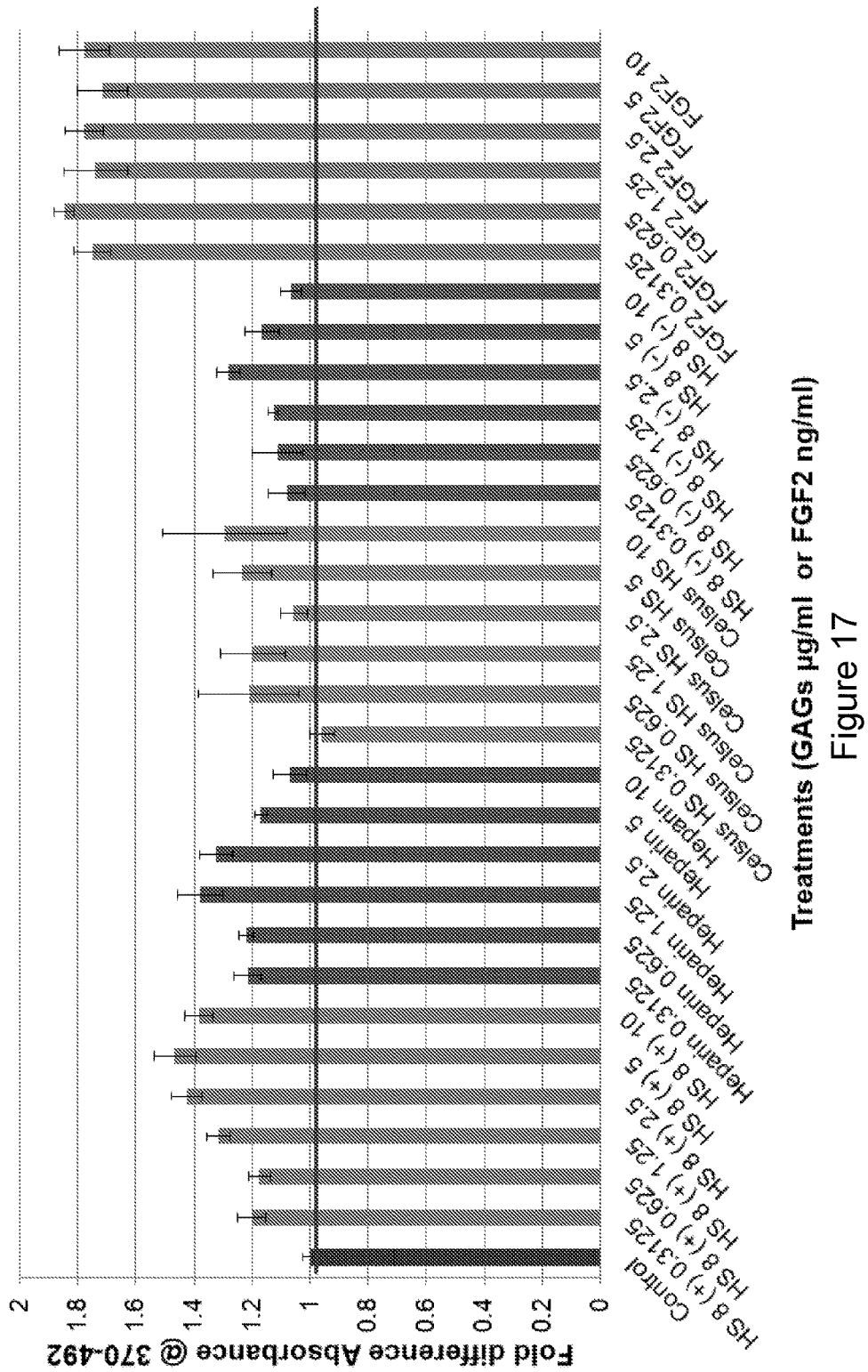
FIG. 17. Graph showing dose-responses of human mesenchymal stem cells to HS8 (HS8+) as monitored by BrdU incorporation over 36 hours. FGF2 is used as a dosing positive control. The HS8+ fraction provides significantly more stimulus than the other GAGs tested.
Figure 18:
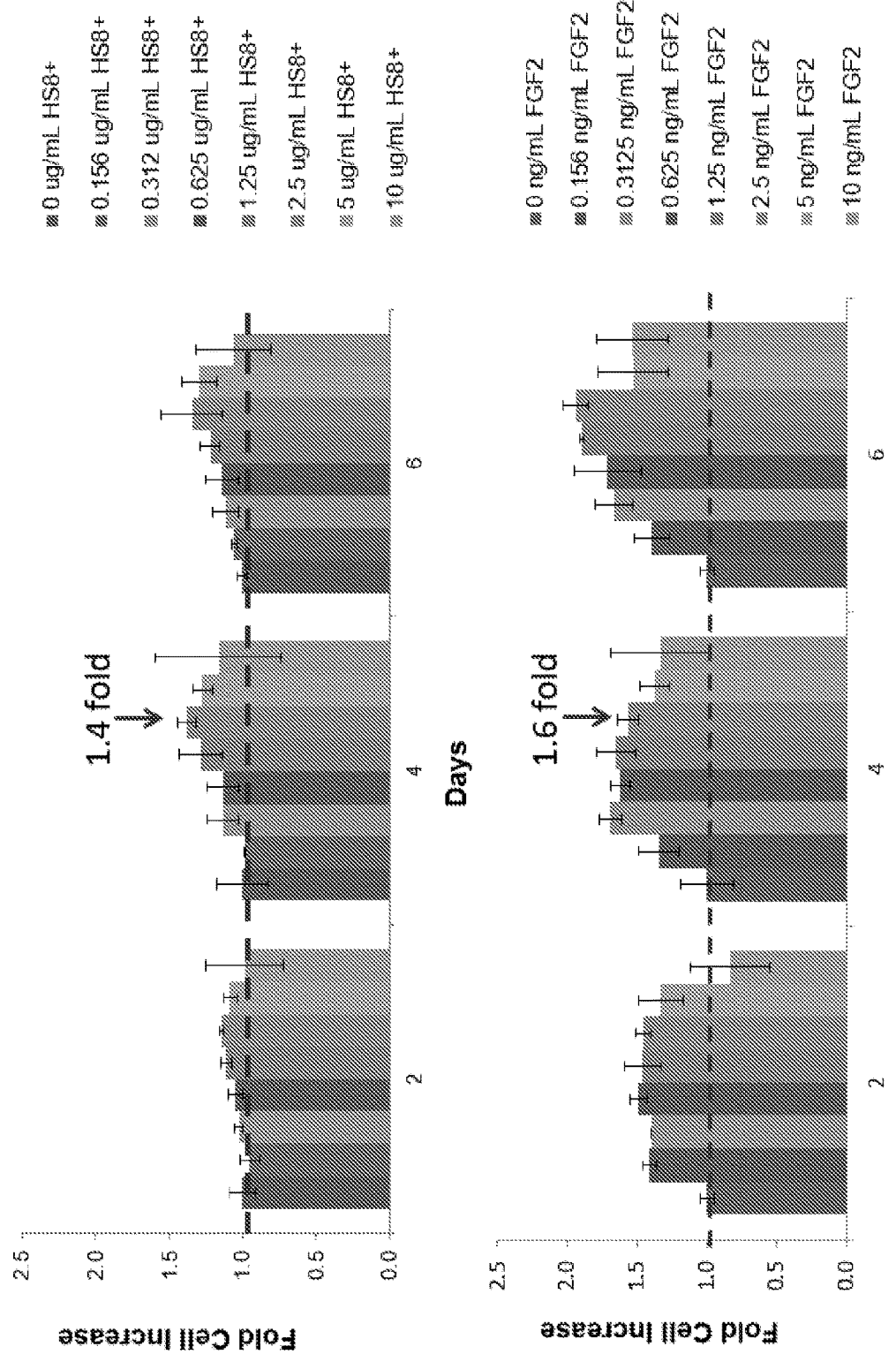
FIG. 18. Graphs showing dose-responses of human mesenchymal stem cells to HS8 (HS8+) (top) and FGF2 (bottom) as monitored by Guava ViaCount (FACS-based) method over the indicated times (in days). FGF2 is used as a dosing positive control (bottom graph). HS8 provides significant stimulus.
Figure 19:
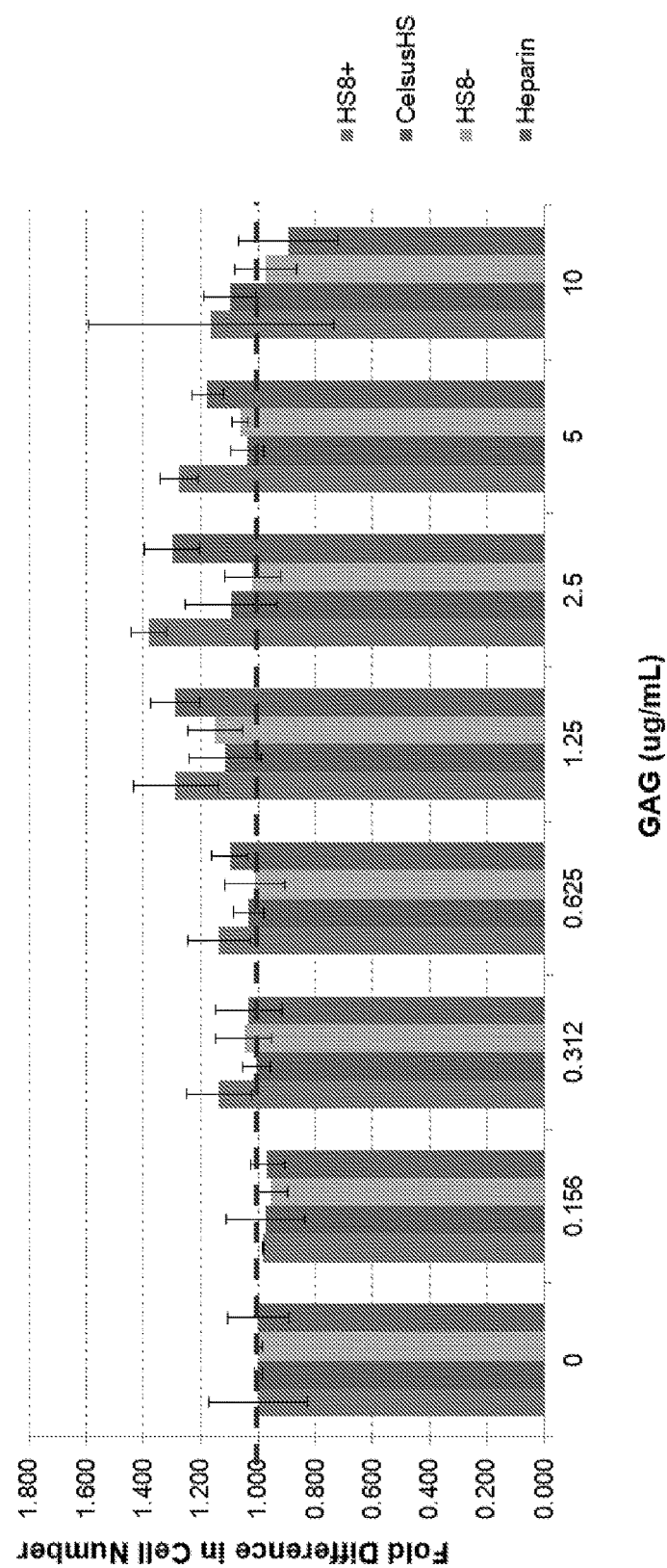
FIG. 19. Graph showing dose-responses of human mesenchymal stem cells to increasing concentrations of different GAGs as monitored by the Guava ViaCount (FACS-based) method over the indicated times (in days). HS8 (HS8+) is trending to higher cell numbers.
Figure 20:
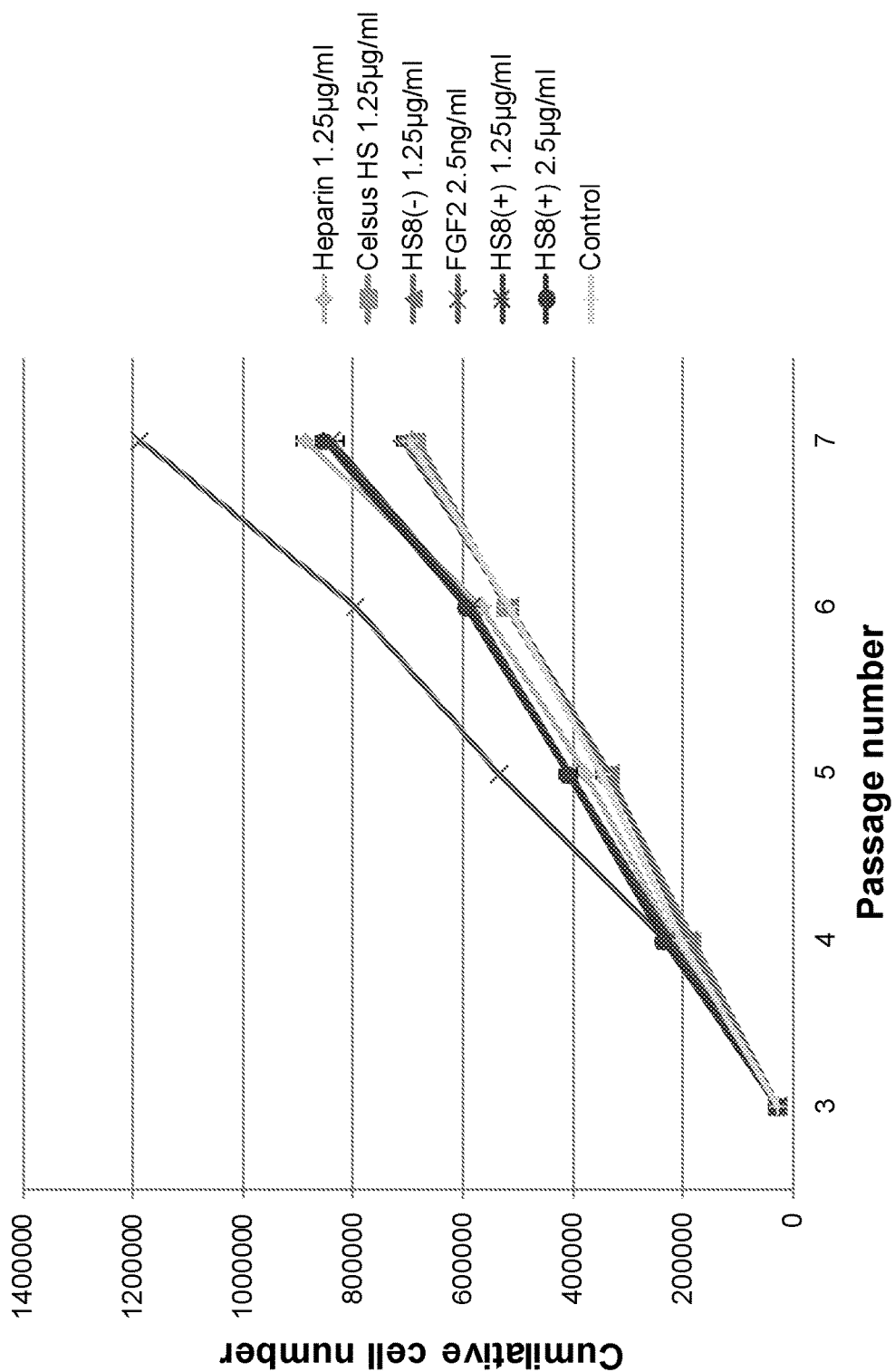
FIG. 20. Graph showing dose-responses of human mesenchymal stem cells to increasing concentrations of different GAGs as monitored by the Guava ViaCount (FACS-based) cell counting method up to 7 passages. FGF2 alone gives highest stimulus; HS8 (HS8+) at both concentrations is trending to higher cell numbers like heparin.
Figure 21A:
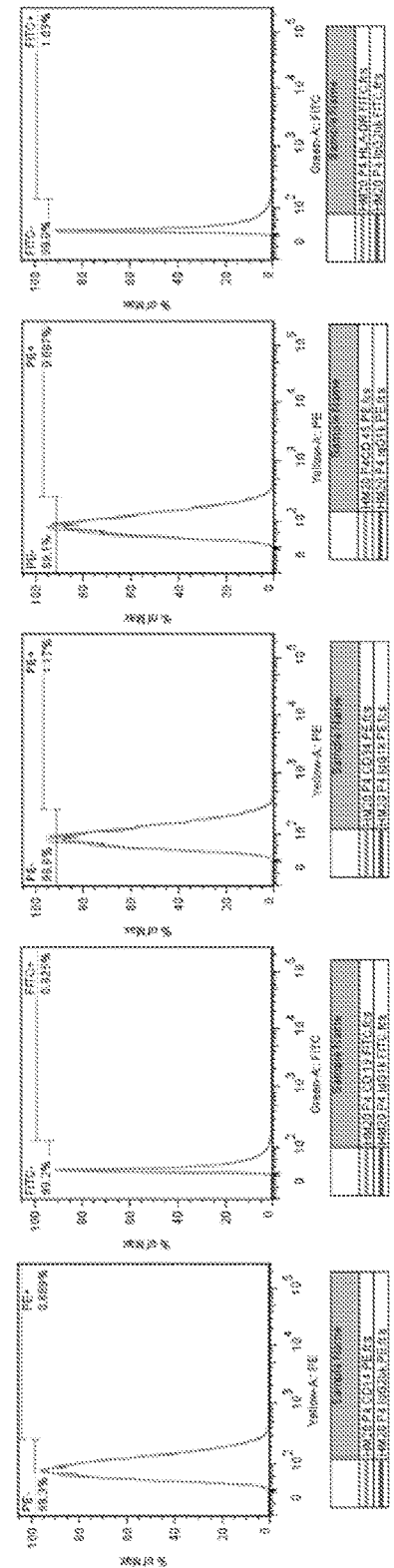
Figure 21B:
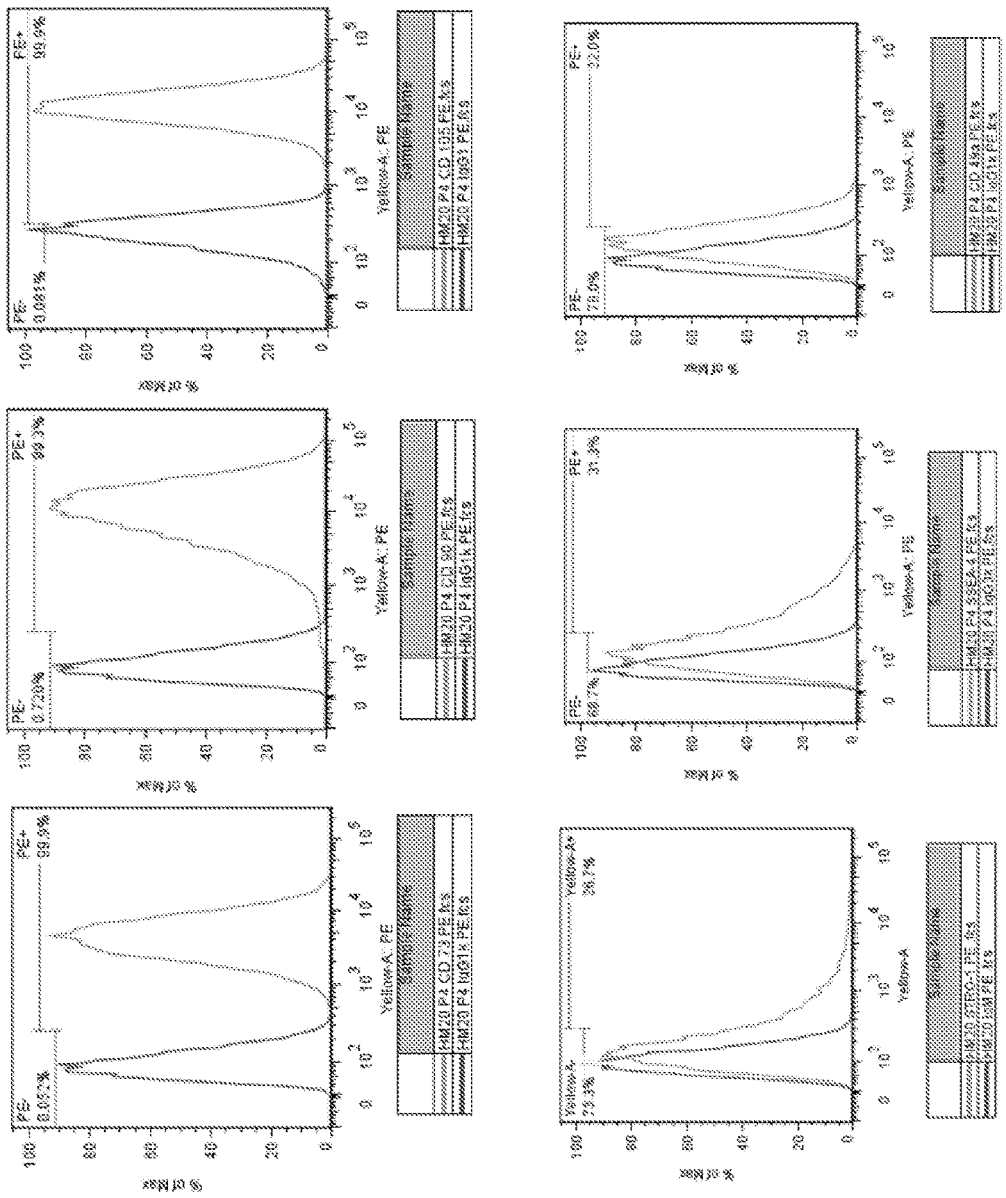
Figure 23A:
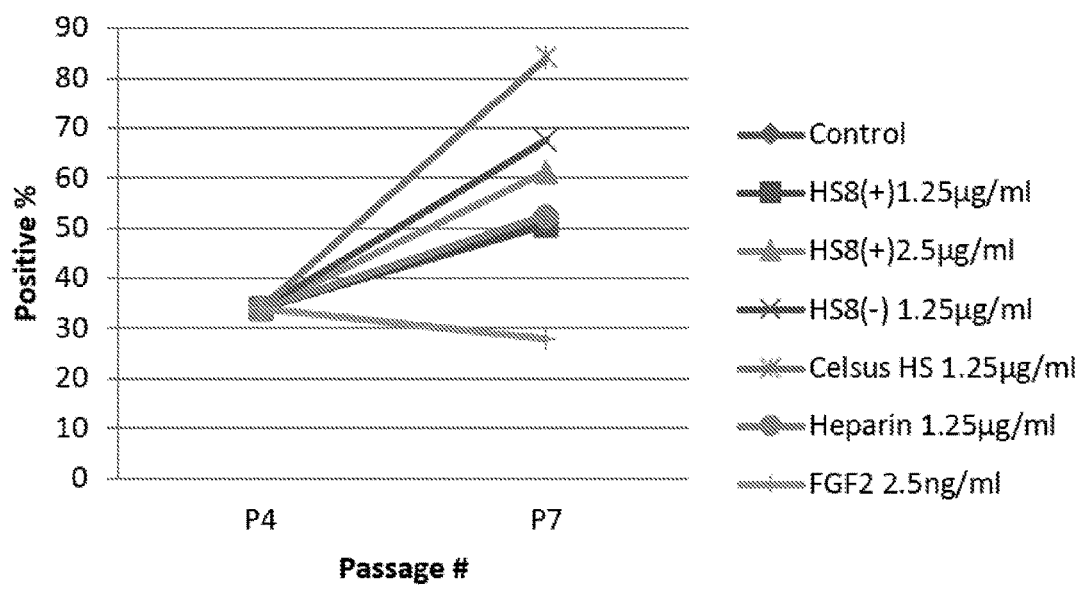
FIG. 23. Graphical representation of FACS immunophenotyped hMSC stem cells grown from 4 to 7 passages in unsupplemented (control), HS8 (HS8+), HS8−, raw Celsus HS, or FGF2 (2.5 ng/ml) alone. (A) CD49a, (B) SSEA-4, (C) STRO-1.
Figure 23B:
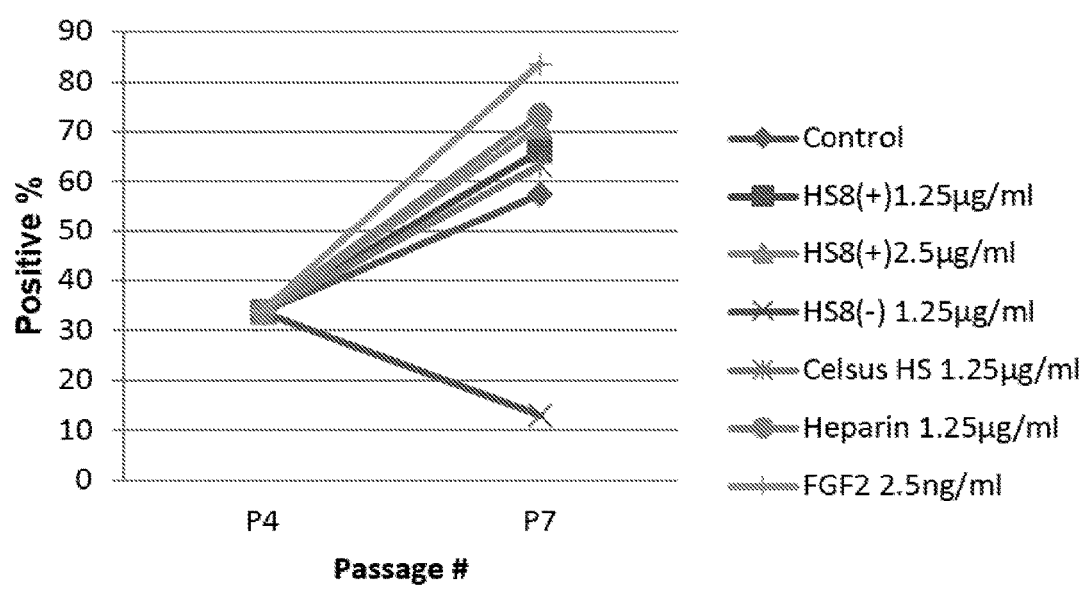
Figure 23C:
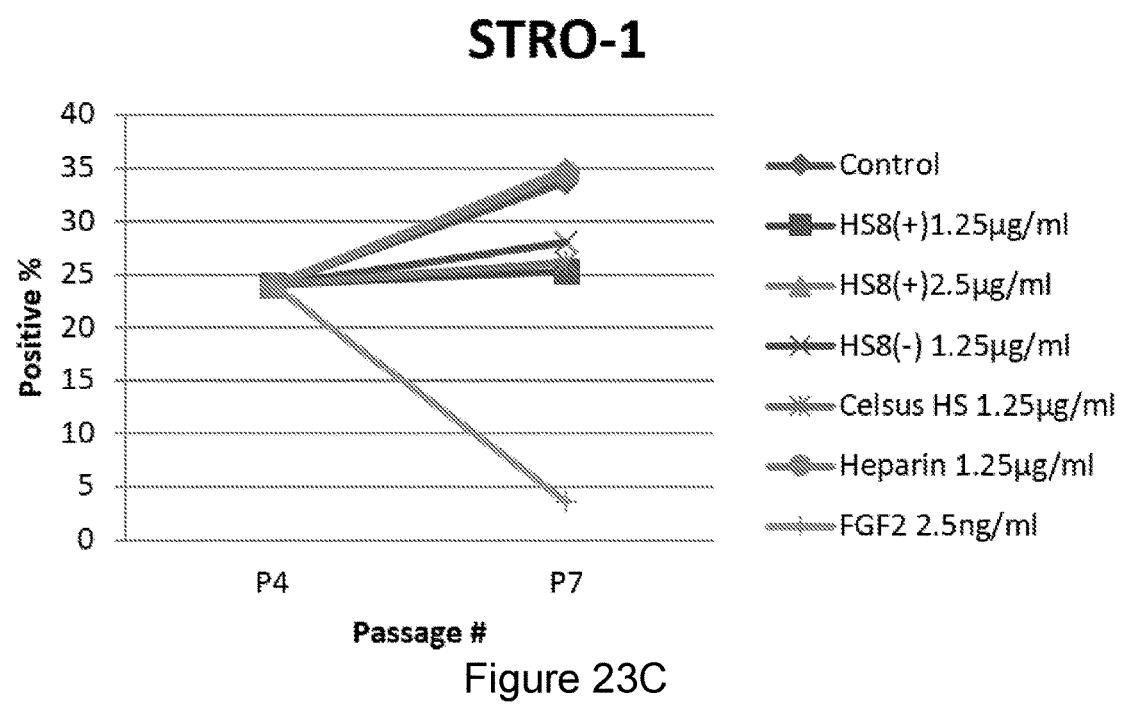

Dose-responses of human mesenchymal stem cells to HS8 (HS8+) were monitored by BrdU incorporation over 36 hours. FGF2 was used as a dosing positive control. HS8+ was found to enhance hMSC proliferation and provide significantly more stimulus than the other GAGs (FIG. 17).

Protocol (Cell Proliferation ELISA, BrdU (Colorimetric) Roche)
1. Cell Seeding—5000 cells in 190 µl of media/well (96 well plate)
2. Media—DM EM with 1000 mg/L+10% Fetal calf Serum (FCS)+1% 2 mM L-gluatamine+1% Penicillin and Streptomycin
3. Incubate for 6 hours in 37° C. and 5% $CO_2$
4. Add different doses of treatments in 10 µl of media for designated wells as in the layout after 6 hours of incubation
5. FGF2 (ng/ml) and GAGs (µg/ml)—10, 5, 2.5, 1.25, 0.625, 0.3125
6. Incubate for 36 hours with treatments in 37° C. and 5% $CO_2$
7. Add BrdU into each well.
8. Label the cells with BrdU for 2 hours in 37° C. and 5% $CO_2$ (Add 20 µl of BrdU labeling solution/well)
9. Remove labeling medium by tapping off the plate
10. Add 200 µl/well FixDenat to the cells and incubate for 30 min at 15-25° C.
11. Remove FixDenat solution thoroughly by flicking and tapping
12. Add 100 µl/well anti-BrdU-POD working solution and incubate for 90 min at 15-25° C.
13. Remove antibody conjugate by flicking off and rinse wells three times with 250 µl/well washing solution (1×PBS)
14. Remove washing solution by tapping.
15. Add 100 µl/well substrate solution and incubate for 30 min at 15-25° C.
16. Measure the absorbance at 370 nm (reference wave length: 492 nm)

Example 5

A FACS based cell proliferation assay was conducted to establish the effect of HS8 on hMSC proliferation (protocol described below).

Dose-responses of human mesenchymal stem cells to HS8 (HS8+) were monitored by Guava ViaCount (FACS-based) method over 6 days. FGF2 was used as a dosing positive control. HS8 was found to enhance hMSC proliferation and provide a significant stimulus.

Cell Proliferation Protocol
Materials
1. HM20 hMSC—Male Hispanic 20 year old donor (purchased from Lonza)
2. FGF 2 (R & D systems. Cat No. 233-FB-025)
3. Maintenance media: DMEM (10 mg/l glucose), 10% FCS, 1% Pen/Strp, 2 mM L-glutamine
4. HS8(+) Batch 2, HS8(−) Batch 2, Porcine mucosal heparan sulfate (Celsus laboratories, USA), Heparin (Sigma Cat No. H3149)
5. Guava Flex reagent (Millipore)

Methods
1. HM20 cells are plated on 24-well plates at 3000 cells/cm² in 500 µl/well media (Day 0)
2. Day 1—Media changed with increasing concentrations of FGF2 (ng/ml) and GAGs (µg/ml)—10, 5, 2.5, 1.25, 0.625, 0.3125, 0.156 in 500 µl of fresh media.
3. Media change every 2 days
4. Cells are harvested at designated time points (Day 2, Day 4 and Day 6)—with 100 µl of trypsin and neutralized with 100 µl of media (t=Day 2) or 300 µl of media (Day 4 and 6)
5. Cells were counted in Guava machine (Guava flex reagent:cell suspension is 1:200)

Example 6—Human Mesenchymal Stem Cell Isolation

Preparation of Human Bone Marrow (BM) Mononuclear Cells

Collection of Human Bone Marrow (BM) and Preparation of BM Mononuclear Cells by Density Gradient Separation
1. Following informed consent, approx 40 mL of human bone marrow (BM) is collected from healthy young volunteers (18-40 y) by aspiration from the posterior iliac crest (hip bone). BM is placed immediately into a preservative-free, sodium heparin-containing 50-mL tube (10,000 units/tube).

2. A 10-μL aliquot is removed and diluted 1:20 into White Cell Fluid (WCF) and nucleated cell content enumerated with a hemocytometer.

3. An equal volume of blocking buffer is then added to the BM aspirate, mixed well, then strained through a 70-μm Falcon cell strainer to remove any small clots and bone fragments.

4. Then 3 mL of Ficoll-Hypaque (Lymphoprep) solution is dispensed into the bottom of approx. 12 round bottom 14-mL polystyrene Falcon tubes and carefully overlayed with 7.5 mL of diluted BM.

5. Tubes are centrifuged at 400 g for 30 min at room temperature.

6. Using a disposable plastic Pasteur pipette, the leucocyte band is recovered from all tubes and pooled into 4×14 mL polypropylene tubes.

7. Cells are diluted with HHF wash buffer and the BMMNC pelleted by centrifugation of the sample at 400 g for 10 min at 4° C.

8. The buffer is aspirated and cells are pooled into one tube.

Isolation of MSCs by Adherence

1. BMNC fractions are seeded into 15 cm dishes in maintenance media (DMEM, 1 g/l glucose, 10% FCS, 2 mM L-glutamine, 50 U/ml penicillin and 50 U/ml streptomycin) and cells allowed to adhere for 3 days before the first media change.

2. The cells are cultured in maintenance medium with a media change every 3-4 days and routinely passaged upon 85% confluence using 0.125% trypsin. On re-plating, cells are seeded at 3,000/cm$^2$. All cultures are maintained in a humidified incubator at 37° C. with 5% $CO_2$.

3. Cells are removed from culture using a non-enzymatic cell dissociation solution (CellStripper, Mediatech, USA) and washed once in PBS before counting. 1×10$^5$ cells are then aliquotted into a 96-well plate and cells pelleted at 450×g for 5 min. Pre-diluted immunophenotyping antibody solutions in 2% FCS/PBS are subsequently added and cells incubated on ice for 20 min. Cells are then washed twice in 2% FCS/PBS before resuspension in 2% FCS/PBS and analysed on a GUAVA PCA-96 bench-top flow cytometer (Guava Technologies Inc., USA). All samples are measured in triplicate.

Magnetic Activated Cell Sorting (MACS) of STRO-1 Positive BMSSC

The use of MACS allows for partial purification of the BMSSC population and the processing of large numbers of BMMNC without compromising high losses in overall stem cells yield. Following density gradient centrifugation, approx 1-2×10$^8$ mononuclear cells are recovered from a BM aspirate of 40 mL. Before immunolabeling, BMMNC are resuspended in 0.5 mL blocking buffer and incubated on ice for approx 30 min to reduce the possibility of Fc receptor-mediated binding of antibodies.

Isolation of STRO-1+ BMSSC Using Magnetic Activated Cell Sorting (MACS)

1. BMMNC are pelleted by centrifugation at 400 g at 4° C. for 10 min and resuspended in 500 μl of STRO-1 supernatant per 5×10$^7$ BMMNC and incubated on ice for 60 min with occasional, gentle mixing.

2. BMMNC are washed twice in HHF wash buffer and then resuspended in 0.5 mL of HHF containing biotinylated goat anti-mouse IgM (μ-chain specific) at a 1/50 dilution and incubated at 4° C. for 45 min.

3. The BMMNC are washed three times in MACS buffer and resuspended in 450 μL of MACS buffer to which 50 μL of streptavidin microbeads are added (10 μL of microbeads/10$^7$ cells in 90 μL MACS buffer). The mixture is incubated on ice for 15 min.

4. After one wash in ice-cold MACS buffer, a small aliquot of cells is removed for flow cytometric analysis (pre sample). The remaining cells are then placed onto a mini MACS column (column capacity of 10$^8$ cells, Miltenyi Biotec, MS column). The STRO-1− cells (negative fraction) are not retained within the column and pass through into a fresh 2 mL polypropylene tube, under gravity into the effluent, while the STRO-1+ cells remain attached to the magnetised matrix.

5. The column is washed 3 times with 0.5 mL MACs buffer to remove any nonspecifically bound STRO-1− cells, which are collected in a fresh 2 mL polypropylene tube.

6. The STRO-1+ cells (positive fraction) are recovered by flushing the column with MACS buffer into a fresh 2-mL polypropylene tube after withdrawing the column from the magnetic field. The STRO-1+ cells are then counted and processed for two-color FACS.

7. Small samples (0.5-1.0×10$^5$ cells) from each of the pre-MACS, STRO-1−, and STRO-1+ fractions are removed into separate 2 mL polypropylene tubes containing 0.2 mL of streptavidin-FITC conjugate (1/50). The cell samples are then incubated for an additional 5 min on ice to enable assessment of the enrichment procedure. A sample of (1.0× 10$^5$ cells) unlabeled pre-MACS cells serves as a negative control.

8. These samples are washed twice in HHF, fixed in FACS Fix solution and subsequently analysed by flow cytometry to assess purity and recovery.

9. At this point, the partially purified STRO-1+ BMSSC can be culture expanded or further purified by two-color FACS.

Assessment of Bone Marrow Quality by Colony-Efficiency Assay

The expected incidence of CFU-F colony in human bone marrow aspirates is approx 5-10 CFU-F per 10$^5$ cells plated.

1. The BMMNC are seeded into 6-well culture plates at 0.3, 1.0, and 3.0×10$^5$ cells per well in α-MEM supplemented with 20% (v/v) FBS, 2 mM l-glutamine, 100 μM l-ascorbate-2-phosphate, 50 U/mL penicillin, 50 mg/mL streptomycin, and β-mercaptoethanol (5×10$^{-5}$ M). Cultures are set up in triplicate and incubated at 37° C. in 5% CO2 and >90% humidity for 12 days.

2. Day 12 cultures are washed twice with PBS and then fixed for 20 min in 1% (w/v) paraformaldehyde in PBS.

3. The fixed cultures are then stained with 0.1% (w/v) toluidine blue (in 1% paraformaldehyde solution) for 1 h then rinsed with tap water and allowed to dry. Aggregates of greater than 50 cells are scored as CFU-F.

Fluorescence Activated Cell Sorting of Highly Purified BMSSC

While all measurable CFU-F are contained within the STRO-1+BMMNC fraction, BMSSC represent only less than 2% of the total STRO-1+ population. The majority of the STRO-1+ cells are glycophorin-A+ nucleated red cells and some CD19+B-cells. Therefore, the selection of BMSSC based on STRO-1 expression alone results in only a partial enrichment of CFU-F (approx 10-fold). Clonogenic BMSSC are all contained within the STRO-1$^{bright}$ cell fraction that can be further discriminated by dual-color FACS based on the expression of markers that are absent on nucleated red cells and lymphocytes, particularly CD106 and CD146. The methods described below enable the isolation of a minor subpopulation of the total STRO-1+ cell fraction, STRO-1$^{bright}$/CD106+ BMMSC (1.4%±0.3; n=20), in which 1 in every 2-3 cells plated have the capacity to form a CFU-F. This level of enrichment is almost 5,000-fold higher than the average incidence of CFU-F observed with unfractionated BMMNC (1 CFU-F per 10,000 cells plated).

Isolation of STRO-1bright/CD106+ BMSSC Using Flow Cytometric Cell Sorting (FACS)

1. Before immunolabeling, the MACS-isolated STRO-1+ cell BMMNC (routinely $2\text{-}5\times10^6$ cells—from $1\times10^8$ BMMNC) are resuspended in 0.5 mL HHF in preparation for 2-color immunofluorescence and FACS.

2. Approx $3\text{-}5\times10^5$ MACS-isolated STRO-1+ cell are dispensed into 3 appropriately labeled tubes, to which the following are added:
   (i) No primary antibody (double negative control), kept on ice.
   (ii) Streptavidin-FITC conjugate (1/100 dilution in HFF) incubated on ice for 30 min (FITC control). The cells are then washed twice in HHF.
   (iii) 0.5 mL of murine IgG anti-human CD106 (VCAM-1) diluted to 20 μg/mL in HFF. The STRO-1+ cells are incubated on ice for 30 min, washed twice in HHF and resuspended in 0.2 mL of PE-conjugated goat anti-mouse IgG (γ-chain specific), (PE control). The sample is incubated and washed then resuspended in HFF.
   (iv) The remaining $1\text{-}2\times10^6$ MACS-isolated STRO-1+ cells are resuspended in 0.5 mL murine IgG anti-human CD106 (VCAM-1) and incubated as above, washed twice in HHF and resuspended in 0.2 mL of PE-conjugated goat anti-mouse IgG (γ-chain specific) and Streptavidin-FITC conjugate (1/100 dilution in HHF), then incubated on ice for 30 min (sorting sample). The cells are then washed as before then resuspended in HHF.

3. The samples are resuspended at a concentration of $1\times10^7$ cells per mL in HHF before sorting on any sorter fitted with a 250 MW argon laser emitting light at a wavelength of 488 nm able to simultaneously detect FITC and PE. Samples (i-iii) are used to establish compensation for both FITC and PE. 5. Sorted STRO-1$^{bright}$/VCAM-1+ cells from sample (iv) are collected in tubes containing appropriate growth media and mixed. 6. A cell count is performed as described above. The sorted cells are then cultured.

Ex Vivo Culture of Human BMSSC

Serum Replete Medium

1. The STRO-1$^{bright}$/CD106+ isolated BMSSC populations (at $1\text{-}3\times10^4$ per cm$^2$) are cultured in tissue culture flasks or plates containing α-modification of Eagle's Medium (α-MEM) supplemented with 20% foetal bovine serum, 100 μM l-ascorbate-2-phosphate, 2 mM l-glutamine, 50 U/mL penicillin and 50 μg/mL streptomycin at 37° C. in 4% CO2 at relative humidity of >90% for 2 wk. Primary BMSSC populations are passaged when the cultures achieve 80-90% confluency.

2. Adherent cultures are washed 1× with serum free HBSS and the cells liberated by enzymatic digestion by the addition of 2 mL of 0.5% Trypsin/EDTA solution per T75 flask for 5-10 min at 37° C.

3. Cell viability is assessed by preparing a 1:5 dilution of single cell suspension in 0.4% trypan blue/PBS, and the number of viable cells determined using a haemocytometer.

4. BMMSC single cell suspensions are pooled and re-seeded at $0.5\text{-}1.0\times10^4$ per cm$^2$ in α-MEM growth medium supplemented with 10% FBS, 100 μM l-ascorbate-2-phosphate, 2 mM l-glutamine, 50 U/mL penicillin and 50 μg/mL streptomycin and incubated at 37° C. in 5% CO$_2$ at relative humidity of >90%. Cultures are fed twice weekly by aspirating out the medium and replacing with an equal volume of freshly prepared medium warmed to 37° C.

Serum Deprived Medium

This method is a modification of the serum deprived medium (SDM) developed initially for the growth of hematopoietic progenitor cells.

1. Fibronectin-coated plates or flasks are prepared by precoating with 5 μg per cm$^2$ fibronectin solution for 90 min at room temperature. After this, the fibronectin solution is aspirated off and the culture vessels washed once with sterile PBS before seeding with cells.

2. The STRO-1$^{bright}$/CD106+ isolated BMSSC populations (at $1\text{-}3\times10^4$ per cm$^2$) are cultured in the fibronectin-coated tissue culture flasks or plates suspended in media containing α-MEM supplemented with 2% (w/v) bovine serum albumin (Cohn fraction V), 10 μg/mL recombinant human insulin, human low density lipoprotein, 200 μg/mL iron saturated human transferrin, 2 mM l-glutamine, dexamethasone sodium phosphate ($10^{-8}$ M), 100 μM l-ascorbic acid-2-phosphate, β-mercaptoethanol ($5\times10\text{-}5$ M), 10 ng/mL platelet derived growth factor-BB, 50 U/mL penicillin and 50 μg/mL streptomycin.

3. The cultures are then incubated at 37° C. in 4% CO$_2$ at relative humidity of >90% for 2 wk. Primary BMSSC populations are passaged when the cultures achieve 80-90% confluency.

Cryopreservation of Ex Vivo Expanded MSCs

1. Routinely, single cell suspensions of culture expanded MPC are prepared by trypsin/EDTA digest as described above. The cells are then diluted and washed in cold HFF.

2. The cell pellet is resuspended at a concentration of $1\times10^7$ cells per mL in FBS and maintained on ice. An equal volume of freeze mix (20% DMSO in cold FBS) is then added gradually while gently mixing the cells to give a final concentration of $5\times10^6$ cells per mL in a 10% DMSO/FBS. One-milliliter aliquots are then distributed into 1.8-mL cryovials precooled on ice, then frozen at a rate of −1° C. per minute using a rate control freezer.

3. The frozen vials are then transferred to liquid nitrogen for long-term storage. Recovery of the frozen stocks is achieved by rapid thawing the cells in a 37° C. water bath. The cells are then resuspended in cold HFF and spun at 280 g for 10 min.

4. To assess viability of the cells, a 1:5 dilution is prepared in 0.4% trypan blue/PBS, and the number of cells determined using a haemocytometer. Typically this procedure gives viabilities between 80-90%.

Example 7—Colony-Forming Units-Fibroblastic (CFU-F) Assay

Figure 24A:
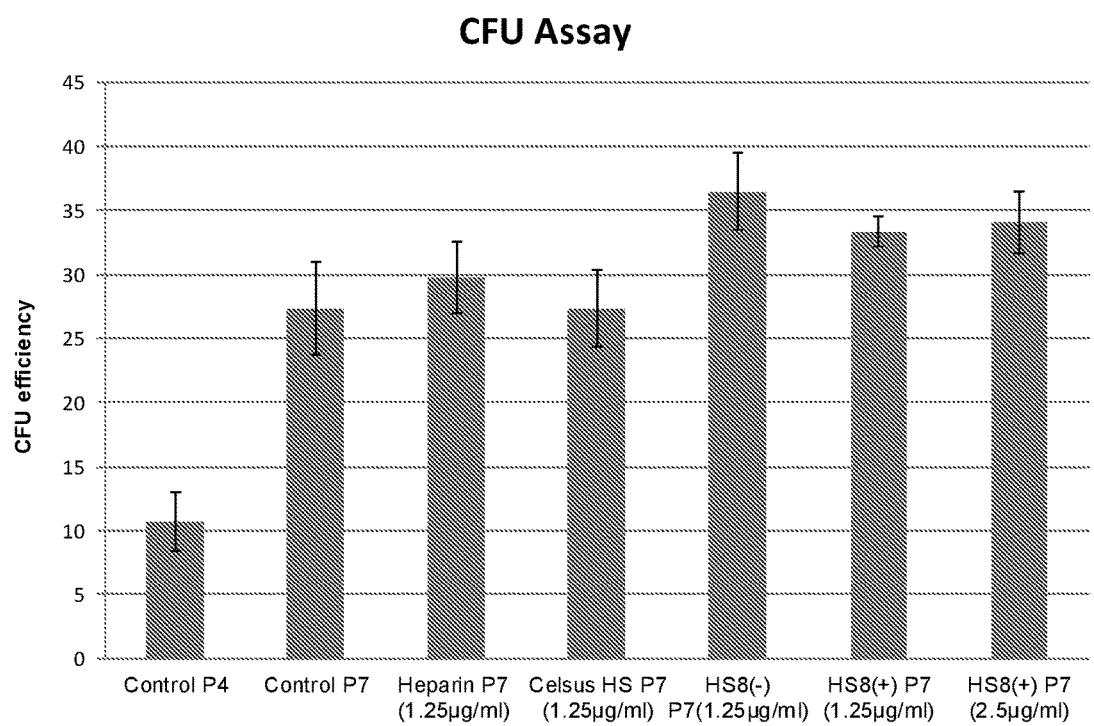
FIG. 24. (A) Graphical representation and (B) micrographs of culture plates of hMSC CFU assay following culture of hMSCs grown from 4 to 7 passages (P4, P7) in culture media containing unsupplemented (control), Heparin, Celsus HS, HS8−, and HS8 (HS8+).
Figure 24B:
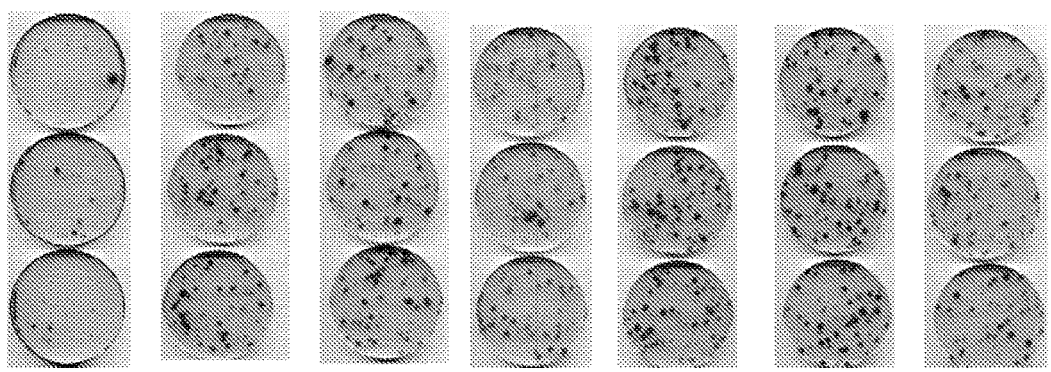

The CFU-F property of hMSC was assessed using the methodology described below. hMSCs were grown in one of unsupplemented control media for 4 passages and then grown in one of unsupplemented control media, or control media plus one of Heparin (1.25 μg/ml), Celsus HS (1.25 μg/ml), HS8− (1.25 μg/ml), HS8 (HS8+) (1.25 μg/ml) or HS8 (HS8+) (2.5 μg/ml). Results are shown in FIGS. 24A and 24B.

Materials 1. hMSC—(purchased from Lonza).
2. Maintenance media: DMEM (1000 mg/L glucose), 10% FCS, 1% Pen/Strep, 2 mM L-glutamine.
3. Crystal Violet 0.5% in 100% Methanol.

Methods

1. MSCs are plated in triplicate in 100×15 mm petri dishes at 150 cells/cm$^2$ with 10 ml/dish maintenance media.

Figure 25:
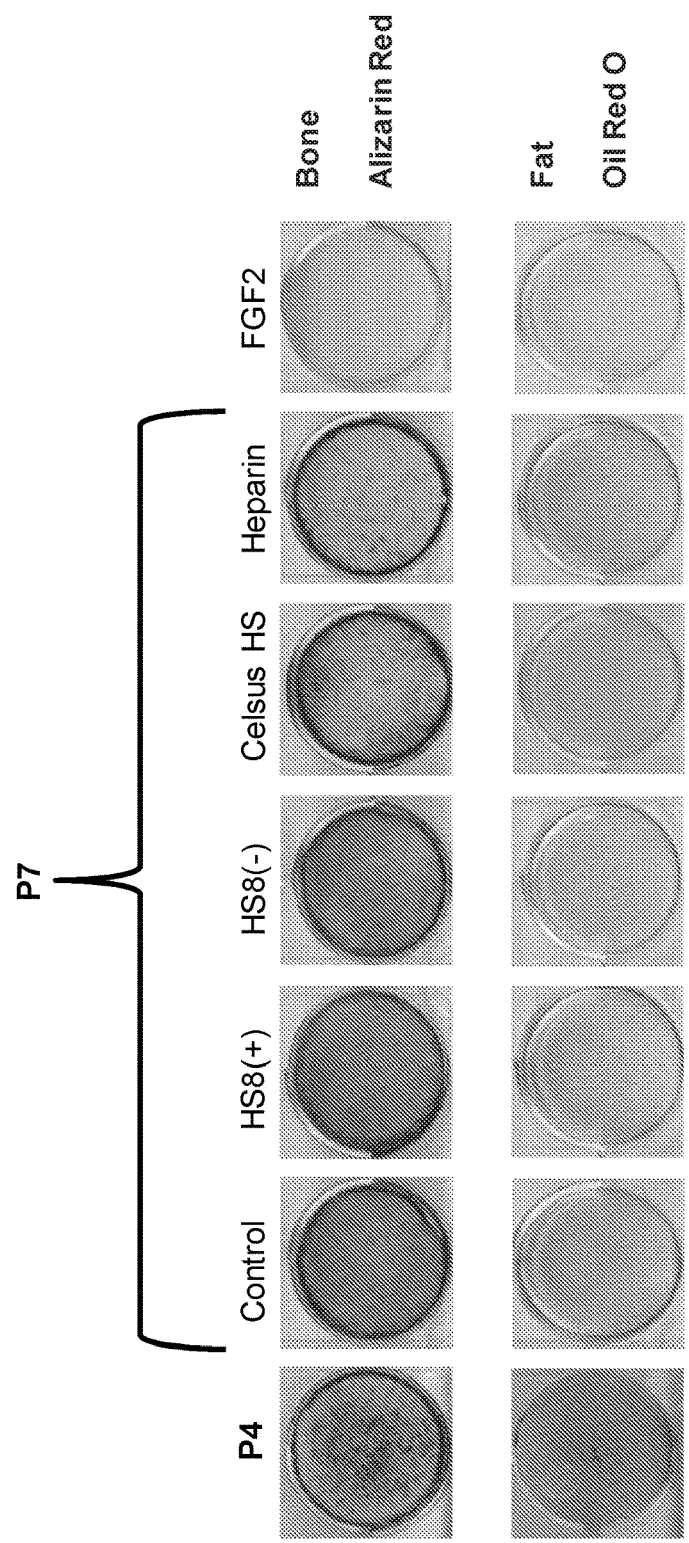
FIG. 25. Micrographs showing ability of hMSCs to differentiate into bone (top, Alizarin red) and fat (bottom, Oil Red 0) cells, following culture of hMSCs grown from 4 to 7 passages (P4, P7) in culture media containing unsupplemented (control), HS8 (HS8+), HS8−, Celsus HS, Heparin and FGF2.

2. Cells were cultured for 14 days with media change at day 7.
3. At Day 14 the plates were stained with crystal violet (0.5% in 100% Methanol) as below:
   a. Remove media and wash twice with PBS
   b. Add 10 ml/dish of crystal violet and incubate for 30 minutes
   c. Wash once with PBS and once with $H_2O$ and dry the plates
   d. Colonies with more than 50 cells that were not in contact with other colonies were counted Example 8—Multipotent Characteristic of MSCs Maintenance of the multipotent character of MSCs was tested by assaying for ability of the MSCs to differentiate into bone (osteogenesis) and fat (adipogenesis), according to the methodology described below. Results are shown in FIG. 25.

Cells

Passage 4 cells (P4)—hMSCs cultured in normal maintenance media

Passage 7 cells (P7)—hMSCs cultured from P4 to P7 in normal maintenance media containing the one of the following treatments:
HS8 (HS8(+)) 2.5 ug/mL
HS8(−) 1.25 ug/mL
Celsus HS 1.25 ug/mL
Heparin 1.25 ug/mL
FGF2 1.25 ug/mL Osteogenic Differentiation Materials
1. hMSC—(purchased from Lonza)
2. Maintenance media: DMEM (1000 mg/L glucose), 10% FCS, 1% Pen/Strep, 2 mM L-glutamine
3. Treatment maintenance media: DMEM (1000 mg/L glucose), 10% FCS, 1% Pen/Strep, 2 mM L-glutamine, 10 nM dexamethazone, 10 mM β-glycerol-phosphate and 25 μg/mL L-ascorbate-2-phosphate
4. Paraformaldehyde 4% in PBS
5. Alizarin Red Solution: 1.37 g in 100 mL $H_2O$; pH 4.1-4.3

Methods
1. Cells were seeded (3,000 cells/$cm^2$) in 6-well plates for 24 h
2. Changed media for control wells with maintenance media
3. Changed media for treated wells with maintenance media containing 10 nM dexamethazone, 10 mM β-glycerol-phosphate and 25 μg/mL L-ascorbate-2-phosphate
4. All cells then cultured for 28 days with media change in every 3 days
5. Cells were then stained with Alizarin Red:
   a. Wash three times with PBS
   b. Fix cells with 4% Paraformaldehyde for 10 min
   c. Wash three times with $ddH_2O$
   d. Add Alizarin Red solution to the cells and incubate for 30 min, slowly shaking
   e. Wash three times with $ddH_2O$
   f. Air dry the stained cells Adipogenic Differentiation Materials
1. hMSC—(purchased from Lonza)
2. Adipocyte maintenance media: DMEM (4500 mg/L glucose), 10% FCS, 1% Pen/Strep, 2 mM L-glutamine
3. Adipocyte treatment media: DMEM (4500 mg/L glucose), 10% FCS, 1% Pen/Strep, 2 mM L-glutamine, 1 μM dexamethazone, 10 μM insulin, 20 μM indomethazine and 115 μg/mL 3-isobutyl-1-methylxanthine
4. Paraformaldehyde 4% in PBS
5. Oil Red O Solution: 0.36% in 60% isopropanol Methods
1. Cells were seeded (18,000/$cm^2$) in 6-well plates in triplicates
2. Cells were cultured to confluence
3. Changed media for control wells with adipocyte maintenance media (4500 mg/L glucose)
4. Changed media for treated wells with adipocyte treatment media containing 1 μM dexamethazone, 10 μM insulin, 20 μM indomethazine and 115 μg/mL 3-isobutyl-1-methylxanthine
5. Subsequently, cultured for 28 days with media change in every 3 days
6. Cells were then stained with Oil-Red 0:
   a. Wash three times with PBS
   b. Fix cells with 4% Paraformaldehyde for 60 min
   c. Wash once with $ddH_2O$
   d. Add Oil Red O Solution to the cells and incubate for 1 h with slow shaking
   e. Wash two times in 60% isopropanol
   f. Wash three to five times with $ddH_2O$
   g. Leave $ddH_2O$ on the plate or air dry the stained cells Example 9

Figure 26:
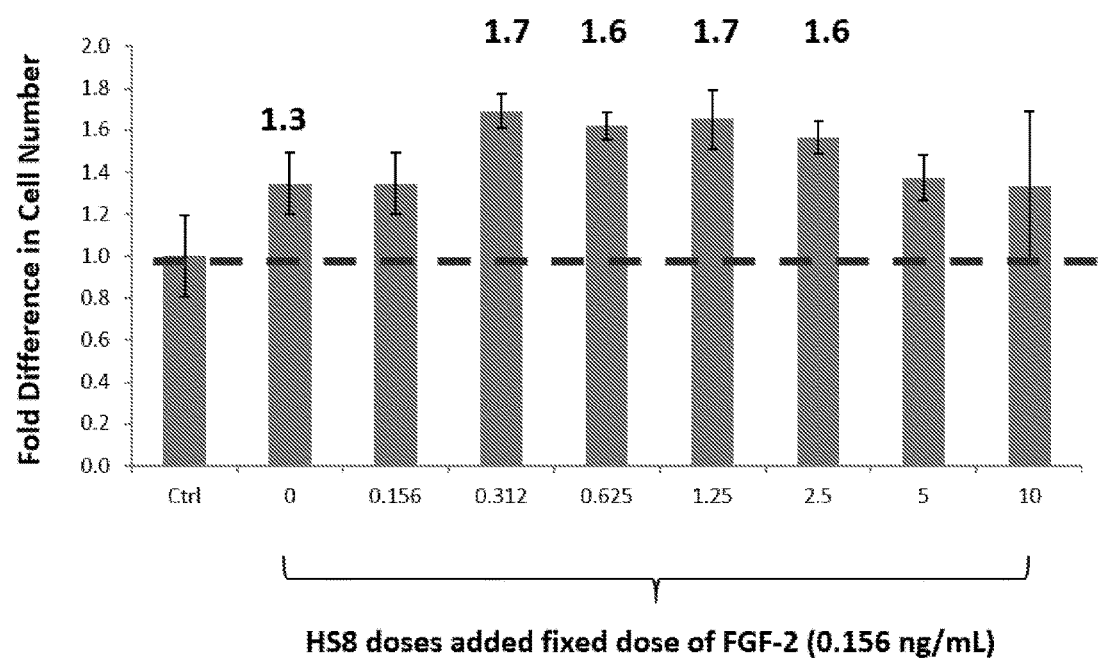
FIG. 26. HS8 enhances FGF-2 mediated MSC growth. Graph showing cell number of hMSCs following 4 days culture in normal maintenance (control) media, or with media containing varying doses of HS8 (μg/ml) and a fixed dose of FGF-2 (0.156 ng/ml).

The effect of HS8 on FGF-2 mediated growth hMSC was investigated using the methodology described below. HS8 was found to enhance FGF-2 mediated MSC growth (FIG. 26).

Cells

Passage 4 cells—hMSCs cultured in normal maintenance media with and without one of the following treatments:
FGF2 0.156 ng/mL only
FGF2 0.156 ng/mL with varying doses of HS8(+)

Cell Proliferation Protocol

Materials
1. hMSC—(purchased from Lonza).
2. FGF 2 (R & D systems. Cat No. 233-FB-025).
3. Maintenance media: DMEM (1000 mg/l glucose), 10% FCS, 1% Pen/Strep, 2 mM L-glutamine.
4. HS8 (HS8(+)), HS8(−), Porcine mucosal heparan sulfate (Celsus laboratories, USA), Heparin (Sigma Cat No. H3149).
5. Guava Flex reagent (Millipore).

Methods
1. Cells are plated on 24-well plates at 3000 cells/$cm^2$ in 500 μl/well media (Day 0).
2. Day 1—Media changed to contain maintenance media plus FGF2 (0.156 ng/mL) alone or FGF2 (0.156 ng/mL) with various concentrations of HS8(+): 10, 5, 2.5, 1.25, 0.625, 0.3125, 0.156 (μg/ml) in 500 μl of fresh media.
3. Media change every 2 days.
4. Cells are harvested at Day 4 with 100 μl of trypsin and neutralized with 300 μl of media.
5. Cells were counted in GUAVA machine (Guava flex reagent: cell suspension is 1:200).

Example 10

Figure 27:
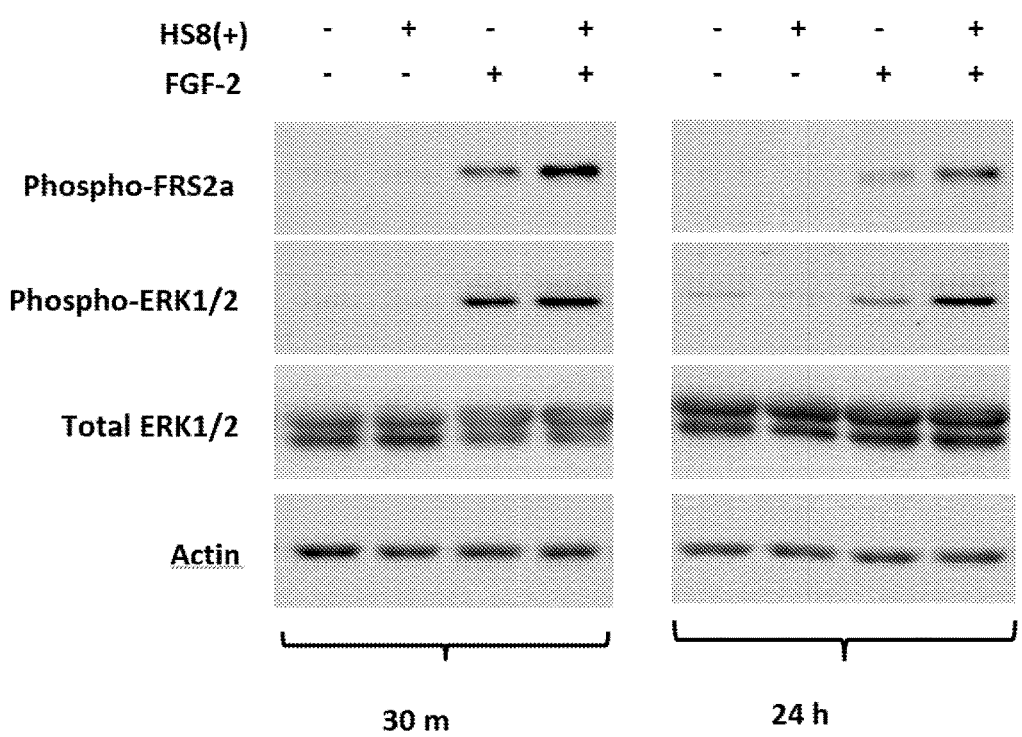
FIG. 27. HS8 sustains FGF-2 signaling. Western blots showing ERK1/2 phosphorylation and FRS2a phosphorylation at 30 mins and 24 hours post stimulation with HS8 and/or FGF-2.

The effect of HS8 on FGF-2 signaling via the ERK pathway was investigated using the methodology described below. HS8 was found to enhance/sustain FGF2 mediated signalling of the ERK pathway, as measured by phosphorylation of ERK1/2 and FRS2a (FIG. 27).

Cells

P4—hMSCs were cultured in normal maintenance media with and without the following treatments:
FGF2 0.312 ng/mL only
HS8 (HS8(+)) 2.5 μg/mL Western Blot Materials
1. hMSC—(purchased from Lonza)
2. FGF2 (R & D systems. Cat No. 233-FB-025)
3. Maintenance media: DMEM (1000 mg/L glucose), 10% FCS, 1% Pen/Strep, 2 mM L-glutamine
4. Serum-free media: DMEM (1000 mg/L glucose), 0.2% FCS, 1% Pen/Strep, 2 mM L-glutamine
5. Antibody against phospho-FRS2a (Cell Signaling. Cat No. 3861) 1:1000 in 5% BSA in TBST
6. Antibody against phospho-ERK1/2 (Cell Signaling. Cat No. 9106L) 1:2000 in 5% BSA in TBST
7. Antibody against total ERK1/2 (Cell Signaling. Cat No. 9102L) 1:1000 in 5% BSA in TBST
8. Antibody against actin (Millipore Chemicon. Cat No. MAB1501R) 1:8000 in 5% BSA in TBST Methods
1. Cells are plated at 10,000/cm$^2$ on 6-well plates in maintenance media
2. Day 1: Change media to serum-free media at 2 mL/well
3. Day 3: Add treatment to well. Required amount of HS8(+) and/or FGF2 is dosed in serum-free media and added at 10 μL/well
4. Cells are harvested in 100 μL/well with 1.5× laemmli buffer at different time points (30 min and 24 h)
5. Lysates were heated for 5 min at 95° C. and stored at −20° C.
6. Samples are freeze-thawed only once
7. 20 μL/well of sample is loaded into each lane of Novex 4-12% Bis-Tris SDS PAGE gel, 10 well (Invitrogen. Cat No. NP0335BOX)
8. Gel was run at 180V with 1×MOPS Buffer for 50 min
9. Resolved protein bands were then transferred to nitrocellulose membrane at 100V in 1× Transfer Buffer for 1 h 30 min
10. Nitrocellulose membrane was stained with Ponceau S solution and cut into strips according to the size of the protein of interest
11. Membranes were then blocked in either 5% BSA or 5% Non-fat Milk in TBST for 30 min to 1 h at room temperature with slow shaking
12. Primary antibodies of recommended dilutions were then incubated overnight at 4° C. with slow shaking
13. Blots were then washed three times with TBST for 5 min each
14. Secondary antibodies of recommended dilutions were then incubated for 1 h to 2 h at room temperature with slow shaking
15. Blots were washed three times with TBST for 5 min each
16. Incubate blots with Chemiluminescence reagents and proceed to dark room to develop x-ray films for band visualization.

Example 11—NMR Analysis of HS8

A sample of HS8 was stored at −20° C. prior to analysis. NMR analysis was completed by dissolution in D2O (600 uL) that contained the internal standard tBuOH (200 μL, δ1.24 ppm) that is used for chemical shift comparison and quantitation. Celsus HS was weighed accurately in ~1, 4 and 7 mg amounts, made up in the working D2O/tBuOH solution and analysed in the same run as HS8. Line fitting of the standard solutions gave regression of 0.995 or better for integration of the acetyl methyl region, the region δ 3.15-3.25 ppm and the lowest field portion of the anomeric region δ 5.15-5.65 ppm compared to the internal standard.

Due to the small sample size which results in low signal to noise only the acetyl region data was used to calculate the amount of HS8 delivering a value of 0.7 mg. A second experiment was completed comparing signal to noise of the acetyl peak and a value of 0.5 mg was recorded. This is an absolute value not related to the internal standard. After three freeze-dry steps to remove the tBuOH prior to further analysis the mass recorded was 1.2 mg. Of note is the SEC HPLC data can be integrated to give an approximate purity value and it also recorded 58% suggesting 0.7 mg of HS-GAG present in the material. As this weight discrepancy is not a new phenomenon in small GAG samples the assumption is made that varying humidity and a proportion of salt must be affecting the recorded mass.

Figure 31:
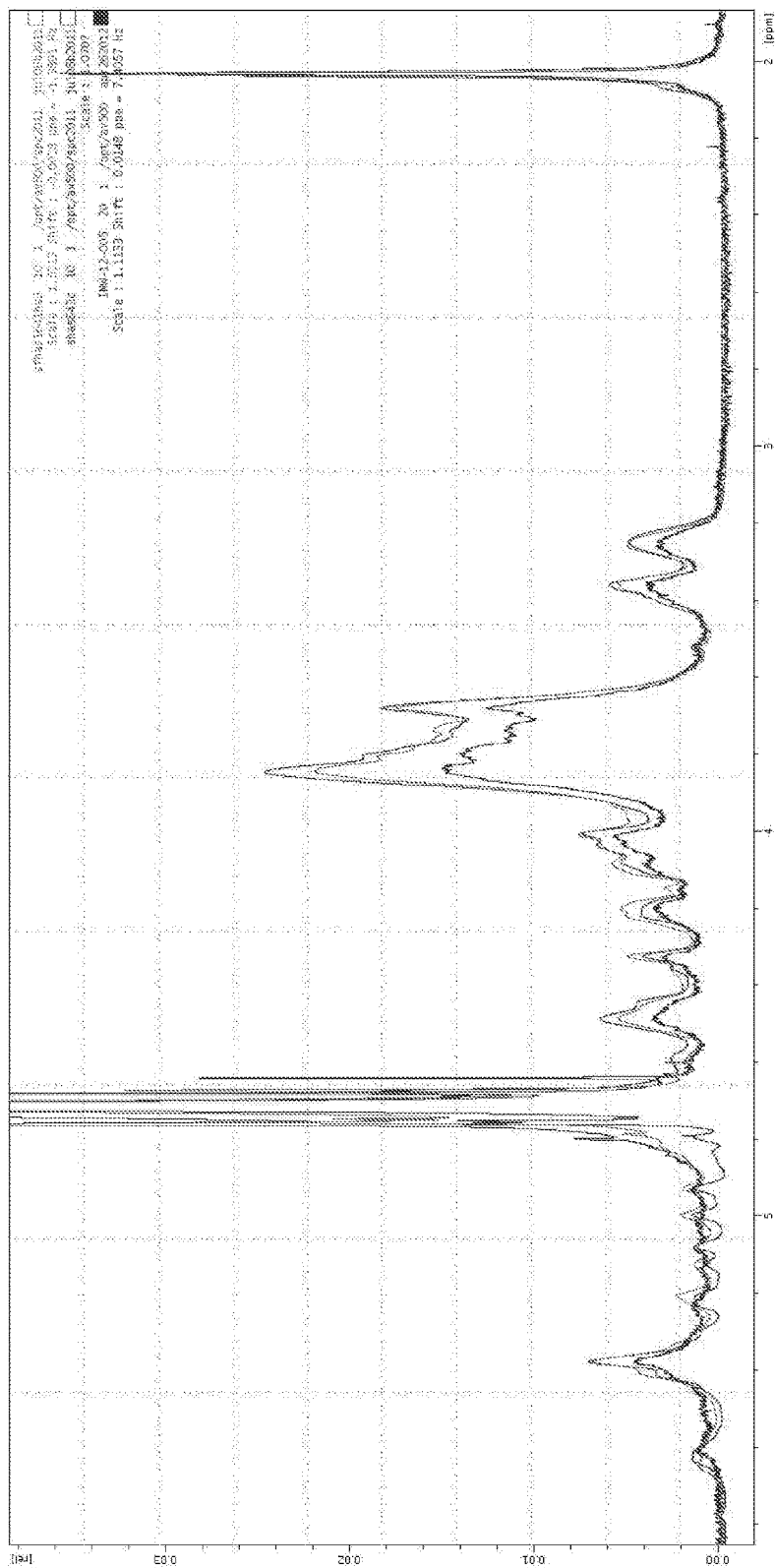
FIG. 31. $1^H$ NMR of Celsus HS, HS8 and HS3 ($D_2O$ solutions).

The 1H NMR spectrum of HS8, Celsus HS and HS3* is displayed in FIG. 31. The difference in intensity of the HS8 (lowest peak at 4.8-4.6 ppm) compared to other signals (Celsus HS is the highest peak at 4.8-4.9 and HS3 is the intermediate height peak) in the displayed plot is due to normalising all spectra to the height of the acetyl methyl resonance: in the case of this HS8 sample a slightly better shimming was observed with narrower line width causing the acetyl resonance to be slightly sharper and taller.

The chemical composition change of HS8 compared to Celsus HS is just differentiated by 2-D NMR.

Figure 32:
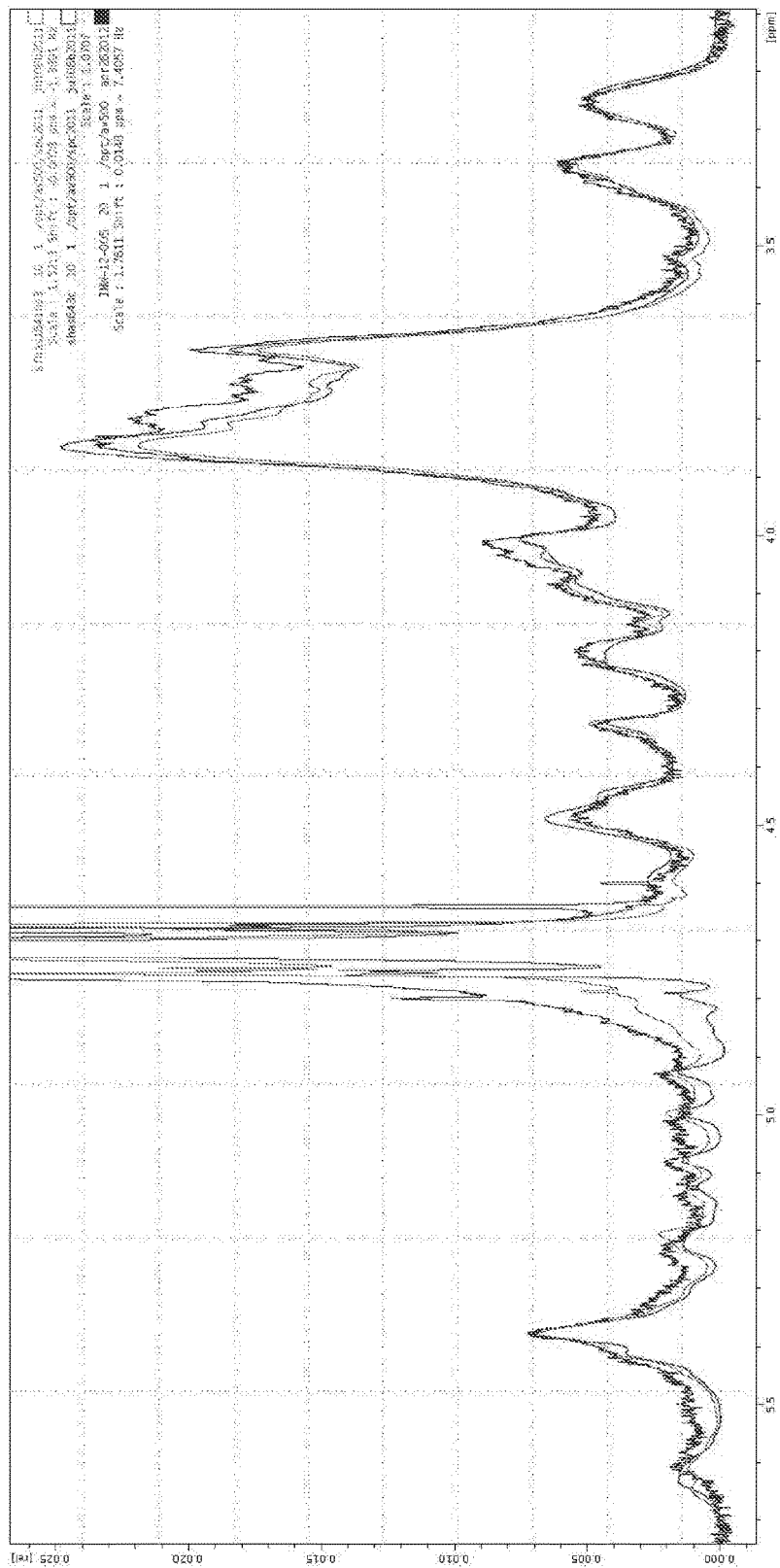
FIG. 32. Close-up of 1H NMR of Celsus HS, HS8 and HS3 ($D_2O$ solutions).

Closer examination of the methine and methylene regions of the HS8 1H NMR showed differences compared to Celsus HS and HS3 (FIG. 32).

[*HS3 is an isolated heparan sulphate having specific and high binding affinity for a heparan binding domain of BMP-2. HS3 is described in WO2010/030244]

Example 12—HPLC-SEC-RI of HS8 and Other HS Preparations

Heparan sulfate preparations (approximately 1 mg, weighed accurately) were made up to 2 mg/mL in water. Heparin lyase I, II and III digests of these preparations were 2 mg/mL in water. The solutions were centrifuged (14 000 g, 2 min) and 200 μL aliquots were taken for analysis.

The SEC-RI system consists of a Waters 2690 Alliance separations module and a Water 2410 refractive index monitor (range 64). The do/dc for quantitation from the RI chromatograms was set at 0.129 (ref). Samples were injected (50 μL) and eluted with 50 mM ammonium acetate with a flow rate of 0.5 mL/min from two Superdex™ Peptide 10/300 GL columns in series (300×10 mm GE Healthcare, Buckinghamshire, UK). Data was collected and analysed using ASTRA software (Version 4.73.04, Wyatt Technology Corp).

Figure 33:
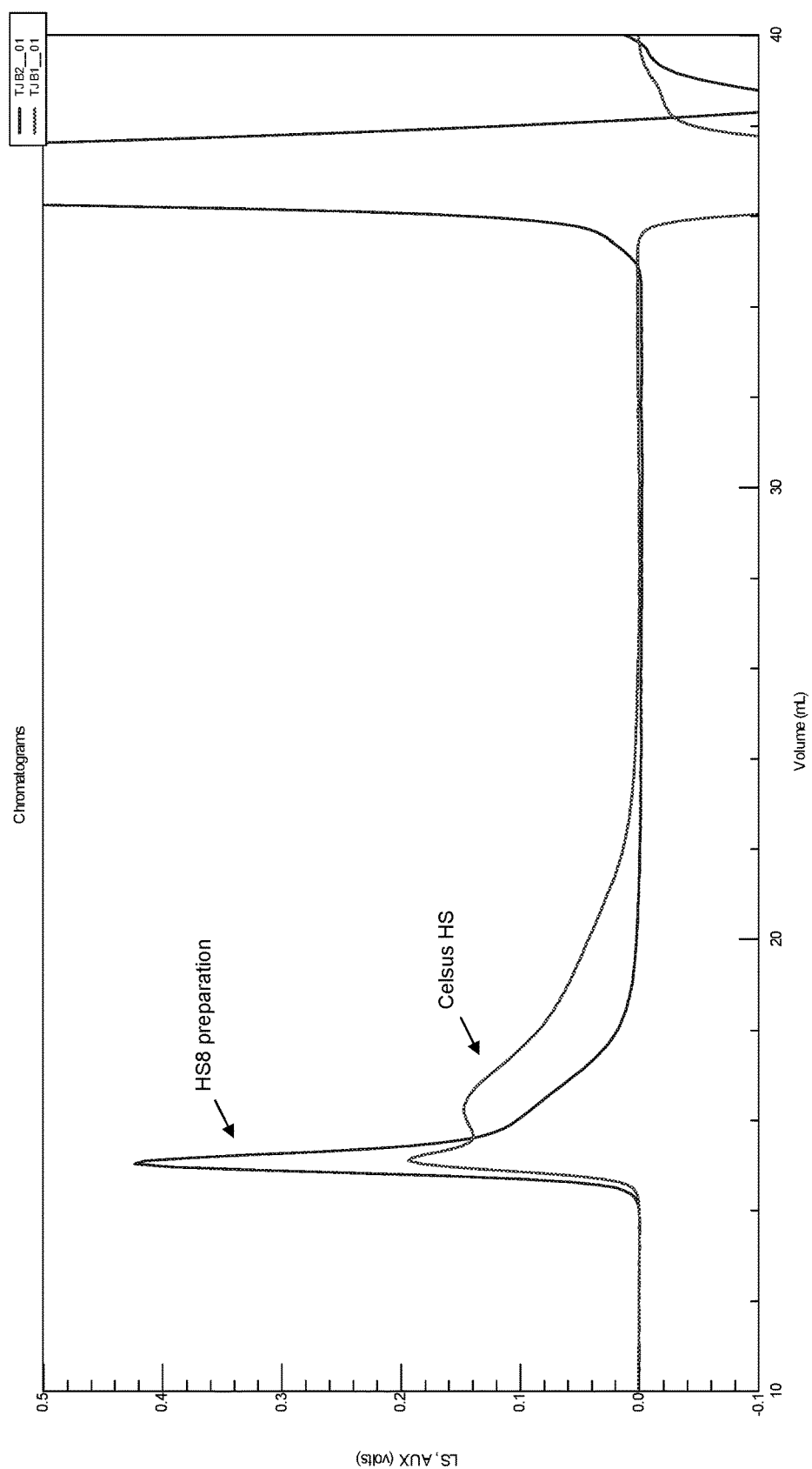
FIG. 33. HPLC-SEC-RI chromatograms of Celsus HS #10697 and HS8, separated on 2× Superdex Peptide columns eluted with 50 mM ammonium acetate.

The size-exclusion chromatography of the whole HS8 preparation displayed a distinct size-exclusion profile. The Celsus HS starting material shows a voiding signal at 15 mL with additional material of a range of sizes eluting to approximately 23 mL of eluent. As shown in FIG. 33 the HS8 material (retained by the FGF-2 affinity column) shows a size profile enriched in the material that voids the SEC columns.

Figure 34:
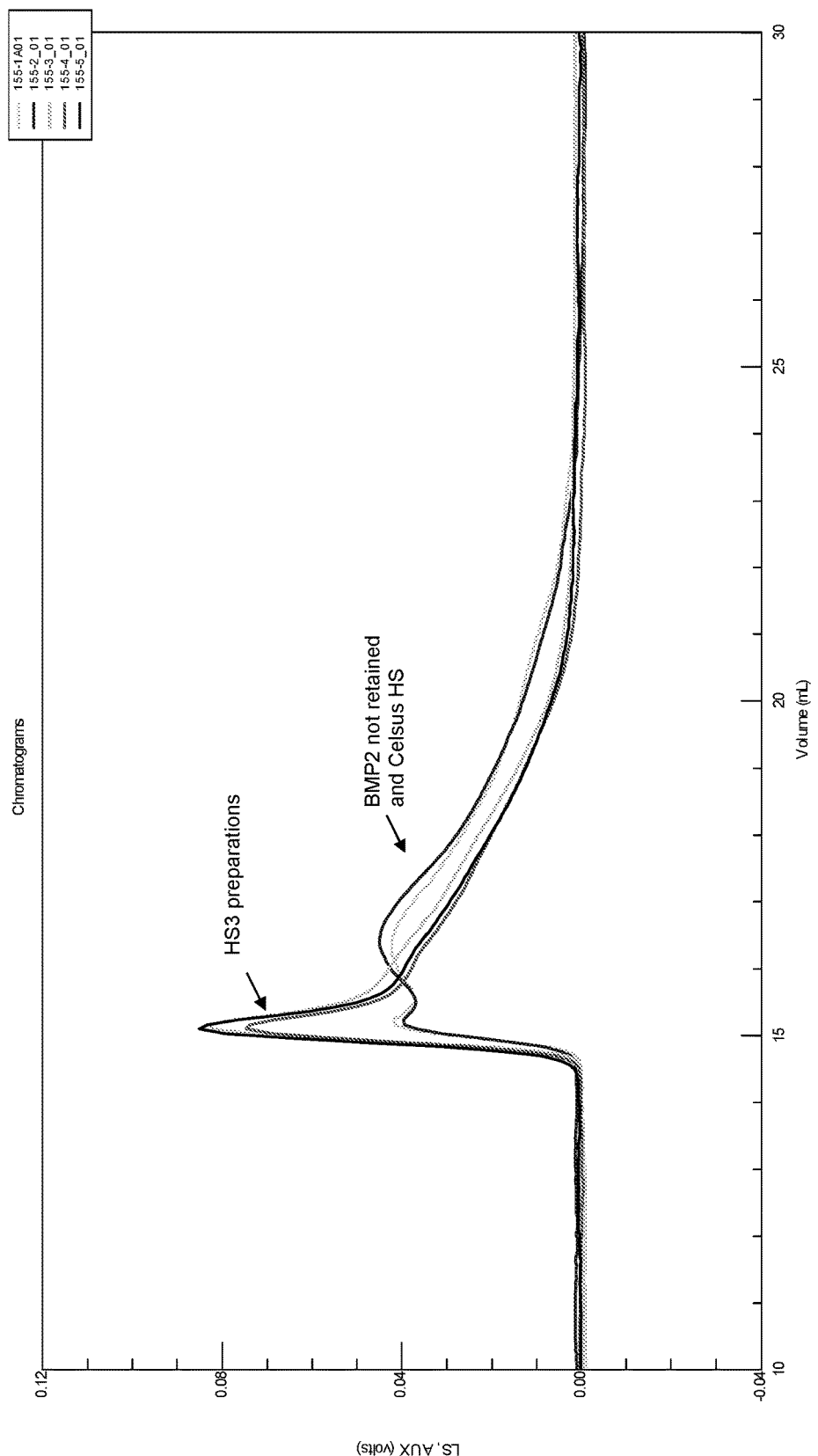
FIG. 34. HPLC-SEC-RI chromatograms of heparan sulfate: Celsus HS #10697; BMP2 not retained (848/HS3/001); BMP2 retained (HS3) (848/HS3/001); Initial run (HS3-001-01); Final run (HS3-001-02). The HS3 preparations show a high peak (0.06-0.08) at about 15 ml.

This is distinct again from the size profile of the HS3 preparations, showing an intermediate size profile between the HS8 and Celsus HS profiles (FIG. 34). The HS8 chromatogram shows a large salt signal at approximately 36 mL as this sample was prepared in 50 mM sodium acetate buffer (pH 7) rather than water.

Figure 35:
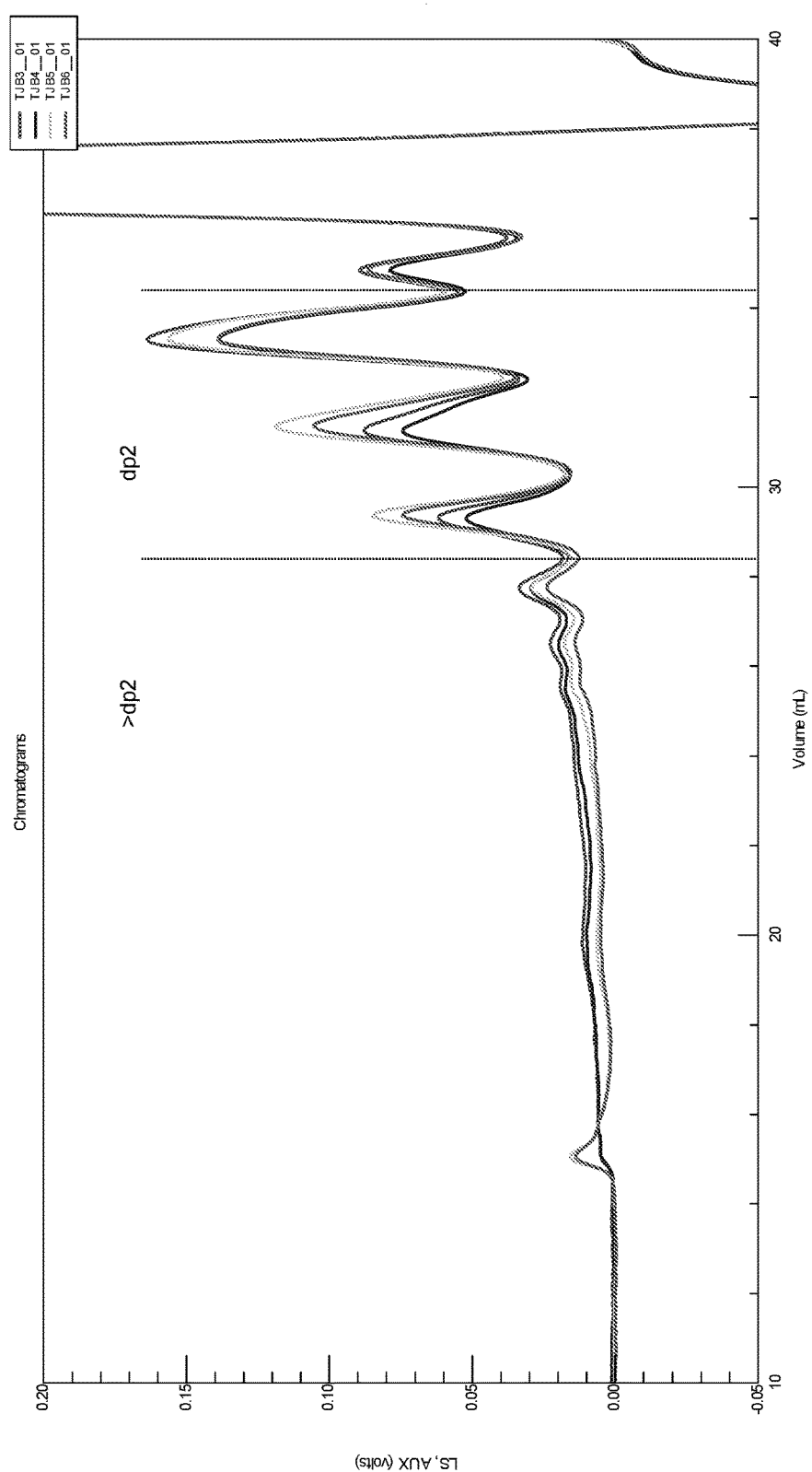
FIG. 35. HPLC-SEC-RI of heparin lyase I, II and III digests of HS preparations HS #10697 and HS #10595 from Celsus. Heparin lyase digests were done in duplicate. Vertical line indicates the cut off for the elution of disaccharides and oligosaccharides with a degree of polymerisation (dp) larger than 2.

FIG. 35 shows the SEC chromatograms for two different batches of the HS from Celsus. Batch #10697 was used as the starting material for the preparation of both HS3 and HS8. The digestion of both of these batches with the enzymes is similar except that batch #10595 appears to have a larger amount of material that is not digested at all and voids the columns.

Figure 36:
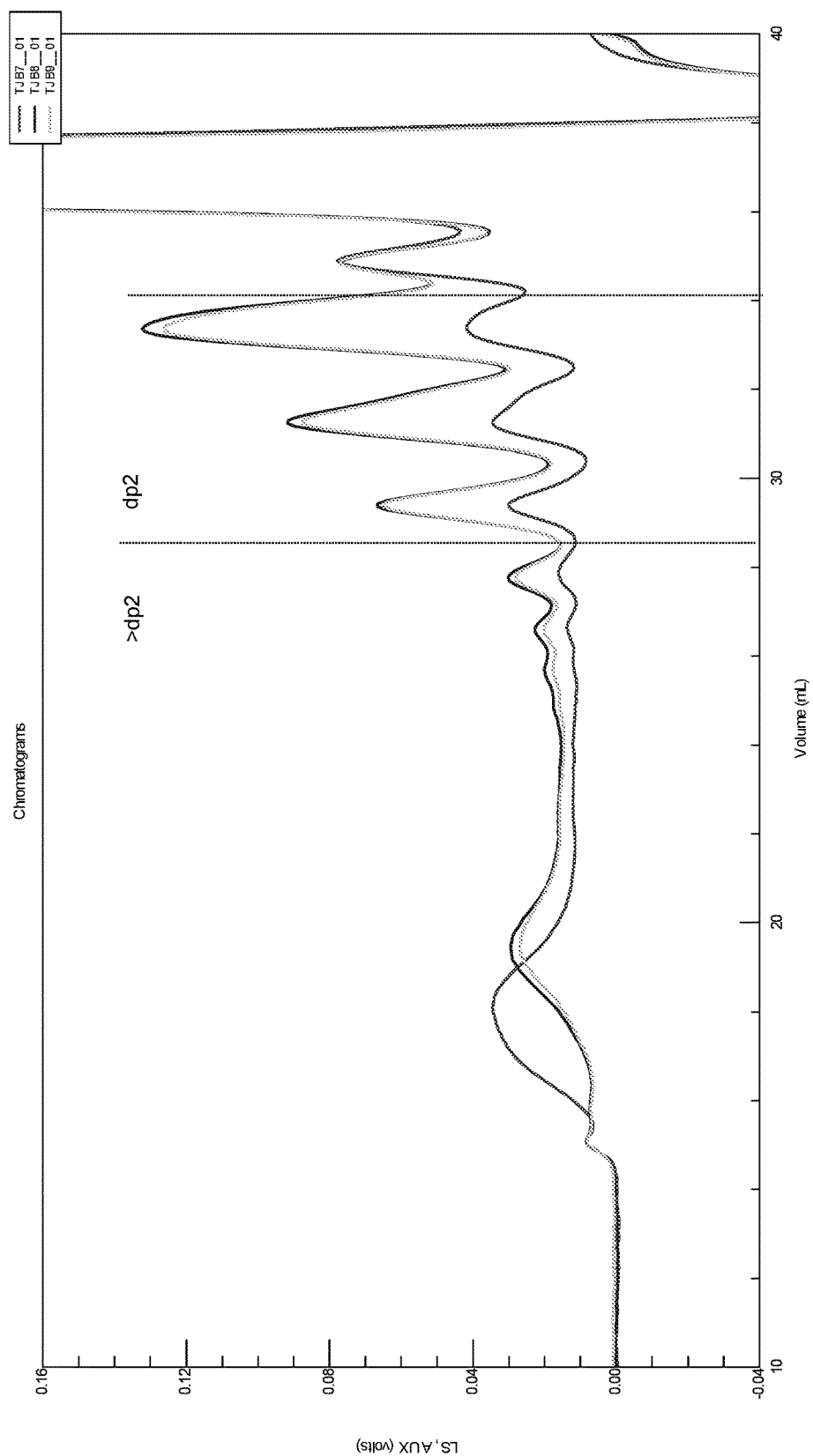
FIG. 36. HPLC-SEC-RI chromatograms of HS8 (broad peak at 18-20 ml), HS3-001-01 (peak at 19-20 ml), on 2× Superdex Peptide columns, eluted with 50 mM ammonium acetate.

The size profile of the heparin lyase digest of HS8 (FIG. 36) is quite different from that of the Celsus HS starting material (FIG. 35) or HS3 (FIG. 36). The size profile obtained for HS3 was very similar to that obtained in previous digests. The HS8 chromatogram, like that for the HS3 digests, shows little signal strength at the void volume (15 mL), suggesting that most of the material is digested to some extent. However, the two HS3 digests show significant and distinct signal strength at approximately 19 mL, whereas the HS8 shows a broad signal around 18 mL.

Example 13—[3H] Heparin Assay

Figure 37:
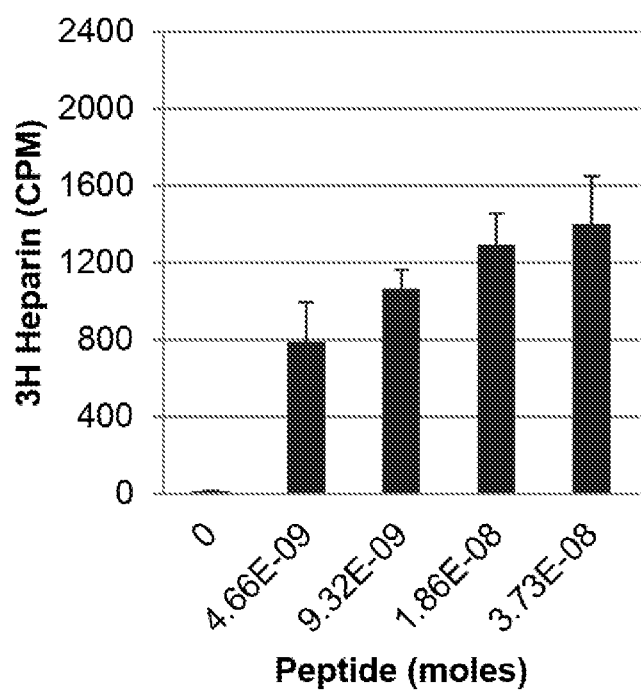
FIG. 37. Graphs showing heparin binding SEQ ID NO:1.

The heparin binding ability of SEQ ID NO:1 derived from the amino acid sequence of FGF2 was assessed using the protocol described below. Results are shown in FIG. 37.

Materials
(1) Peptides:
Gandhi et al (HS8)—Manufactured by Nanyang Technological University GHFKDPKRLYCKNGGF-Ahx-(K)Biotin
(2) 3H Heparin 0.1 µCi (Perkin Elmer, Boston, USA)
(3) Nitrocellulose Membrane (Bio-Rad, USA)
(4) Bovine Serum Albumin 4% (w/v) in PBS
(5) Vacuum Oven (Thermo Fisher Scientific, USA)
(6) Tri-Carb 2800 TCR Liquid Scintillation Analyzer (Perkin Elmer, Boston, USA)

Methods
(1) Make up FGF2-HBD-peptides to desired concentrations (4.66×10-9, 9.32×10-9, 1.86×10-8, 3.73×10−8 moles) with PBS
(2) Soak identical nitrocellulose membranes in duplicates with known concentrations of peptides
(3) Air dry the membranes for 1 h
(4) Further drying in vacuum oven at 800 C for 45 mins
(5) Wash membranes 3 times with PBS
(6) Add 3H Heparin 0.1 µCi to the membranes and incubate for 16 h in scintillation counting vials
(7) Wash membranes 4 times with PBS
(8) Determine radioactivity with Tri-Carb 2800 TCR Liquid Scintillation Analyzer (Perkin Elmer, Boston, USA)

Example 14

Figure 38:
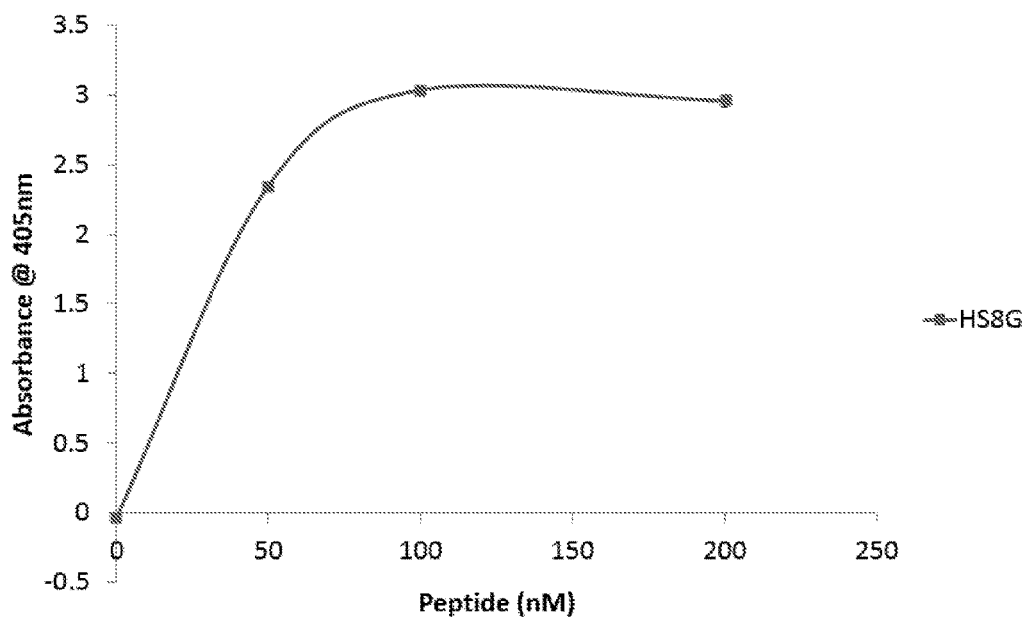
FIG. 38. Graph showing ability of HS8 to bind immobilised heparin.

The ability of heparin binding domain peptide SEQ ID NO:1 to bind immobilized heparin was assessed using the protocol described below. Results are shown in FIG. 38.

Materials
1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Peptides:
Gandhi et al (HS8)—Manufactured by Nanyang Technological University GHFKDPKRLYCKNGGF-Ahx-(K)Biotin
5. ExtraAvidin-AP (Sigma Cat No. E2636)
6. Sigma FAST p-Nitrophenyl phosphate (Sigma, N2770)

Method
1. Dissolve Heparin in SAB (5 µg/ml)
2. Add 200 µl of Heparin solution/well into GAG binding plate and incubate overnight at RT protected from light
3. Wash plate carefully 3× with 250 µl/well with SAB
4. Incubate plate with 250 µl/well blocking buffer for 1 hour at 370 C protected from light
5. Wash plate carefully 3× with 250 µl/well with SAB
6. Dissolve peptides in blocking buffer and perform serial dilution: 0, 50, 100, 200 nM
7. Dispense 200 µl/well of diluted protein to GAG coated plate and incubate for 2 hours at 370 C
8. Wash plate carefully 3× with 250 µl/well with SAB
9. Add 200 µl/well of 220 ng/ml of ExtraAvidin-AP in blocking solution and incubate for 30 min at 370 C
10. Wash plate carefully 3× with 250 µl/well with SAB
11. Add 200 µl/well of Development reagent: Sigma FAST p-Nitrophenyl phosphate in DI water and incubate for 40 min at RT
12. Read absorbance at 405 nm Example 15

Figure 39:
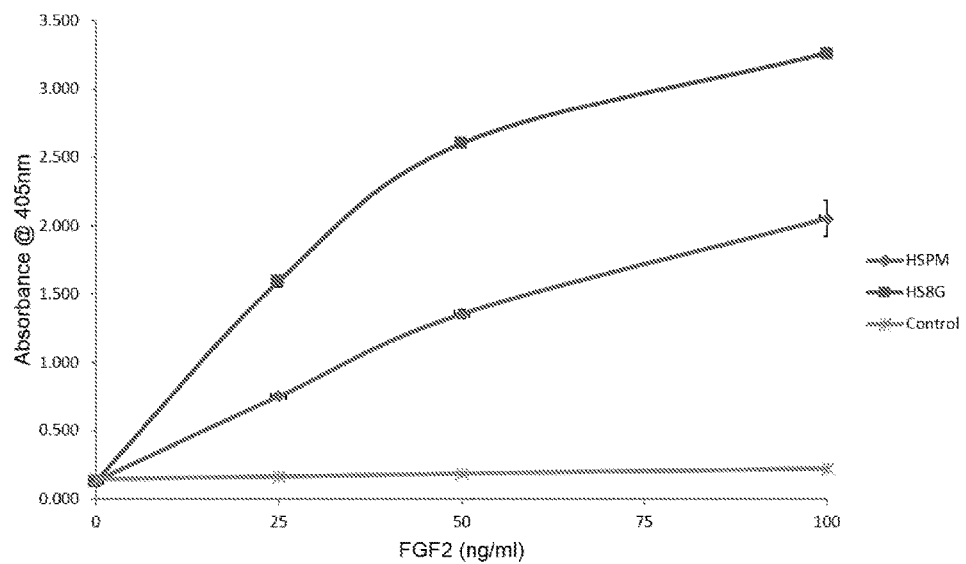
FIG. 39. Graph showing ability of FGF-2 to bind HS8 purified by affinity chromatography (column derivatized with SEQ ID NO:1). This was compared to binding with the raw starting HS (HS-PM porcine mucosa), or a no sugar control.

FGF-2 was assessed for its ability to bind HS8. This was compared to binding with the raw starting HS (HS-PM porcine mucosa), or no sugar. Results are shown in FIG. 39.

Materials
1. Standard Assay Buffer (SAB)—100 mM NaCl, 50 mM sodium acetate, 0.2% v/v tween 20, pH 7.2
2. Blocking buffer—0.4% Fish gelatin (Sigma Cat No. 67041)+SAB
3. GAG binding Plate (Iduron, UK)
4. Proteins from R& D Systems: FGF 2—233 FB
5. Antibodies from R & D Systems: FGF 2—BAM233
6. ExtraAvidin-AP (Sigma Cat No. E2636)
7. Sigma FAST p-Nitrophenyl phosphate (Sigma, N2770)

Method
1. Dissolve GAG in SAB (5 µg/ml)
2. Add 200 µl of GAG solution/well into GAG binding plate and incubate overnight at RT protected from light
3. Wash plate carefully 3× with 250 µl/well with SAB
4. Incubate plate with 250 µl/well blocking buffer for 1 hour at 370 C protected from light
5. Wash plate carefully 3× with 250 µl/well with SAB
6. Dissolve proteins with blocking buffer and perform serial dilution: 0, 0.781, 1.56, 3.125 nM
7. Dispense 200 µl/well of diluted protein to GAG coated plate and incubate for 2 hours at 370 C
8. Wash plate carefully 3× with 250 µl/well with SAB
9. Add 200 µl/well of 250 ng/ml of biotinylated primary antibody in blocking solution and incubate for 1 hour at 370 C
10. Wash plate carefully 3× with 250 µl/well with SAB
11. Add 200 µl/well of 220 ng/ml of ExtraAvidin-AP in blocking solution and incubate for 30 min at 370 C
12. Wash plate carefully 3× with 250 µl/well with SAB 13. Add 200 µl/well of Development reagent: Sigma FAST p-Nitrophenyl phosphate in DI water and incubate for 40 min at RT 14. Read absorbance at 405 nm Example 16

Figure 40:
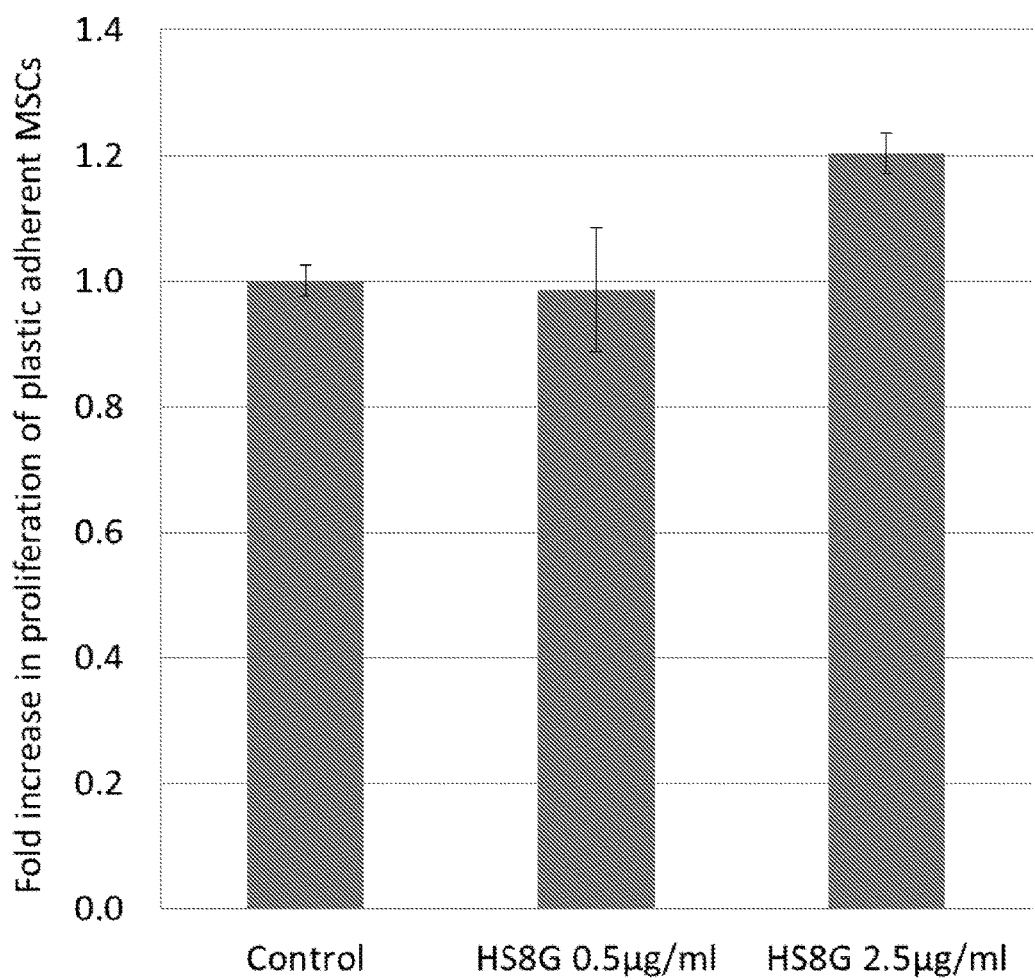
FIG. 40. Graph showing proliferation of plastic adherent mesenchymal stem cells over 6 days in the presence of HS8.

Proliferation of plastic adherent mesenchymal stem cells over 6 days in the presence of HS8 was analysed. Results are shown in FIG. 40.

Cell Proliferation Protocol

Materials

1. HM20 hMSC—Male Hispanic 20 year old donor (purchased from Lonza)
2. FGF 2 (R & D systems. Cat No. 233-FB-025)
3. Maintenance media: DMEM (1000 mg/l glucose), 10% FCS, 1% Pen/Strp, 2 mM L-glutamine
4. HS8
5. Guava Flex reagent (Millipore)

Methods

1. HM20 cells are plated on 24-well plates at 3000 cells/cm2 in 500 µl/well media (Day 0)
2. Day 1—Media changed GAGs (µg/ml)—2.5 and 0.5
3. Media change every 2 days
4. Cells are harvested at designated time points (Day 6)—with 100 µl of trypsin and neutralized with 300 µl of media
5. Cells were counted in Guava machine (Guava flex reagent: cell suspension is 1:200)

Example 17

Figure 41:
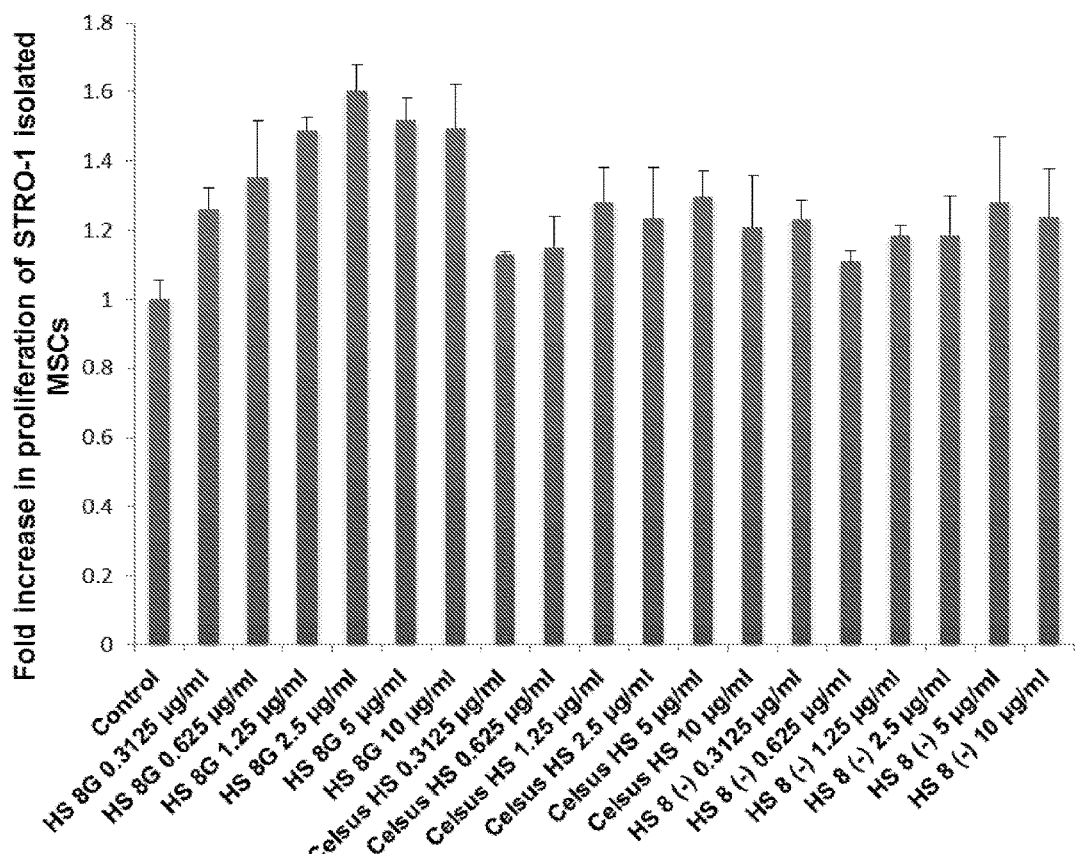
FIG. 41. Graph showing proliferation as measured by BrDU of STRO-1-isolated mesenchymal stem cells over 36 hours in the presence of isolated HS8, as compared to the raw Celsus starting HS (HS-PM), or the non-binding HS flow-through (HS8−).

Proliferation of STRO-1-isolated mesenchymal stem cells over 36 hours in the presence of isolated HS8, as compared to the raw Celsus starting HS (HS-PM), or the non-binding HS flow-through (HS8−) was measured by BrDU incorporation as described below. Results are shown in FIG. 41 (in which HS8G=HS8).

Protocol (Cell Proliferation ELISA, BrdU (Colorimetric), Roche)

1. Cell Seeding—5000 cells in 190 µl of media/well (96 well plate)
2. Media—Alpha MEM+10% Fetal calf Serum (FCS)+1% L-gluatamine+1% Penicillin and Streptomycin+100 nM L-glutamate
3. Incubate for 6 hours in 370 C and 5% CO2
4. Add different doses of treatments in 10 µl of media for designated wells as in the layout after 6 hours of incubation
5. GAGs (µg/ml)—10, 5, 2.5, 1.25, 0.625, 0.3125
6. Incubate for 36 hours with treatments in 37° C. and 5% CO2
7. Add BrdU into each well.
8. Label the cells with BrdU for 2 hours in 37° C. and 5% CO2 (Add 20 µl of BrdU labeling solution/well)
9. Remove labeling medium by tapping off the plate
10. Add 200 µl/well FixDenat to the cells and incubate for 30 min at 15-25° C.
11. Remove FixDenat solution thoroughly by flicking and tapping
12. Add 100 µl/well anti-BrdU-POD working solution and incubate for 90 min at 15-25° C.
13. Remove antibody conjugate by flicking off and rinse wells three times with 250 µl/well washing solution (1×PBS)
14. Remove washing solution by tapping.
15. Add 100 µl/well substrate solution and incubate for 30 min at 15-250 C 16. Measure the absorbance at 370 nm (reference wave length: 492 nm)

Example 18—Capillary Electrophoresis (CE) Analysis of Disaccharides

Heparan sulfate (HS) was from Celsus Laboratories Inc. (HO-03103, Lot #HO-10697). Disaccharide standards (ΔUA,2S-GlcNS,6S; ΔUA,2S-GlcNS, ΔUA,2S-GlcNAc,6S, ΔUA-GlcNS,6S, ΔUA-GlcNS, UA-GlcNAc, ΔUA,2S-GlcNAc, ΔUA-GlcNAc,6S, ΔUA,2S-GlcN, ΔUA,2S-GlcN,6S, ΔUA-GlcN,6S, ΔUA-GlcN Cat No. HD001 to HD013, Iduron Ltd, Manchester, UK), derived from the digestion of high-grade porcine heparin by bacterial heparinases, were purchased from Iduron Ltd, Manchester, UK. A synthetic derivative of a not naturally occurring disulfated disaccharide (ΔUA,2S-GlcNCOEt,6S), was also purchased from Iduron for use as an internal standard. Heparin Oligosaccharides (dp4, dp6, dp8, dp10, dp12 (Cat. No. HO04, HO06, HO08, HO10, HO12)) and selectively desulfated heparin standards (2-O, 6-O and N-desulfated heparin) (Cat No. DSH001/2, DSH002/6, DSH003/N, Iduron Ltd, Manchester, UK) were also purchased from Iduron Ltd, Manchester, UK.

Heparin lyase I (Heparitinase, EC 4.2.2.8, also known as heparitinase I), heparin lyase II (heparitinase II, no EC number assigned) and heparin lyase III (heparinase, EC 4.2.2.7, also known as heparitinase III) were obtained from Seikagaku Corporation, Japan. The enzymes, supplied as lyophilised powders (0.1 U/vial), were dissolved in 0.1% BSA to give solutions containing 0.5 mU/µL. Aliquots (5 µL; 2.5 mU) were frozen (−80° C.) until needed.

Digestion of HS Preparations with Heparin Lyase Enzymes

HS preparations (1 mg) were each dissolved in 500 µL of sodium acetate buffer (100 mM containing 10 mM calcium acetate, pH 7.0) and 2.5 mU each of the three enzymes was added. The samples were incubated at 37° C. overnight (24 h) with gentle inversion (9 rpm) of the tubes. A further 2.5 mU each of the three enzymes was added to the samples which were incubated at 37° C. for a further 48 h with gentle inversion (9 rpm) of the tubes. Digests were halted by heating (100° C., 5 min) and then lyophilized. The digests were resuspended in 500 µL water and an aliquot (50 µL) was taken for analysis by CE.

Capillary Electrophoresis (CE)

The capillary electrophoresis operating buffer was made by adding an aqueous solution of 20 mM $H_3PO_4$ to a solution of 20 mM $Na_2HPO_4.12H_2O$ to give pH 3.5. The column wash was 100 mM NaOH (diluted from 50% w/w NaOH). The operating buffer and column wash were both filtered using a Millipore filter unit fitted with 0.2 µm cellulose acetate membrane filters (47 mm ø; Schleicher and Schuell, Dassel, Germany). Stock solutions of the 12 disaccharide standards were prepared by dissolving the disaccharides in water (1 mg/mL). To determine the calibration curves for the standards, a mix containing all twelve standards was prepared. The stock solution of the 12 standard mix contained 10 µg/100 µL of each disaccharide and a dilution series containing 10, 5, 2.5, 1.25, 0.625, 0.3125 µg/100 µL was prepared; including 2.5 µg of internal standard (ΔUA,2S-GlcNCOEt,6S). The digests of HS were diluted (50 µL/mL) with water and the same internal standard was added (2.5 µg) to each sample. The solutions were freeze-dried and re-suspended in water (1 mL). The samples were filtered using PTFE hydrophilic disposable syringe filter units (0.2 µm; 13 mm ø; Advantec, Toyo Roshi Kaisha, Ltd., Japan).

The analyses were performed using an Agilent$^{3D}$CE (Agilent Technologies, Waldbronn, Germany) instrument on an uncoated fused silica capillary tube (75 μm ID, 64.5 cm total and 56 cm effective length, Polymicro Technologies, Phoenix, Ariz., Part Number TSP075375) at 25° C. using 20 mM operating buffer with a capillary voltage of 30 kV. The samples were introduced to the capillary tube using hydrodynamic injection (50 mbar×12 sec) at the cathodic (reverse polarity) end.

Before each run, the capillary was flushed with 100 mM NaOH (2 min), with water (2 min) and pre-conditioned with operating buffer (5 min). A buffer replenishment system replaced the buffer in the inlet and outlet tubes to ensure consistent volumes, pH and ionic strength were maintained. Water only blanks were run at both the beginning, middle and end of the sample sequence. Absorbance was monitored at 232 nm. All data was stored in a ChemStore database and was subsequently retrieved and re-processed using ChemStation software.

Eleven of the 12 heparin disaccharides in the standard mix were separated using conditions detailed above. The 12th disaccharide, ΔUA-GlcN, does not migrate under the conditions used for these experiments. However, this disaccharide has not been reported to occur in heparan sulfates. The R2 values for the standard calibration curves ranged from 0.9949 to 1.0.

The heparin lyase I, II and III digest of the HS preparations was done in duplicate and each duplicate was injected twice in the CE. Therefore, the normalized percentage of the disaccharides in the HS digest is the mean average of the results for the analyses. Of the 11 disaccharides separated in the standard mixes, only eight of these are detected in the HS digests. Other small signals are seen on the baseline of the electrophoretograms of the digests and these may correspond to oligosaccharides>2 dp. As mentioned above, the larger oligosaccharides will have less UV absorbance compared with the disaccharides.

Figure 42:
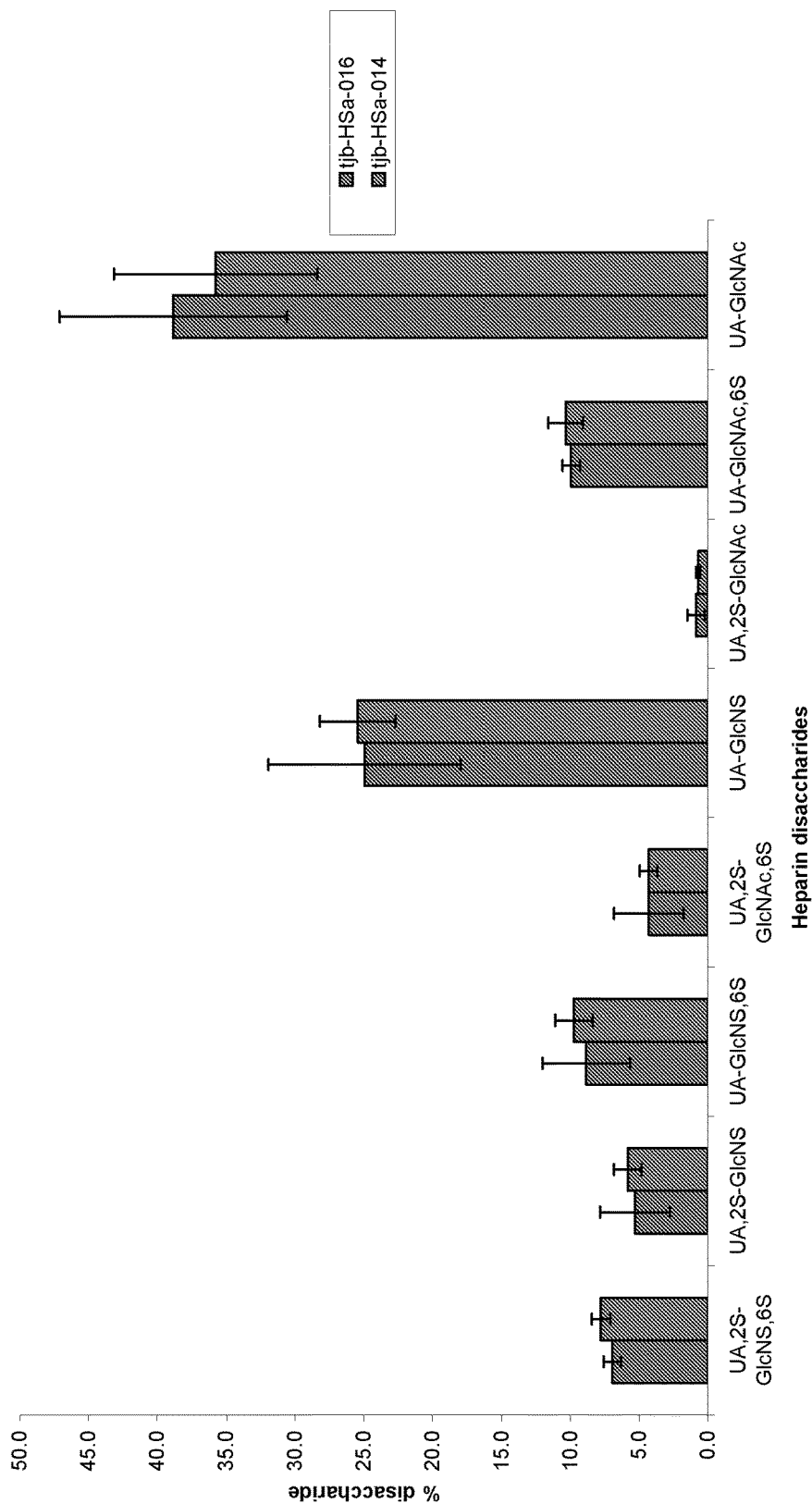
FIG. 42. Graph showing normalized disaccharide composition for Celsus HS. Comparison of digestion of Celsus HS Lot #10697 to a previous analysis on the same sample.
Figure 43:
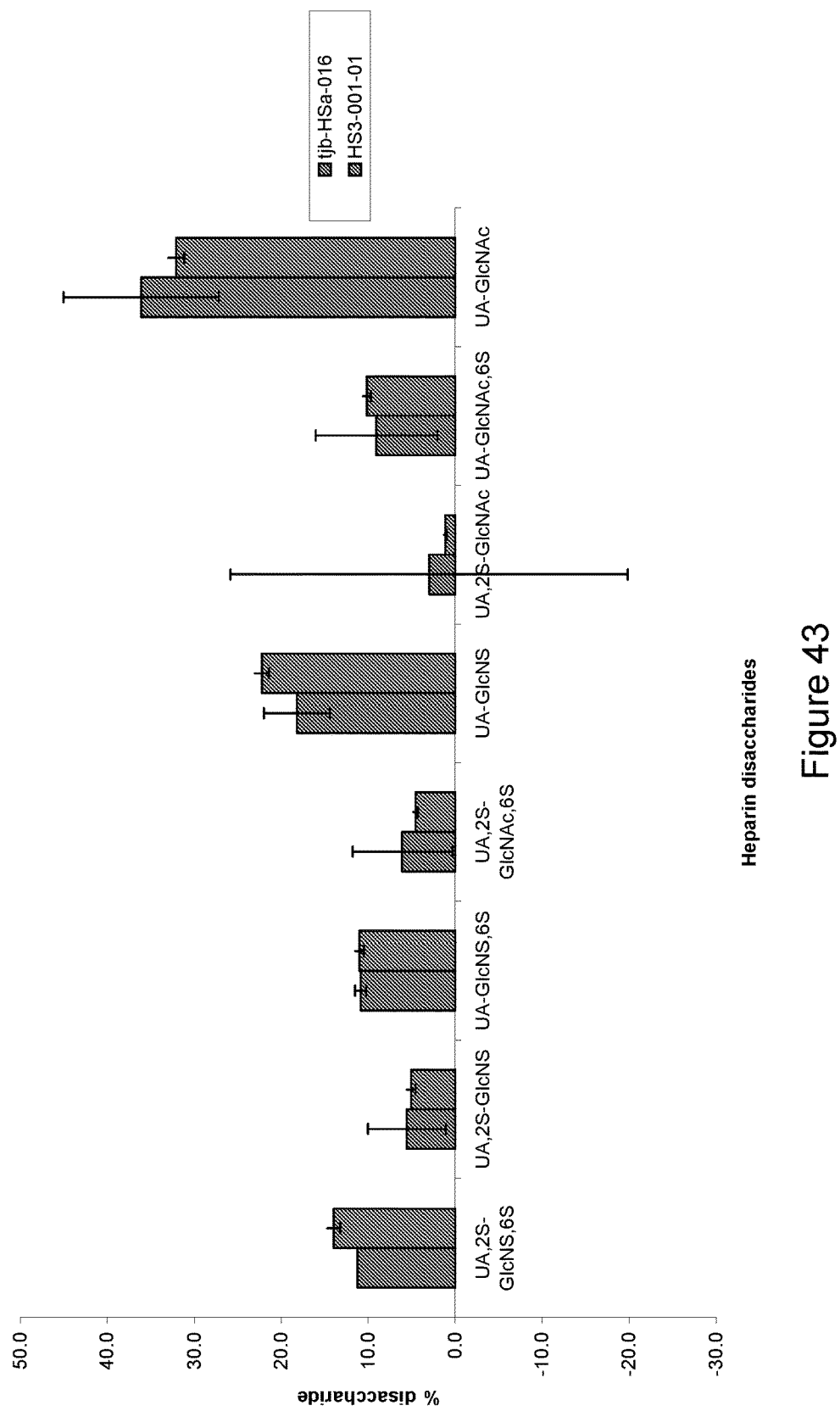
FIG. 43. Graph showing normalized disaccharide composition for HS3. Comparison of digestion of HS3-001-01.

Duplicate analyses were completed on a sample of Celsus HS (Lot #10697) and compared to a previous set of analyses on the same sample: these results are displayed in FIG. 42. Excellent correlation between the two sets of analyses was observed.

Figure 44:
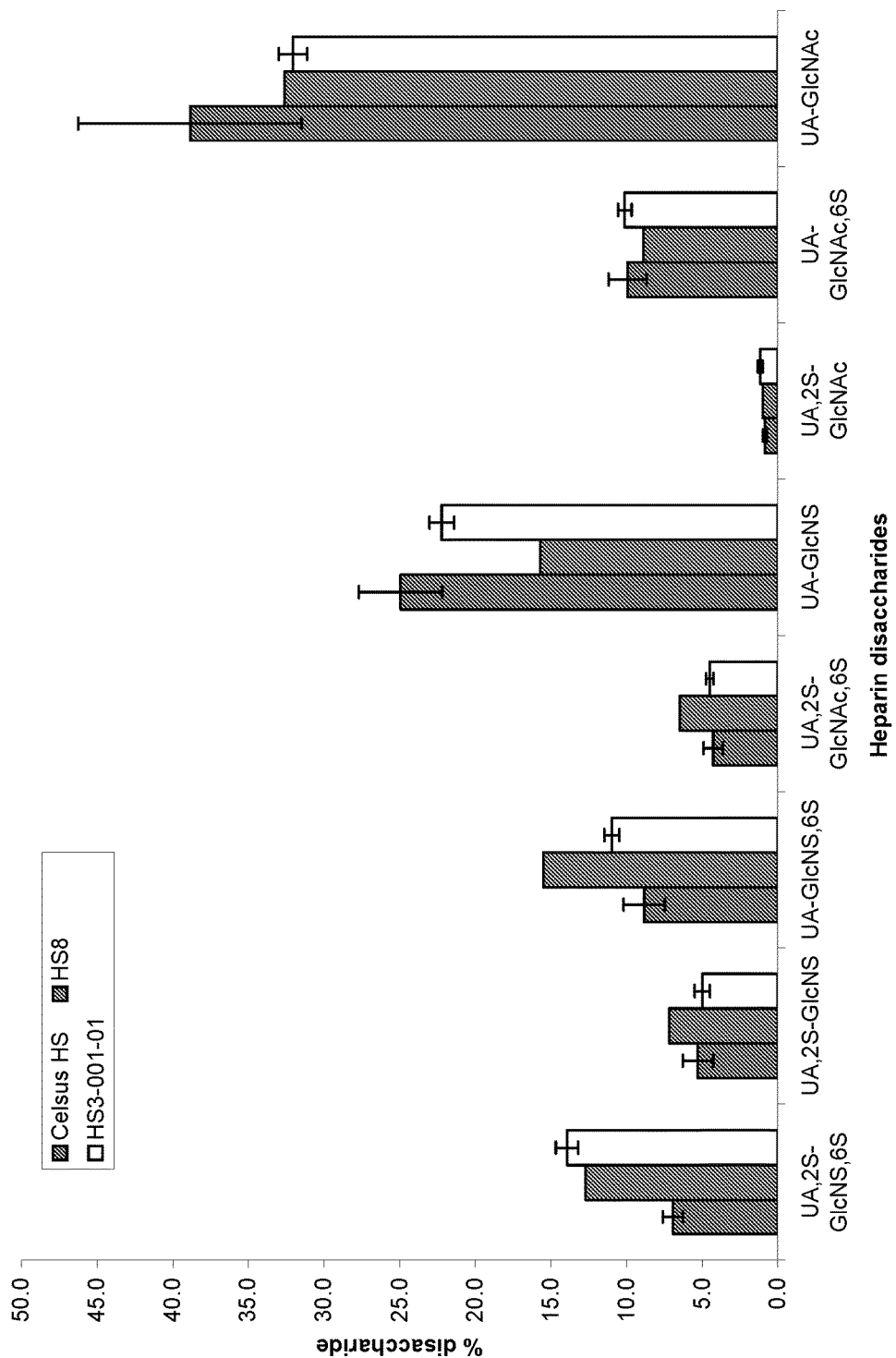
FIG. 44. Graph showing disaccharide composition of Celsus HS, HS8 and HS3.

The proportion of the eight disaccharides in the Celsus HS digests were similar to other previous analyses with a large component of ΔUA-GlcNAc and ΔUA-GlcNS and lesser proportions of ΔUA-GlcNAc,6S, ΔUA-GlcNS,6S and ΔUA,2S-GlcNS,6S (FIG. 42). This corresponds to the large proportion of mono- and unsulfated disaccharide lesser proportions of disulfated disaccharide and small proportion of trisulfated disaccharide consistent with HPLC-SEC profiles. The non-retained HS is enriched in the mono- and unsulfated disaccharides compared with the Celsus HS starting material. This pattern for the non-retained material was also seen quite distinctly in HPLC-SEC chromatograms. In the case of the analyses of HS8 the sample size permitted only a single analysis and so no error data is provided for this preparation. Comparison of HS8, HS3 and Celsus HS is displayed in FIG. 44.

The disaccharide composition for HS8 is comparable to that of HS3 (an HS isolated from Celsus HS through affinity for a heparin binding domain from BMP2, as described in WO2010/030244) in that a more sulfated (charged) fraction has in general been prepared from the Celsus HS. However; there is a striking difference in that there is a greater proportion of UA-GlcNS,6 s and a lesser proportion of US-GlcNS for HS8 in comparison to HS3.

Raw Celsus HS from which HS8 was derived has an average molecular weight of 20-25 kDa (compared with ~15 kDa for heparin), and the process of identifying HS8 by affinity chromatography did not result in a substantial change in the observed molecular weight of HS chains. Each disaccharide unit is expected to have a molecular weight in the range ~430 to ~650 KDa. Using a rough average of 500 daltons per disaccharide (the average disaccharide in heparin is ~650 daltons, for example), indicates (as a basic approximation) a chain length for HS8 of about 44 rings per average (22 kDa) HS8.

Example 19

Having identified that HS8 preferentially binds to FGF2 and increases the growth rate of hMSCs, we further explored the mechanism of HS8 activity.

Either FGF2 neutralizing antibody or FGFR1 inhibitors (both kinase inhibitor and neutralizing antibody) is able to reduce the proliferative effect of HS8 in hMSCs (FIGS. 47-50), confirming that the mitogenic effect of HS8 in hMSCs is via its interaction with FGF2/FGFR but not other molecules. In the presence of HS8, the rapid degradation of FGF2 is delayed (FIG. 46), proving that HS8 interacts with FGF2 to protect it from being degraded in culture medium.

Figure 51:
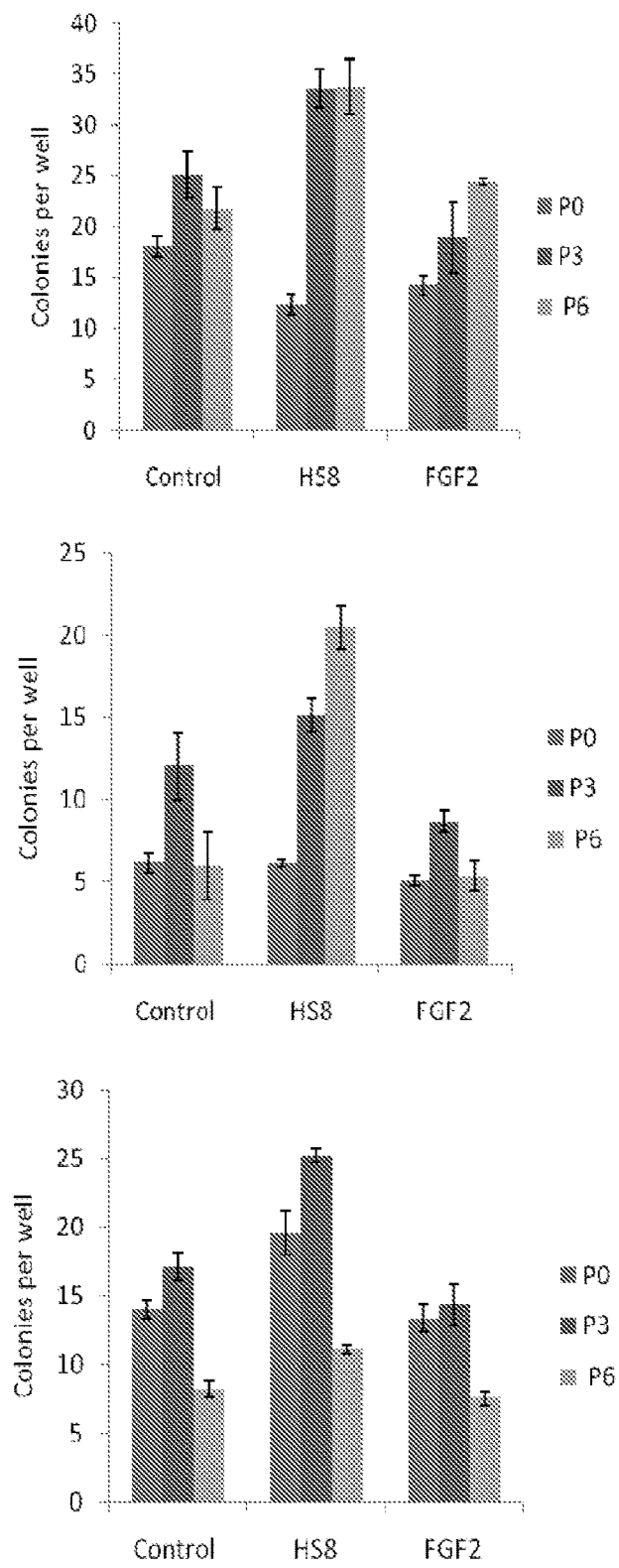
FIG. 51. Graphs showing human MSCs expanded in HS8 supplemented medium are more clonegenic (3 separate donors).

We have shown (above) that HS8 enhances hMSC self-renewal while maintaining multipotency. To test if HS8 supplementation in hMSC routine culture can expand the culture faster, we grew hMSCs from three individual donors separately in HS8 supplemented medium. We noted that hMSCs exposed to HS8 were able to form more colonies (FIG. 51) and maintain a stem cell-like phenotype as measured by FACS for the biomarkers CD14, 19, 34, 45, HLA-DR, CD73, 90, 105, CD49a, SSEA-4 and STRO-1 across 3 donors (e.g. as represented FIG. 22) despite additional cell doublings. Biomarkers indicative of "stemness" were maintained when hMSCs were expanded in HS8 supplemented medium.

We also found that these cells are able to readily differentiate into all three mesenchymal stem cell lineages (including bone, as measured by Alizarin red, Von Kossa, Oil-Red-O and Alcian Blue staining) and have enhanced osteogenesis, suggesting this strategy may be effective for orthopedic trauma therapy. HS8 did not adversely affect the ability of MSCs to differentiate into bone.

Figure 52:
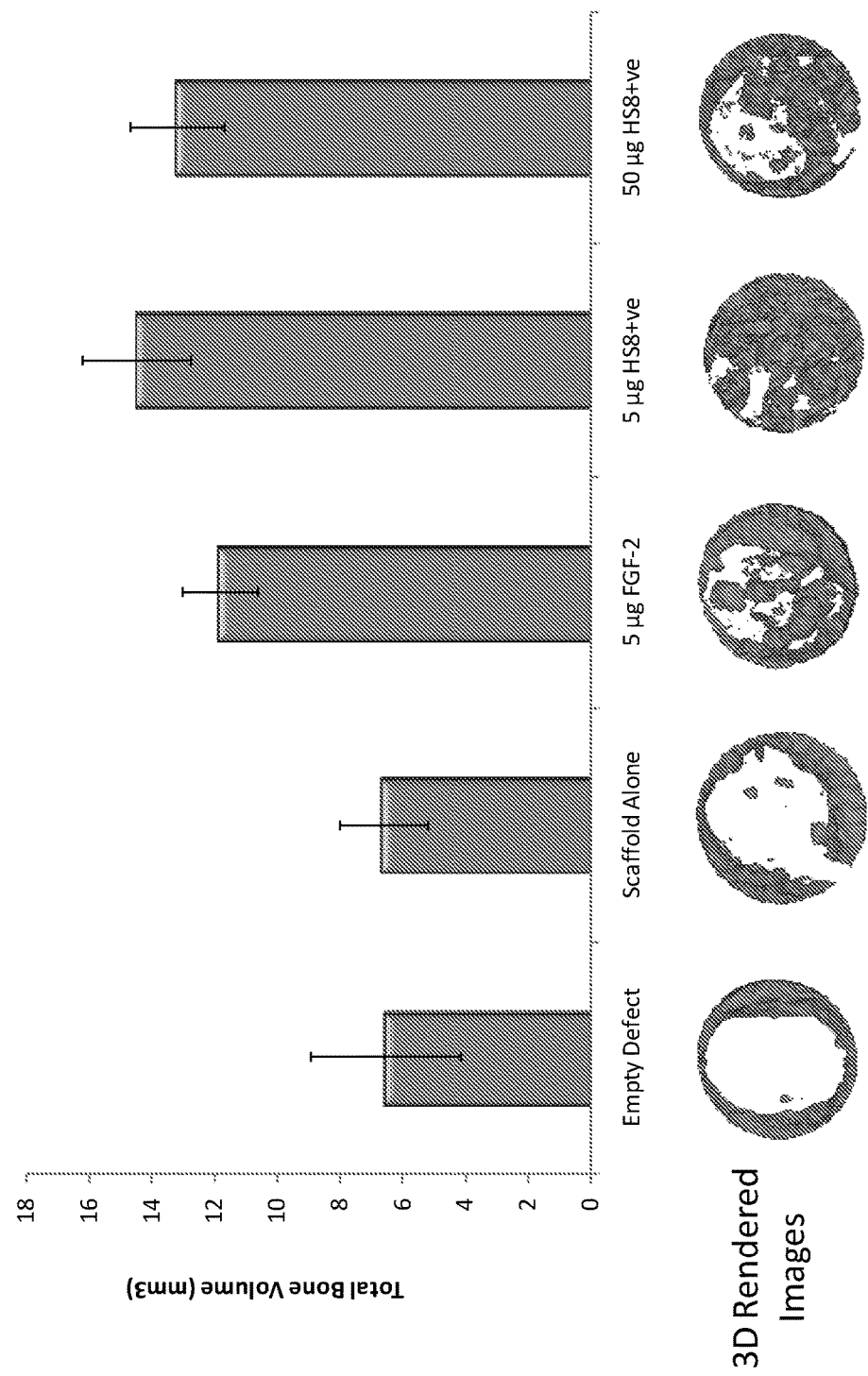
FIG. 52. Graph and micro CT analysis showing that HS8 significantly enhances bone healing in rat critical-sized calvaria defects model.

Therefore, we applied HS8 to a calvarial defect model in rats (FIG. 52). Improved bone healing was evident suggesting that HS8 interacts with FGF2 at the trauma site to accelerate the activity of endogenous stem and osteoprogenitor cells via an FGF-2 dependent mechanism, thus highlighting the therapeutic possibilities of this approach for treating calvarial bone defects.

Example 20—Effect of HS8 on Pig Excisional Wound Model

Pig Skin Wound Healing Protocol

Full thickness excisional wounds were created on the back of five adult micropigs. The back of the anaesthetize pigs was shaved and cleaned with povidone iodine solution. To serve the experimental time points at day 1, 3, 7, 9, 13 and 15, nested wounds were created using a 6 and 10 mm biopsy punch. A set of three wounds is required for the entire experimental time points. The initial three wounds were made with a 6 mm biopsy punch. At day 1, 3 and 7, each wound will be cored out with a 10 mm biopsy punch. By day 16, the 10 mm wounds will serve as day 9, 13 and 15 time points.

Simple randomization of treatments was made, and treatments were initiated by the topical application of 250 μg/uL HS compound via 10 mg/ml carboxymethyl cellulose (CMC) (Sigma) gel (n=6), or CMC gel alone (untreated wound) (n=6). 56.5 uL and 157 uL of compound were applied respectively into the 6 and 10 mm wounds at day 0 and 1. The wounds were covered with Tegaderm dressing (3M Singapore). All of the wounds were examined and photographed weekly following surgery.

The pigs were euthanized at day 16 and full thickness skin samples of the wounds with surrounding unwounded skin were excised and cut into half. One half was fixed in 10% neutral buffered formalin for histological analysis. Another half was placed into TRIzol (Life Technologies) and frozen at −80° C. for subsequent molecular analysis.

A 6 mm punch may be used initially to examine early markers for wound healing (e.g. inflammatory response and re-epithelialization), and may then be cored out with a larger 10 mm punch to look for later markers of wound healing (e.g. blood vessel regrowth, tissue reorganization).

Figure 53A:
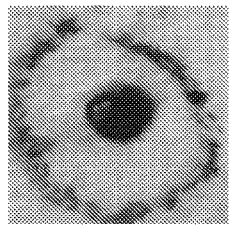
FIG. 53. Photographs showing results of treatment with and without HS8 of a full thickness skin excisional wound (6 mm biopsy punch) pig model. (A) Wound at day 0, (B) Wound at day 7 in the pig treated with carrier (CMC) alone, and (C) Wound at day 7 in the pig treated with carrier+HS8 (250 ug/cm$^3$).
Figure 53B:
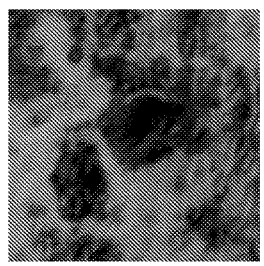
Figure 53C:
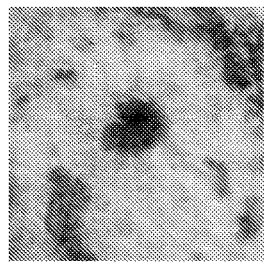

FIG. 53 shows a gross macro view of the flank of a minipig which had undergone the 6 mm punch procedure. These results show that HS8 enhances wound healing in an in vivo minipig model of excisional skin trauma. We also experimentally determined that HS8 is able to trigger the proliferation of dermal fibroblasts through FGF-2-dependent pathways.

The mechanism of action is multivalent. The areas of interest for skin/epithelial wound healing as it pertains to HS8 include healing after plastic surgery, colorectal anastomotic surgery/closing up stitches, treatment of burns, vascular/arterial/pressure ulcer treatment, skin incisional/trauma wound repair, the encouraging of blood vessels back into the epidermal compartment and stimulation of epidermal stem cell function. The primary effect is on FGF-sensitive cells, particularly stem cells, with other effects on dermal fibroblasts and blood vessel formation (angiogenesis).

HS8 enables the enhancement of FGF2, without the fear of an oncogenic outcome. The sugar enhances the naturally expressed FGF-2 already in the skin. HS8 by itself is expected to have major therapeutic effects, in accord with our experimental results.

REFERENCES

1. Ashikari-Hada, S., Habuchi, H., Kariya, Y., Itoh, N., Reddi, A. H., and Kimata, K. (2004). Characterization of Growth Factor-binding Structures in Heparin/Heparan Sulfate Using an Octasaccharide Library. The Journal of Biological Chemistry 279(1)3, 12346-12354
2. Baird, A., Schubert, D., Ling, N., and Guillemin, R. (1988). Receptor- and heparin-binding domains of basic fibroblast growth factor. Proc. Natl. Acad. Sci. USA 85, 2324-2328.
3. Billingham, R. E. (1966-67). The biology of graft-versus-host reactions. Harvey Lect 62, 21-78.
4. Bishop, J. R., Schuksz, M., and Esko, J. D. (2007). Heparan sulphate proteoglycans fine-tune mammalian physiology. Nature 446, 1030-1037
5. Brickman, Y. G., Ford M. D., Small, D. H., Bartletti, P., F., and Nurcombe, V. (1995). Heparan sulfates mediate the binding of basic fibroblast growth factor to a specific receptor on neural precursor cells. J Biolo. Chem. 270 (42), 24941-24948.
6. Brickman, Y. G., Nurcombe, V., Ford, M. D., Gallagher, J. T., Bartlett, P. F. and Turnbull, J. E. (1998). Structural comparison of fibroblast growth factor-specific heparan sulfates derived from a growing or differentiating neuroepithelial cell line. Glycobiology 8(5), 463-471.
7. Cain, S. A., Baldock, C., Gallagher, j., Morgan, A., Bax D. V., Weiss, A. S., Shuttleworth, A. C., and Kielty C. M. (2005). Fibrillin-1 Interactions with heparin-Implications for microfibril and elastic fibre assembly. The Journal of biological Chemistry 280(34), 30526-30537.
8. Caplan, A. I. (2009). Why are MSCs therapeutic? New data: new insight. J Pathol 217, 318-324
9. Cardin, A. D., and Weintraub, H. J. (1989), Molecular modeling of protein-glycosaminoglycan interactions. Arterioscler. Thromb. Vasc. Biol. 9, 21-32
10. Cawthon, R. M. (2002) Telomere measurement by quantitative PCR. Nucleic Acids Res 30, e47.
11. Cool, S. M., and Nurcombe, V. (2005) Substrate Induction of Osteogenesis from Marrow-Derived Mesenchymal Precursors. Stem Cells Dev. 14(6), 632-642.
12. Dominici, M., Le Blanc, K., Mueller, I., Slaper-Cortenbach, I., Marini, F. C., Krause, D. S., Deans R. J., Keating, A., Prockop, D. J., and Horwitz, E. M. (2006). Minimal criteria for defining multipotent mesenchymal stromal cells. The International Society for Cellular Therapy position statement. Cytotherapy 8(4), 315-317
13. Esch, F., Baird, A., Ling, N., et al. (1985) Primary structure of bovine pituitary basic fibroblast growth factor (FGF) and comparison with the amino-terminal sequence of bovine brain acidic FGF. Proc Natl Acad Sci USA; 82:6507-6511
14. Faham, S., Hileman, R. E., Fromm, J. R., Linhardt, R. J., and Rees, D. C. (1996) Heparin structure and interactions with basic fibroblast growth factor. *Science* 271, 1116-1120
15. Ferrara, J. L. M., Levine, J. E., Reddy, P., and Holler, E. (2009). Graft-versus-host disease. Lancet 373, 1550-61
16. Fromm, J. R., Hileman, R. E., Caldwell, E. E., Weiler, J. M., and Linhardt, R. J. (1997). Pattern and spacing of basic amino acids in heparin binding sites. Arch. Biochem. Biophys. 343, 92-100
17. Gandhi, N. S., and Mancera, R. L. (2008). The Structure of glycosaminoglycans and their interactions with proteins. Chem. Biol. Drug. Des. (2008) 72, 455-482
18. Gronthos, S., Zannettino, A. C. W., Graves, S. E., Ohta, S., Hay, S. J., and Simmons, P. J. (1999). Differential cell surface expression of the STRO-1 and alkaline phosphatase antigens on discrete developmental stages in primary cultures of human bone cells. J. Bone Min. Res. 14(1), 47-56.
19. Grünert, M., Dombrowski, C., Sadasivam, M., Manton, K., Coot, S. M., and Nurcombe, V. (2007). Isolation of a native osteoblast matrix with a specific affinity for BMP2. J. Mol. Histo 38, 393-404.
20. Guillot, P. V., Gotherstrom, C., Chan, J., Kurata, H. and Fisk, N. M. (2007) Human first-trimester fetal MSC express pluripotency markers and grow faster and have longer telomeres than adult MSC. Stem Cells 25, 646-654.
21. Hileman, R. E., Fromm, J. R., Weiler, J. M., and Linhardt, R. J. (1998). Glycosaminoglycan-protein interactions: definition of consensus sites in glycosaminoglycan binding proteins. *Bioassays* 20(2), 156-67

22. Kinsella, L., Chen, H., Smith, J. A., Rudland, P. S., and Fernig D. G. (1998). Interactions of putative heparin-binding domains of basic fibroblast growth factor and its receptor, FGFR-1, with heparin using synthetic peptides. Glycoconjugate Journal 15, 419-422
23. Le Blanc, K., Frassoni, F., Bali, L., Locatelli, F, Roelofs, H., Lewis, I., Lanino, E., Sundberg, B., Bernardo, M. E., Remberger, M., Dini, G., Egeler, R. M., Bacigalupo, A., and Fibbe, W., Ringdén, O. (2008). Mesenchymal stem cells for treatment of steroid-resistant, severe, acute graft-versus-host disease: a phase II study. Lancet 371, 1579-1586
24. Lee, J. Y., Choo, J. E., Choi, Y. S., Lee, K. Y., Min, D. S., Pi, S. H., Seol, Y. J., Lee, S. J., Jo, I. H., Chung, C. P., and Park, Y. J. (2007). Characterization of the surface immobilized synthetic heparin binding domain derived from human fibroblast growth factor-2 and its effect on osteoblast differentiation. *J Biomed Mater Res A* 15; 83(4), 970-9.
25. Matsubara, T., Tsutsumi. S., Pan, H., Hiraoka, H., Oda, R., Nishimura, M., Kawaguchi, H., Nakamura, K., and Kato, Y. (2004). A new technique to expand human mesenchymal stem cells using basement membrane extra-cellular matrix. Biochemical and Biophysical Research Communications 313(3),503-508
26. Meuleman N., Tondreau T., Ahmad. I., Kwan, J., Crokaert, F., Delforge, A., Dorval, C., Martiat, P., Lewalle, P., Lagneaux, L., and Bron D. (2009). Infusion of mesenchymal stromal cells can aid hematopoietic recovery following allogeneic hematopoietic stem cell myeloablative transplant: a pilot study. *Stem Cells Dev.* 18(9),1247-52.
27. Murali, S., Manton, K. J., Tjong, V., Su, X., Haupt, L. M, Cool, S. M., and Nurcombe, V. (2009) Purification and characterization of heparan sulfate from human primary osteoblasts. Journal of cellular biochemistry 108, 1132-1142 (2009)
28. Nurcombe, V., Ford, M. D., Wildschut, J. A., and Bartlett, P. F. (1993). Developmental regulation of neural response to FGF-1 and FGF-2 by heparan sulfate proteoglycan. Science, 260(5104), 103-106.
29. Ono, K., Hattori, H., Takeshita, S., Kurita, A., and Ishihara, M. (1999). Structural features in heparin that interact with VEGF165 and modulate its biological activity. Glycobiology. 9(7),705-11.
30. Ornitz, D. M., Xu, J., Colvin, J. S., McEwen, D. G., MacArthur, C. A., Coulieri, F., Gao, G., and Goldfarb, M. (1996). Receptor Specificity of the Fibroblast Growth Factor Family. J Biol. Chem. 271(25), 15292-15297
31. Ori, A., Free, P., Courty, J., Wilkinson, M. C., and Fernig D. G. (2009). Identification of Heparin-binding Sites in Proteins by Selective Labeling. Molecular & Cellular Proteomics 8, 2256-2265
32. Ori, A., Wilkinson, M. C., and Fernig, D., G. (2008). The heparanome and regulation of cell function: structures, functions and challenges. *Front Biosci.* 1(13),4309-38.
33. Pellegrini, L. (2001). Role of heparan sulfate in fibroblast growth factor signalling: a structural view. Curr. Opin. Struc. Biol. 11, 629-634
34. Ren, G. S, J., Zhang, L., zhao, X., Ling, W., L'huillie, A., Zhang, J., Lu, Y., Roberts, A. I., Ji, W., Zhang, H., Rabson, A. B., and Shi, Y. (2009). Species Variation in the Mechanisms of Mesenchymal Stem Cell-Mediated Immunosuppression. Stem cells 27, 1954-1962
35. Shi, Y., Hu, G., Su, J., Li, W., Chen, C., Shou, P. Xu, C, Chen, X., Huang, Y., Zhu, Z., Huang, X., Han, X., Xie, N., and Ren, G. (2010). Mesenchymal stem cells: a new strategy for immunosuppression and tissue repair. Cell Research 20, 510-518.
36. Si, Y. L., Zhao, Y. L., Hao, H. J., Fu, X. B., and Han, W. D. (2011). MSCs: Biological characteristics, clinical applications and their outstanding concerns. Ageing Research Reviews 10, 93-103
37. Sotiropoulou, P. A., Perez, S. A., Salagianni, M., Baxevanis, C. N, and Papamichail, M. (2006). Characterization of the Optimal Culture Conditions for Clinical Scale Production of Human Mesenchymal Stem Cells. Stem cells 24, 462-471
38. Tisato, V., Naresh, K., Girdlestone, J., Navarrete, C., and Dazzi, F. (2007). Mesenchymal stem cells of cord blood origin are effective at preventing but not treating graft-versus-host disease. Leukemia 21, 1992-9.
39. Toubai, T., Paczesny, S., Shono. Y., Tanaka, J., Lowler, K. P., Malter, C. T., Kasai, M., and Imamura, M. (2009). Mesenchymal stem cells for treatment and prevention of graft-versus-host disease after allogeneic hematopoietic cell transplantation. *Curr. Stem. Cell. Res. Ther.* 4(4), 252-9.
40. Thompson, L. D., Pantoliano, M. W., and Springer B. A. (1994). Energetic characterization of the basic fibroblast growth factor-heparin interaction: identification of the heparin binding domain. Biochemistry 33, 3831-3840
41. Uniewicz, K. A., Ori, A., Xu, R., Ahmed, Y., Wilkinson, M. C., Fernig, D. G., and Yates, E. A. (2010). Differential Scanning Fluorimetry Measurement of Protein Stability Changes upon Binding to Glycosaminoglycans: A Screening Test for Binding Specificity. Anal. Chem., 82 (9), 3796-3802
42. Walsh, S., Jefferiss, C., Stewart, K., Jordan, G. R., Screen, J., and Beresford, J. N. (2000). Expression of the developmental markers STRO-1 and alkaline phosphatase in cultures of human marrow stromal cells: regulation by fibroblast growth factor (FGF)-2 and relationship to the expression of FGF receptors 1-4. Bone 27(2). 185-195.
43. Zannettino, A. C., Paton, S., Itescu, S., and Gronthos, S. (2010). Comparative assessment of the osteoconductive properties of different biomaterials in vivo seeded with human or ovine mesenchymal stem/stromal cells. *Tissue Eng Part A.* 16(12), 3579-87.
44. Zulma Gazit, Z., Pelled, G. Sheyn, D., Kimelman, N. and Gazit, N. (2011). Mesenchymal Stem Cells. Principles of Regenerative Medicine Chapter 17, 285-304
45. Friedenstein A J, Piatetzky S II, Petrakova K V (1966) Osteogenesis intransplants of bone marrow cells. J Embryol Exp Morphol 16:381-390
46. Gimble J, Guilak F (2003) Adipose-derived adult stem cells: isolation, characterization, and differentiation potential. Cytotherapy 5:362-369
47. Zuk P A, Zhu M, Mizuno H, Huang J, Futrell J W, Katz A J, Benhaim P, Lorenz H P, Hedrick M H (2001) Multilineage cells from human adipose tissue: implications for cell-based therapies. Tissue Eng 7:211-228
48. Bieback K, Kern S, Kluter H, Eichler H (2004) Critical parameters for the isolation of mesenchymal stem cells from umbilical cord blood. Stem Cells 22:625-634
49. Erices A, Conget P, Minguell J J (2000) Mesenchymal progenitor cells in human umbilical cord blood. Br J Haematol 109:235-242
50. Goodwin H S, Bicknese A R, Chien S N, Bogucki B D, Quinn C O, Wall D A (2001) Multilineage differentiation activity by cells isolated from umbilical cord blood: expression of bone, fat, and neural markers. Biol Blood Marrow Transplant 7:581-588

51. Kogler G, Sensken S, Airey J A, Trapp T, Muschen M, Feldhahn N, Liedtke S, Sorg R V, Fischer J, Rosenbaum C et al (2004) A new human somatic stem cell from placental cord blood with intrinsic pluripotent differentiation potential. J Exp Med 200:123-135
52. Wagner W, Wein F, Seckinger A, Frankhauser M, Wirkner U, Krause U, Blake J, Schwager C, Eckstein V, Ansorge W, Ho A D (2005) Comparative characteristics of mesenchymal stem cells from human bone marrow, adipose tissue, and umbilical cord blood. Exp Hematol 33:1402-1416
53. Jiang Y, Vaessen B, Lenvik T, Blackstad M, Reyes M, Verfaillie C M (2002) Multipotent progenitor cells can be isolated from postnatal murine bone marrow, muscle, and brain. Exp Hematol 30:896-904

The invention claimed is:

1. A method of healing a skin wound comprising contacting the skin wound with an effective amount of a pharmaceutical composition comprising heparan sulphate HS8, wherein the heparan sulphate HS8 is capable of specific binding to a peptide or polypeptide consisting of the amino acid sequence YCKNGGF (SEQ ID NO:2) and optionally 1 to 20 additional amino acids at one or both ends of the amino acid sequence SEQ ID NO:2, thereby promoting growth of skin cells.

2. A method of treating a subject having a skin wound, the method comprising administration of a therapeutically effective amount of heparan sulphate HS8 to the subject leading to repair and/or regeneration of skin at the wound, wherein the heparan sulphate HS8 is capable of binding a peptide or polypeptide consisting of the amino acid sequence YCKNGGF (SEQ ID NO:2) and optionally 1 to 20 additional amino acids at one or both ends of the amino acid sequence SEQ ID NO:2.

3. The method of claim 1 wherein the skin wound is a skin burn, ulcer, excisional wound, cut, stab or puncture wound.

4. A method of skin grafting, skin reconstruction, or skin plastic surgery comprising contacting skin at or adjacent the region of grafting, reconstruction or plastic surgery with an effective amount of a pharmaceutical composition comprising heparan sulphate HS8, wherein the heparan sulphate HS8 is capable of specific binding to a peptide or polypeptide consisting of the amino acid sequence YCKNGGF (SEQ ID NO:2) and optionally 1 to 20 additional amino acids at one or both ends of the amino acid sequence SEQ ID NO:2, thereby promoting growth of skin cells.

5. The method of claim 1 wherein the heparan sulphate HS8 or pharmaceutical composition is formulated for topical or transdermal administration.

6. The method of claim 1 wherein the heparan sulphate HS8 or pharmaceutical composition is formulated as a gel, spray, paste, ointment, cream, lotion, salve, oil, aqueous solution, suspension, dispersion, patch, adhesive plaster, bandage, dressing, depot, or reservoir.

7. The method of claim 1 wherein the method further comprises administration of a growth factor and/or mesenchymal stem cells.

8. The method of claim 1 wherein the heparan sulphate HS8 or pharmaceutical composition is formulated as a combined preparation with a growth factor and/or with mesenchymal stem cells.

9. The method of claim 1 wherein the heparan sulphate HS8 is provided in isolated or substantially purified form.

10. The method of claim 1 wherein the heparan sulphate HS8 is capable of binding a peptide or polypeptide comprising the amino acid sequence GHFKDPKRLYCKNGGF (SEQ ID NO: 1).

11. The method of claim 1 wherein following digestion with heparin lyases I, II and III and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0. |

12. The method of claim 1 wherein the heparan sulphate HS8 is obtained by a method comprising:

(i) providing a solid support having polypeptide molecules adhered to the support, wherein the polypeptide comprises a heparin-binding domain comprising the amino acid sequence YCKNGGF;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes; and (v) collecting the dissociated glycosaminoglycans.

13. The method of claim 2 wherein the heparan sulphate HS8 is capable of binding a peptide or polypeptide comprising the amino acid sequence GHFKDPKRLYCKNGGF (SEQ ID NO:1).

14. The method of claim 2 wherein following digestion with heparin lyases I, II and III and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |

| Disaccharide | Normalised weight percentage |
| --- | --- |
| ΔUA,2S-GlcNAc | 1.0 ± 0.5 |
| ΔUA-GlcNAc,6S | 8.9 ± 3.0 |
| ΔUA-GlcNAc | 32.5 ± 3.0. |

15. The method of claim 2 wherein the heparan sulphate HS8 or pharmaceutical composition is formulated for topical or transdermal administration.

16. The method of claim 2 wherein the skin wound is a skin burn, ulcer, excisional wound, cut, stab or puncture wound.

17. The method of claim 4 wherein the heparan sulphate HS8 is capable of binding a peptide or polypeptide comprising the amino acid sequence GHFKDPKRLYCKNGGF (SEQ ID NO:1).

18. The method of claim 4 wherein following digestion with heparin lyases I, II and III and then subjecting the resulting disaccharide fragments to capillary electrophoresis analysis the heparan sulphate HS8 has a disaccharide composition comprising:

| Disaccharide | Normalised weight percentage |
| --- | --- |
| ΔUA,2S-GlcNS,6S | 12.7 ± 3.0 |
| ΔUA,2S-GlcNS | 7.2 ± 2.0 |
| ΔUA-GlcNS,6S | 15.5 ± 3.0 |
| ΔUA,2S-GlcNAc,6S | 6.5 ± 2.0 |
| ΔUA-GlcNS | 15.7 ± 3.0 |
| ΔUA,2S-GlcNAc | 1.0 ± 0.5 |
| ΔUA-GlcNAc,6S | 8.9 ± 3.0 |
| ΔUA-GlcNAc | 32.5 ± 3.0. |

19. The method of claim 4 wherein the heparan sulphate HS8 or pharmaceutical composition is formulated for topical or transdermal administration.

20. The method of claim 7, wherein the growth factor is FGF2.

* * * * *